US010538534B2

(12) United States Patent
Williams et al.

(10) Patent No.: US 10,538,534 B2
(45) Date of Patent: Jan. 21, 2020

(54) SYNTHESIS AND UTILITY OF NEW CAPGROUP LARGAZOLE ANALOGS

(71) Applicants: Colorado State University Research Foundation, Fort Collins, CO (US); Dana-Farber Cancer Institute, Inc., Boston, MA (US); University of Notre Dame du Lac, South Bend, IN (US)

(72) Inventors: Robert M. Williams, Fort Collins, CO (US); James E. Bradner, Weston, MA (US); Dane Clausen, Rahway, NJ (US); Olaf G. Wiest, South Bend, IN (US); Le Zhao, Fort Collins, CO (US); Christine Elizabeth Dunne, Fort Collins, CO (US)

(73) Assignees: Colorado State University Research Foundation, Fort Collins, CO (US); Dana-Farber Cancer Institute, Inc., Boston, MA (US); University of Notre Dame du Lac, South Bend, IN (US)

( * ) Notice: Subject to any disclaimer, the term of this patent is extended or adjusted under 35 U.S.C. 154(b) by 0 days.

(21) Appl. No.: 15/555,792

(22) PCT Filed: Mar. 4, 2016

(86) PCT No.: PCT/US2016/021031
§ 371 (c)(1),
(2) Date: Sep. 5, 2017

(87) PCT Pub. No.: WO2016/144814
PCT Pub. Date: Sep. 15, 2016

(65) Prior Publication Data
US 2018/0057510 A1    Mar. 1, 2018

Related U.S. Application Data

(60) Provisional application No. 62/129,174, filed on Mar. 6, 2015.

(51) Int. Cl.
*C07D 513/18* (2006.01)
*A61K 31/429* (2006.01)
*A61K 45/06* (2006.01)

(52) U.S. Cl.
CPC .......... *C07D 513/18* (2013.01); *A61K 31/429* (2013.01); *A61K 45/06* (2013.01)

(58) Field of Classification Search
CPC ............................ C07D 513/08; A61K 31/429
See application file for complete search history.

(56) References Cited

U.S. PATENT DOCUMENTS

| 4,456,592 | A  | 6/1984  | Okumura et al. |
| 5,846,933 | A  | 12/1998 | Korngold et al. |
| 6,509,315 | B1 | 1/2003  | Joullie et al. |
| 8,217,076 | B2 | 7/2012  | Williams |
| 8,513,290 | B2 | 8/2013  | Williams |
| 9,186,402 | B2 * | 11/2015 | Williams ............. C07D 498/18 |
| 2005/0119169 | A1 | 6/2005 | Deslongchamps et al. |
| 2007/0129289 | A1 | 6/2007 | Joullie et al. |
| 2014/0080802 | A1 | 3/2014 | Holson et al. |
| 2014/0093449 | A1 * | 4/2014 | Williams ............. C07D 498/18 |
| | | | 424/1.49 |
| 2015/0010541 | A1 | 1/2015 | Liu et al. |
| 2018/0044376 | A1 | 2/2018 | Williams |

FOREIGN PATENT DOCUMENTS

| JP | 03-141296 | 6/1991 |
| WO | WO 2007/061939 | 5/2007 |
| WO | WO 2007/100385 | 9/2007 |
| WO | WO 2009/032352 | 3/2009 |
| WO | WO 2010/009334 | 1/2010 |
| WO | WO 2016/144665 | 9/2016 |

OTHER PUBLICATIONS

Zawilska. Pharmacological Reports, 2013, 65, 1-14 (Year: 2013).*
"Can child leukemia be prevented?", https://www.cancer.org/cancer/leukernia-in-children/causes-risks-prevention/prevention.html, last revised Feb. 3, 2016, accessed Oct. 25, 2018 (Year: 2016).*
Souto. Journal of Medicinal Chemistry, 2010, 53, 4654-67 (Year: 2010).*
Salvador. ACS Medicinal Chemistry Letters, 2014, 5, 905-10 (Year: 2014).*
Hong. Natural Products Reports, 2012, 29, 449-56 (Year: 2012).*
Quintas-Cardama. Leukemia, 2011, 25, 226-35 (Year: 2011).*
Zhao. Israel Journal of Chemistry, 2017, 57, 319-330 (Year: 2017).*
Liu. Journal of Pharmacology and Experimental Therapeutics, 2010 , 335, 351-361 (Year: 2010).*
Hong. Natural Product Reports, 2012, 29, 449-56 (Year: 2012).*
Avenoza A., et al. (2001) Tetrahedron: Asymmetry 12(6):949-957 "Enantioselective synthesis of (S)-and (R)-methylserines: application to the synthesis of (S)-and (R)-N-Boc-N,O-isopropylidene-a-methylserinals".
Berge, et al. (1977) J. Pharm. Sci. 66:1-19 "Pharmaceutical salts".
Bolden, J. E., et al. (2006) Nat. Rev. Drug Discovery 5:769-784 "Anticancer activities of histone deacetylase inhibitors".
Bowers, A.A., et al. (2008) J Am Chem Soc 130:11219-22 Total "Synthesis and Biological Mode of Action of Largazole: A Potent Class I Histone Deacetylase Inhibitor".
Bowers, A.A., et al. (2009) Org. Letters 11(6) 1301-1304 "Synthesis and Histone Deacetylase Inhibitory Activity of Largazole Analogs: Alteration of the Zinc-Binding Domain and Macrocyclic Scaffold".
Bradner (2010) Nat. Chem Biol. 6(3):238-243, "Chemical Phylogenetics of Histone Deacetylases".
Burger's Medicinal Chemistry and Drug Discovery (1995, Manfred E. Wolff ed., 5th ed. 172-178, 929-932).
Chen, Y., et al. (2003) J Org Chem 68:8902-8905 "Total Synthesis of the Depsipeptide FR-901375".
Cleve, Trip Report for 9th Tetrahedron Symposium, Berkeley, CA Klos, Jul. 22-25, 2008, "Discovery and Optimization of Diamine Analogues as Potent Inhibitors of Leukotriene A4 Hydrolase.".

(Continued)

*Primary Examiner* — Noble E Jarrell
(74) *Attorney, Agent, or Firm* — Leydig, Voit & Mayer, Ltd.

(57) ABSTRACT

Analogs of largazole are described herein. Methods of treating cancer, blood disorders, autoimmune disease, and Alzheimer's Disease using largazole analogs and pharmaceutical compositions comprising the same are additionally described herein. Methods for preparing largazole analogs are likewise described.

18 Claims, 22 Drawing Sheets

(56) References Cited

OTHER PUBLICATIONS

Freireich, et al. (1966) Cancer Chemother Rep 50:219 "Quantitative comparison to toxicity of anticancer agents in mouse, rat, hamster, dog, monkey and man".
Furumai, R., et al. (2001) PNAS USA 98:87-92 "Potent Histone Deacetylase Inhibitors Built From Trichostatin A and Cyclic Tetrapeptide Antibiotics Including Trapoxin".
Ghosh, A.K. & Kulkarni, S. (2008) Org. Lett. 10:3907-3909 "Enantioselective Total Synthesis of (+)-Largazole, a Potent Inhibitor of Histone Deacetylase".
Greshock, et al. (2008) Org Lett 10:613-616 "Improved Total Synthesis of the Potent HDAC Inhibitor FK228 (FR-901228)".
Grozinger, C.M., et al. (1999) Proc. Nat. Acad. Sci. USA 96:4868-4873 "Three proteins define a class of human histone deacetylases related to yeast Hdalp".
Handbook of Pharmaceutical Salts. Properties, Selection, and Use (P. Heinrich Stahl and C. Wermuth, Eds., Verlag Helvetica Chica Acta, Zurich, Switzerland (2002)).
International Preliminary Report on Patentability from PCT/US2016/020561 dated Sep. 21, 2017.
International Search Report and Written Opinion from PCT/US09/50878 dated Sep. 28, 2009.
International Search Report and Written Opinion from PCT/US16/20561 dated May 2, 2016.
Jeanguenat, A. & Seebach, D. (1991) J Chem Soc, Perkins Trans 1:2291-2298 "Stereoselective chain elongation at C-3 of cysteine through 2,3-dihydrothiazoles, without racemization. Preparation of 2-amino-5-hydroxy-3-mercaptoalkanoic acid derivatives".
Johnstone, R.W. (2002) Nature Rev. Drug Disc. 1:287-299 "Histone deacetylase inhibitors: novel drugs for the treatment of cancer".
Katsura, Y., et al. (1994) J Med Chem 37(1):57-66 "Studies on antiulcer drugs. 7. 2-Guanidino-4-pyridylthiazoles as histamine H2-receptor antagonists with potent gastroprotective effects against nonsteroidal antiinflammatory drug-induced injury".
Lange, U.E.W., et al. (1999) Tetrahedron Lett. 40:7067-7070 "A new mild method for the synthesis of amidines".
Li, K.W., et al. (1996) J Am Chem Soc 118:7237-7238 "Total Synthesis of the Antitumor depsipeptide FR-901, 228."
Marsault, et al. (2006) Journal of Medicinal Chemistry pp. C-D "Discovery of a New Class of Macrocyclic Antagonists to the Human Motilin Receptor.".
Masuoka, Y., et al. (2001) Tetrahedron Lett. 42:41-44 "Spiruchostatins A and B, novel gene expression-enhancing substances produced by *Pseudomonas* sp."
Miller, T. A., et al. (2003) J. Med. Chem. 46:5097-5116 "Histone deacetylase inhibitors".
Minucci, S., et al. (2006) Nature Rev. Cancer 6:38-51 "Histone deacetylase inhibitors and the promise of epigenetic (and more) treatments for cancer".
Moradei, O., et al. (2005) Curr. Med. Chem. Anti-Cancer Agents 5:529-560 "Histone deacetylase inhibitors: latest developments, trends and prospects".
Mulqueen, G.C., et al. (1993) Tetrahedron 49:5359-5364 "Synthesis of the thiazoline-based siderophore (5)-desferrithiocin".
Nasveschuk, C.G., et al. (2008) Org. Lett. 10:3595-3598 "A Concise Total Synthesis of Largazole, Solution Structure, and Some Preliminary Structure Activity Relationships".
Nishino, N., et al. (2003) Org Lett 5:5079-5082 "cyclic tetrapeptides bearing a sulfhydryl group potently inhibit histone deacetylases".
Patani and LaVoie (1996) Chem. Rev. 96:3147-3176 "Bioisosterism: A Rational Approach in Drug Design".
Phillips, A.J., et al. (2000) Org Lett 2(8):1165-1168 "Synthesis of Functionalized Oxazolines and Oxazoles with DAST and Deoxo-Fluor".
Reiner, J., et al. (2002) Bioorg Med Chem Lett 12(8):1203-1208 "Non-covalent thrombin inhibitors featuring p3-heterocycles with P1-monocyclic arginine surrogates".
Scientific Tables, Geigy Pharmaceuticals, Ardley, N.Y., (1970) 537.
Seiser, T.; et al. (2008) Angew. Chem. Int. Ed. 47:6483-6485 "Synthesis and Biological Activity of Largazole and Derivatives".
Shigematsu, N., et al. (1994) J. Antibiot. 47:311-314 "A novel antitumor bicycle depsipeptide produced by Chromobacterium violaceum No. 968".
Smith, N.D. and Goodman, M. (2003) Org. Lett. 5:1035-1037 "Enantioselective synthesis of alpha-methyl-D-cysteine and lanthionine building blocks via alpha-methyl-D-serine-beta-lactone".
Somech, R., et al. (2004) Cancer Treat. Rev. 30:461 "Histone deacetylase inhibitors—a new tool to treat cancer".
Taori, K., et al. (2008) J. Am. Chem. Soc. 130:1806-1807 and 13506 "Structure and Activity of Largazole, a Potent Antiproliferative Agent from the Floridian Marine *Cyanobacterium symploca* sp.".
Taunton, J., et al. (1996) Science 272:408-411 "A Mammalian Histone Deacetylase Related to the Yeast Transcriptional Regulator Rpd3p".
Townsend, P.A., et al. (2007) The bicyclic depsipeptide family of histone deacetylase inhibitors, in Chemical Biology; Schreiber, S.L., et al. Eds.Wiley-VCH Verlag GmbH & Co. 693-720.
Ueda, H., et al. (1994) J. Antibiot. 47:315-323 "FR901228, a novel antitumor bicyclic depsipeptide produced by Chromobacterium violaceum No. 968 III. Antitumor activities on experimental tumors in mice".
Ueda, H., et al. (1994) J. Antibiot. 47:301-310 "FR901228, a novel antitumor bicyclic depsipeptide produced by Chromobacterium violaceum No. 968. I. Taxonomy, fermentation, isolation, physicochemical and biological properties, and antitumor activity".
Vanommeslaeghe, K., et al. (2005) Bioorg. Med. Chem. 13:3987-3992 "Theoretical study revealing the functioning of a novel combination of catalytic motives in Histone Deacetylase".
Vanommeslaeghe, K., et al. (2005) Bioorg. Med. Chem. 13:6070-6082 "DFT-based Ranking of Zink-chelating Groups in Histone Deacetylase Inhibitors".
Videnov, G., et al. (1996) Angew Chem Int Ed Eng 35:1503-1506 "Synthesis of Naturally Occurring, Conformationally Restricted Oxazole and Thiazole Containing Di- and Tripeptide Mimetics".
Ying, Y., et al. (2008) J. Am. Chem. Soc. 130:8455-8459 "Total Synthesis and Molecular Target of Largazole, a Histone Deacetylase Inhibitor".
Ying, Y., et al. (2008) Organic Letters 10(18):4021-4024 "Synthesis and Activity of Largazole Analogues with Linker and Macrocycle Modification".
Yoshida, M., et al. (1990) J. Antibiot. 43:1101-1106 "Structural Specificity for Biological Activity of Trichostatin A, A Specific Inhibitor of Mammalian Cell Cycle with Potent Differentiation-Inducing Activity in Friend Leukemia Cells".
Yoshida, M., et al. (1990) J. Biol. Chem. 265:17174 "Potent and specific inhibition of mammalian histone deacetylase both in vivo and in vitro by trichostatin A".
Yurek-George, A. (2007) J. Med. Chem. 50:5720-5726 "The First Biologically Active Synthetic Analogues of FK228, the Depsipeptide Histone Deacetylase Inhibitor".
Yurek-George, A., et al. (2004) J Am Chem Soc 126:1030-1031 "Total synthesis of spiruchostatin A, a potent histone deacetylase inhibitor".
International Search Report and Written Opinion for PCT/US2016/021031 dated May 23, 2016.
International Preliminary Report on Patentability for PCT/US2016/021031 dated Sep. 21, 2017.
International Preliminary Report on Patentability from PCT/US2016/021031 dated Sep. 21, 2017.
International Search Report and Written Opinion from PCT/US16/21031 dated May 23, 2016.
Clausen, et al. (2015) Bioorg. & Med. Chem. 23:5061-5074 "Modular Synthesis and Biological Activity of Pyridyl-based Analogs of the Potent Class 1 Histone Deacetylase Inhibitor Largazole".
Guerra-Bubb, J.M., Bowers, A.A., Smith, W.B., Paranal, R., Estiu, G., Wiest, O., Bradner, J.E. and Williams, R.M., Bioorganic & Medicinal Chemistry Letters, (2013) 23(21), pp. 6025-6028. "Synthesis and HDAC inhibitory activity of isosteric thiazoline-oxazole largazole analogs.".

* cited by examiner

| Compound | HDAC1 | HDAC2 | HDAC3 | HDA6 | HDAC8 |
|---|---|---|---|---|---|
| Largazole | 10.09 | 18.65 | 9.09 | 165.6 | 1068 |
| 1 | 50 | 500 | 500 | >10,000 | 2.8 |
| 5 | 2.51 | 4.19 | 2.78 | 28.11 | 228.4 |
| 6 | 1.95 | 3.38 | 2.59 | 102 | 255.3 |
| 7 | 544.1 | 825.2 | 1151 | - | - |
| 8 | 340 | 655.4 | 319.5 | - | - |
| 9 | 2.2 | 4.42 | 2.31 | 35.16 | 101.8 |
| 10 | 816.9 | 1240 | 846.5 | - | - |
| 11 | 13.2 | 20.77 | 14.59 | 2849 | 1491 |
| 12 | 203.6 | 349.5 | 332.1 | - | - |
| 13 | 2.68 | 4.39 | 3.07 | 48.55 | 341.3 |
| 14 | 340.3 | 471.8 | 332.4 | - | - |
| 15 | 42 | 69.8 | 42.5 | - | - |
| 16 | 950 | 2100 | 1900 | 1100 | - |
| 17 | 4.4 | 20 | 72 | 98 | 1200 |
| 20 | 150 | 1300 | 550 | 50 | - |
| 26 | 0.01 | 0.3 | 0.1 | 8 | 400 |
| 52 | 0.166 | 2.61 | 0.734 | 14.9 | 94 |
| 54 | 0.238 | 2.84 | 1.064 | 36.51 | 129.3 |

Fig. 2

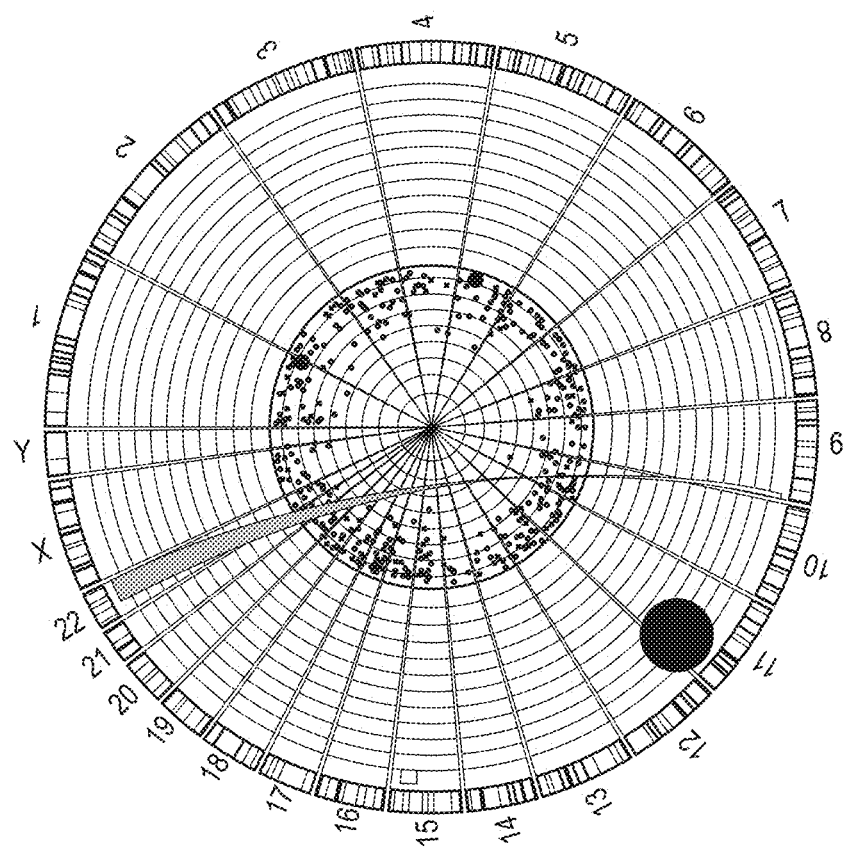
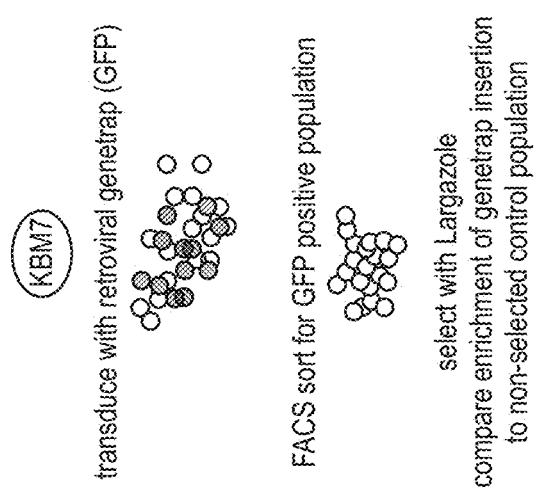
Fig. 8B
Fig. 8A

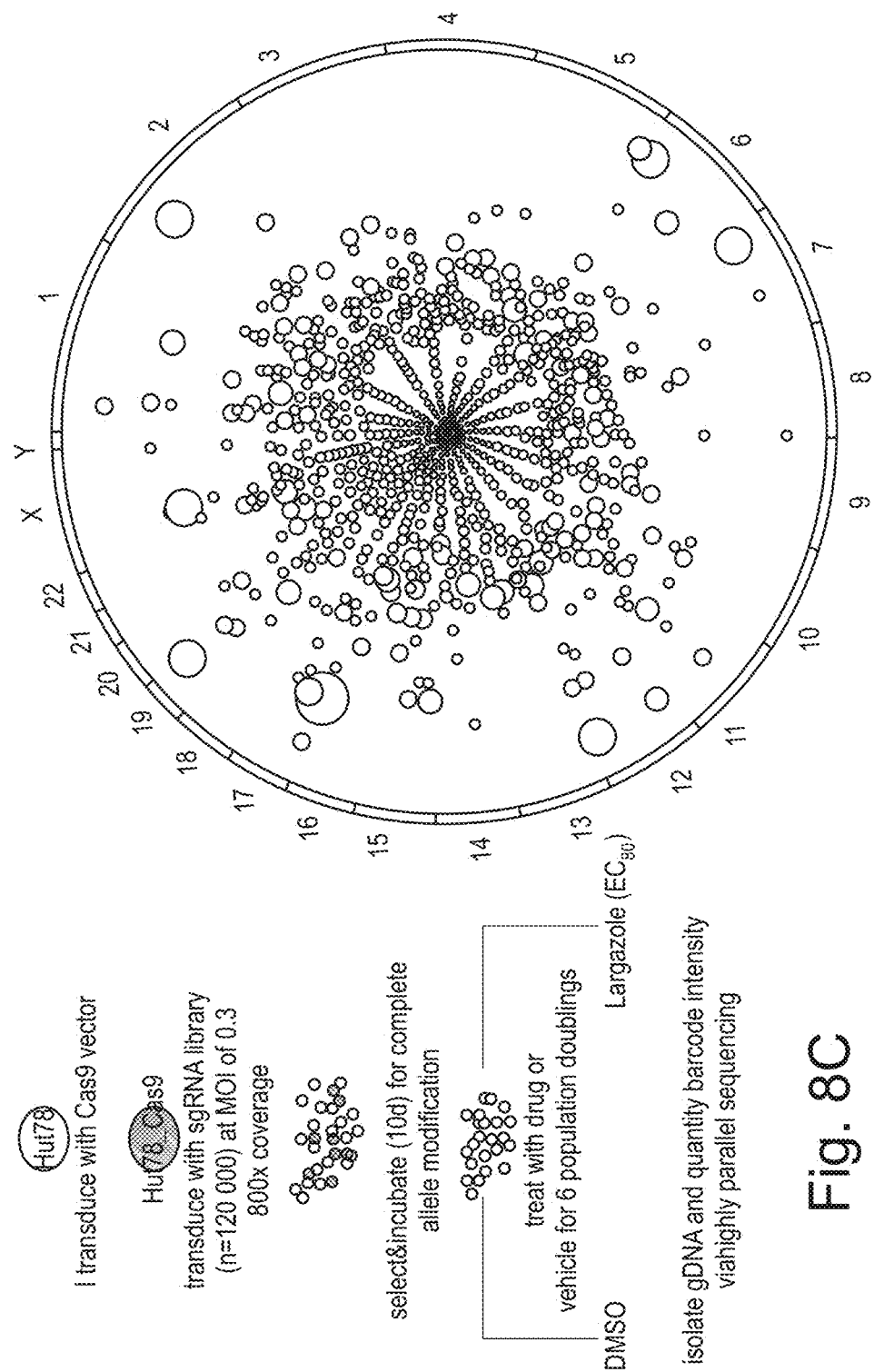

—O— Octanoylated Largazole Peptide Folate (Amide Linker)
—□— Largazole Thiol Peptide Folate (crude)
—△— Octanoylated Largazole Peptide Folate (Ester Linker)
—O— DMSO

SYNTHESIS AND UTILITY OF NEW CAPGROUP LARGAZOLE ANALOGS

RELATED APPLICATIONS

This application is a 35 U.S.C. § 371 national phase application of PCT/US2016/021031 (WO 2016/144814), filed on Mar. 4, 2016, entitled "Synthesis and Utility of New Capgroup Largazole Analogs", which application claims the benefit of U.S. Provisional Application Ser. No. 62/129,174, filed on Mar. 6, 2015, which is incorporated herein by reference in its entirety.

STATEMENT OF RIGHTS TO INVENTIONS MADE UNDER FEDERALLY SPONSORED RESEARCH

This invention was made with government support under grant number R01CA152314 awarded by The National Institutes of Health. The government has certain rights in the invention.

BACKGROUND OF THE INVENTION

Largazole (1) is a densely functionalized macrocyclic depsipeptide, recently isolated from the cyanobacterium *Symploca* sp. (Taori, K., et al. 2008 *J. Am. Chem. Soc.* 130:1806-1807 and 13506; Ying, Y., et al. 2008 *J. Am. Chem. Soc.* 130). This natural product exhibits exceptionally potent and selective biological activity, with two- to ten-fold differential growth inhibition in a number of transformed and non-transformed human- and murine-derived cell lines. The remarkable selectivity of this agent against cancer cells prompts particular interest in its mode of action and its value as a potential cancer chemotherapeutic.

It has previously been stated that "the 3-hydroxy-7-mercaptohept-4-enoic acid unit in 1 is unprecedented in natural products." (Somech, R., et al. 2004 *Cancer Treat. Rev.* 30:461-472; Miller, T. A., et al. 2003 *J. Med Chem.* 46:5097-5116; Moradei, O., et al. 2005 *Curr. Med. Chem.; Anti-Cancer Agents* 5:529-560; Bolden, J. E., et al. 2006 *Nat. Rev. Drug Discovery* 5:769-784). In contrast to this assertion, the (S)-3-hydroxy-7-mercaptohept-4-enoic acid is, in fact, an essential motif in several cytotoxic natural products, including FK228 (FR901228) (Japanese Patent No. 03-141296, Jun. 17, 1991, Fujisawa Pharmaceutical Co., Ltd., Jpn. Kokai Tokkyo Koho J P, 1991; Ueda, H., et al. 1994; *J. Antibiot.* 47:301-310; Shigematsu, N., et al. 1994 *J. Antibiot.* 47:311-314; Ueda, H., et al. 1994 *J. Antibiot.* 47:315-323), FR901375 (Japanese Patent No. 03-141296, Jun. 17, 1991, Fujisawa Pharmaceutical Co., Ltd., Jpn. Kokai Tokkyo Koho J P; Ueda, H., et al. 1994; *J. Antibiot.* 47:301-310; Shigematsu, N., et al. 1994 J. Antibiot. 47:311-314; Ueda, H., et al. 1994 *J. Antibiot.* 47:315-323) and spiruchostatin (Masuoka, Y., et al. 2001 *Tetrahedron Lett.* 42:41-44) (structures depicted below), all of which are known histone deacetylase inhibitors (HDACi) (Townsend, P. A., et al. 2007 *The bicyclic depsipeptide family of histone deacetylase inhibitors, in Chemical Biology*; Schreiber, S. L., et al. Eds. Wiley-VCH Verlag GmbH & Co. 693-720).

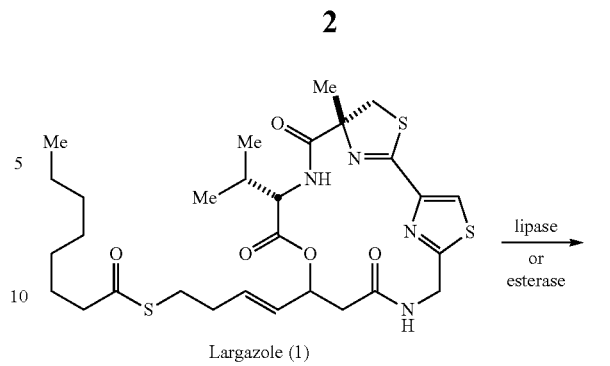

Largazole (1)

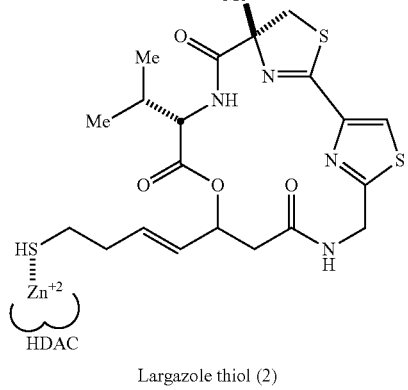

Largazole thiol (2)

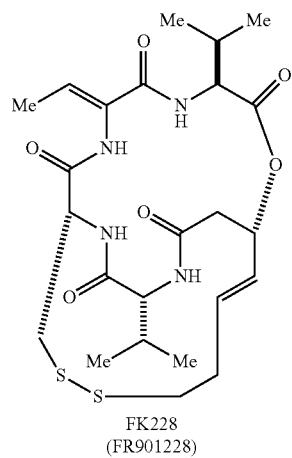

FK228
(FR901228)

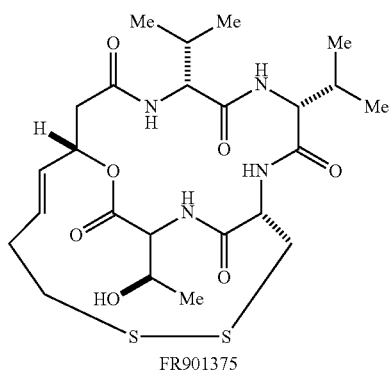

FR901375

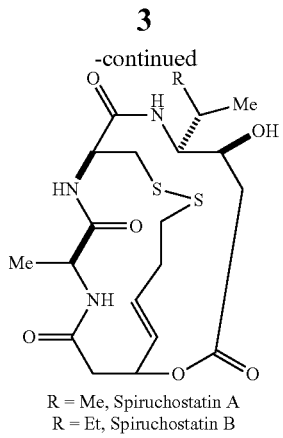

R = Me, Spiruchostatin A
R = Et, Spiruchostatin B

The histone deacetylase enzymes are zinc metalloenzymes that catalyze the hydrolysis of acetylated lysine residues in chromatin and, thereby, regulate transcription in eukaryotic cells (Somech, R., et al. 2004 *Cancer Treat. Rev.* 30:461; Miller, T. A., et al. 2003 S. *J. Med. Chem.* 46:5097-5116; Moradei, O., et al. 2005 *Curr. Med. Chem.; Anti-Cancer Agents* 5:529-560; Bolden, J. E., et al. 2006 *Nat. Rev. Drug Discovery* 5:769-784). Their selective inhibition has recently become a major area of research in cancer chemotherapy (Minucci, S., et al. 2006 *Nature Rev. Cancer* 6:38-51). To date, eighteen HDACs have been identified, which are generally divided into four classes based on sequence homology to yeast counterparts (Taunton, J., et al. 1996 *Science* 272:408-411; Grozinger, C. M., et al. 1999 *Proc. Nat. Acad. Sci. USA* 96:4868-4873; Johnstone, R. W. 2002 *Nature Rev. Drug Disc.* 1:287-299). With respect to cancer therapy, there is an emerging consensus that Class I HDACs are clinically relevant, and that the undesirable toxicity associated with the first generation of HDAC inhibitors may be related to class indiscriminancy. As a result, programs have been initiated that are aimed at the synthesis and modification of peptide- and depsipeptide-based HDACi with the objective of optimizing structures for class- and even isoform-specific inhibition.

BRIEF SUMMARY OF THE INVENTION

Described herein is the derivatization of the thiazole ring in the largazole structural template, allowing the preparation of a series of new compositions of matter that are also extraordinarily potent Class I HDAC inhibitors. These largazole analogs demonstrate surprising HDAC inhibition with better selectivity. This is due to the location of the new "chemical space" is located at the rim of the HDAC active site, which greatly expands opportunities to model new compounds via crystal structures or structure activity relationships. In addition a wide range of functionality can be added at the C(5) position in question, including important chemical probes such as photo-activated cross linkers and biotin for pull-down experiments.

Biological screening shows that the phenyl-substituted inhibitor described herein is equipotent to largazole.

In one aspect, the invention provides a compound of claim Formula (I)

wherein X=O, NH, or NR, wherein R is H or lower alkyl;
Y=S, O, NH, or NR, wherein R is alkyl, aryl, arylalkyl, substituted alkyl, substituted aryl, or substituted arylalkyl;
Z=S, O, NH, or NR, wherein R is alkyl, aryl, arylalkyl, substituted alkyl, substituted aryl, or substituted arylalkyl;
$R_1$=H, alkyl, aryl, arylalkyl, substituted alkyl, substituted aryl, or substituted arylalkyl; wherein, if $R_1$ is a substituted substituent, that substituent (i.e., alkyl, aryl, or arylalkyl) is substituted with a cleavable or non-cleavable $OR_6$, $NR_6$, or $SR_6$, wherein $R_6$=folate derivative, biotin, cytokines (for example, IL-3), peptide, carbohydrate (for example, mannose), or other cancer cell surface-targeting agents, or, for $SR_6$, another molecule of the same (i.e., resulting in a homodimer);
$R_2$=H, acyl, or cleavable $SR_5$, wherein $R_5$=folate derivative, cytokines (for example, IL-3), peptide, carbohydrate (for example, mannose), or other cancer cell surface-targeting agents, or another molecule of the same (i.e., resulting in a homodimer);
$R_3$=H, alkyl, aryl, arylalkyl, substituted alkyl, substituted aryl, or substituted arylalkyl;
$R_4$=alkyl or aryl, with iso-propyl being particularly preferred;
or a pharmaceutically acceptable salt, solvate, clathrate, prodrug, or stereoisomer thereof. In the chemical compound structures provided herein, further defined substituents such as X, Y, Z, R, and the like are independently selected from the identified substituents.

The largazole analogs described herein are the first with functionality on the thiazole ring that can be utilized to make cell-specific targeting agents and other probe molecules not hitherto accessible from the natural product itself. No other known HDAC inhibitor has a readily linkable site distal from the zinc-binding arm of the drug for conjugating probes, other molecular cytotoxic "warheads", and/or delivery molecules (targeting agents as described above). The linkage of the largazole analog scaffold to the targeting agents can be either cleavable in cells (such as via disulfide linkages, esters, amides) or not readily cleavable.

In one aspect, the invention provides a compound of Formula (A)

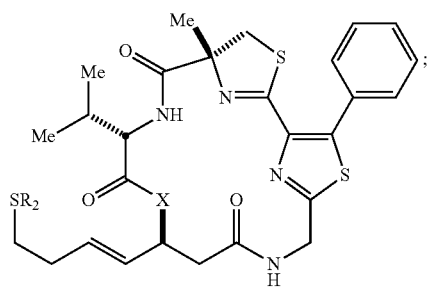

wherein X=O, NH, or NR, wherein R is H or lower alkyl; wherein R₂=H, acyl, or cleavable SR₅, wherein R₅=folate derivative, cytokines (for example, IL-3), peptide, carbohydrate (for example, mannose), or other cancer cell surface-targeting agents, or another molecule of the same (i.e., resulting in a homodimer); or a pharmaceutically acceptable salt, solvate, clathrate, prodrug, or stereoisomer thereof.

In another aspect, the invention provides a compound of Formula (B)

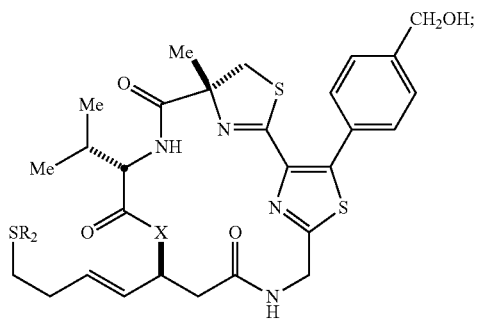

wherein X=O, NH, or NR, wherein R is H or lower alkyl; wherein R₂=H, acyl, or cleavable SR₅, wherein R₅=folate derivative, cytokines (for example, IL-3), peptide, carbohydrate (for example, mannose), or other cancer cell surface-targeting agents, or another molecule of the same (i.e., resulting in a homodimer); or a pharmaceutically acceptable salt, solvate, clathrate, prodrug, or stereoisomer thereof.

In another aspect, the invention provides a compound of Formula (C)

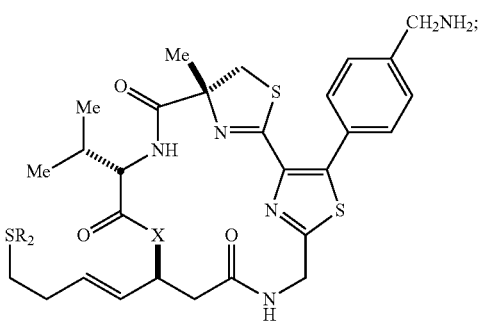

wherein X=O, NH, or NR, wherein R is H or lower alkyl; wherein R₂=H, acyl, or cleavable SR₅, wherein R₅=folate derivative, cytokines (for example, IL-3), peptide, carbohydrate (for example, mannose), or other cancer cell surface-targeting agents, or another molecule of the same (i.e., resulting in a homodimer); or a pharmaceutically acceptable salt, solvate, clathrate, prodrug, or stereoisomer thereof.

In another aspect, the invention provides a compound of Formula (D)

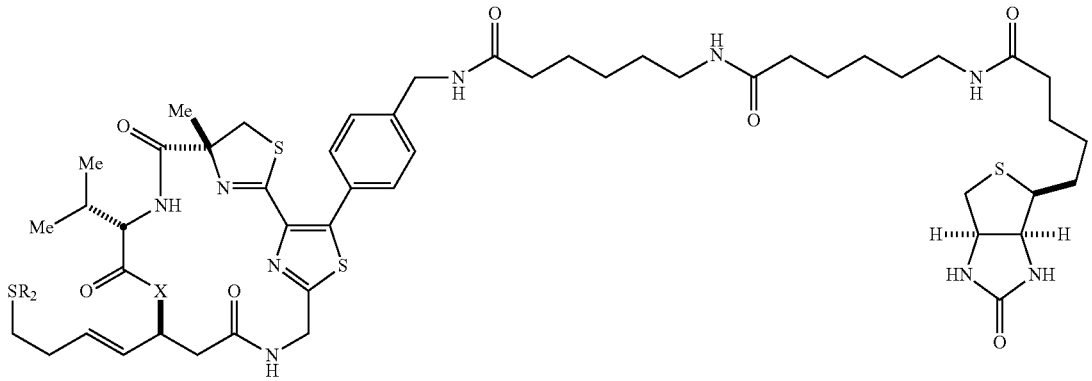

wherein X=O, NH, or NR, wherein R is H or lower alkyl; wherein R₂=H, acyl, or cleavable SR₅, wherein R₅=folate derivative, cytokines (for example, IL-3), peptide, carbohydrate (for example, mannose), or other cancer cell surface-targeting agents, or another molecule of the same (i.e., resulting in a homodimer); or a pharmaceutically acceptable salt, solvate, clathrate, prodrug, or stereoisomer thereof.

In one aspect, the invention provides a method for treating cancer in a subject, comprising administering to the subject a therapeutically effective amount of any one of the compounds described herein. In one embodiment, the method further comprises treating said subject with an additional form of therapy for cancer. In another embodiment, the method further comprises obtaining the compound. In yet another embodiment, the subject is human.

In another aspect, the invention provides a method for treating a blood disorder in a subject, comprising administering to the subject a therapeutically effective amount of any one of the compounds described herein. In one embodiment, the blood disorder is at least one of a hemoglobinopathy or a thalassemia. In another embodiment, the method further comprises treating said subject with an additional form of therapy for said blood disorder. In still another embodiment, the method further comprises obtaining the compound. In yet another embodiment, the subject is human.

In one aspect, the invention provides a pharmaceutical composition comprising a therapeutically effective amount of any one of the compounds described herein and at least one pharmaceutically acceptable excipient for treating cancer in a subject. In one embodiment, the subject is human.

In another aspect, the invention provides a pharmaceutical composition comprising a therapeutically effective amount of any one of the compounds described herein and at least one pharmaceutically acceptable excipient for treating a blood disorder in a subject. In another embodiment, the blood disorder is at least one of a hemoglobinopathy or a thalassemia. In still another embodiment, the subject is human.

In one aspect, the invention provides a composition comprising a radiolabelled compound of Formula (I), (A), (B), (C), or (D), or a pharmaceutically acceptable salt, solvate, clathrate, prodrug, or stereoisomer thereof.

In one aspect, the invention provides a method for treating an auto-immune disease in a subject, comprising administering to the subject a therapeutically effective amount of any one of the compounds described herein. In one embodiment, the autoimmune disease is selected from rheumatoid arthritis, lupus, multiple sclerosis, and inflammatory bowel disease. In another embodiment, the method further comprises treating said subject with an additional form of therapy for said auto-immune disease. In still another embodiment, the method further comprises obtaining the compound. In yet another embodiment, the subject is human.

In one aspect, the invention provides a pharmaceutical composition comprising a therapeutically effective amount of any one of the compounds described herein and at least one pharmaceutically acceptable excipient for treating an auto-immune disease in a subject. In one embodiment, the autoimmune disease is selected from rheumatoid arthritis, lupus, multiple sclerosis, and inflammatory bowel disease. In another embodiment, the subject is human.

In one aspect, the invention provides a method for treating Alzheimer's Disease in a subject, comprising administering to the subject a therapeutically effective amount of any one of the compounds described herein. In one embodiment, the method further comprises treating said subject with an additional form of therapy for Alzheimer's Disease. In still another embodiment, the method further comprises obtaining the compound. In yet another embodiment, the subject is human.

In one aspect, the invention provides a pharmaceutical composition comprising a therapeutically effective amount of any one of the compounds described herein and at least one pharmaceutically acceptable excipient for treating Alzheimer's Disease in a subject. In one embodiment, the subject is human.

In an additional aspect, a method for treating cancer in a subject, comprising administering to the subject a compound of the invention is provided.

The method may further comprise treating said subject with an additional form of therapy for cancer. The method may further comprise obtaining the compound. The subject may be human.

In yet another aspect, a method for treating a blood disorder in a subject, comprising administering to the subject a compound of the invention is provided. The blood disorder may be at least one of a hemoglobinopathy or a thalassemia. The method may further comprise treating said subject with an additional form of therapy for said blood disorder. The method may further comprise obtaining the compound. The subject may be human.

In still another aspect, a method for treating an auto-immune disease in a subject, comprising administering to the subject a compound of the invention is provided. The method may further comprise treating the subject with an additional form of therapy for the auto-immune disease. The method may further comprise obtaining the compound. The subject may be human.

In still another aspect, a method for treating Alzheimer's Disease in a subject, comprising administering to the subject a compound of the invention is provided. The method may further comprise treating said subject with an additional form of therapy for Alzheimer's Disease. The method may further comprise obtaining the compound. The subject may be human.

In yet another aspect, a pharmaceutical composition comprising a compound of the invention and at least one pharmaceutically acceptable excipient for treating cancer in a subject is provided.

In still another embodiment, a pharmaceutical composition comprising a compound of the invention and at least one pharmaceutically acceptable excipient for treating a blood disorder in a subject is provided. The blood disorder may be at least one of a hemoglobinopathy or a thalassemia.

In still another embodiment, a pharmaceutical composition comprising a compound of the invention and at least one pharmaceutically acceptable excipient for treating an auto-immune disease in a subject is provided.

In yet another embodiment, a pharmaceutical composition comprising a compound of the invention and at least one pharmaceutically acceptable excipient for treating Alzheimer's Disease in a subject is provided.

Other aspects of the invention are described in or are obvious from the following disclosure and are within the ambit of the invention.

BRIEF DESCRIPTION OF THE FIGURES

The following Detailed Description of the Invention, given by way of Examples, but not intended to limit the invention to specific embodiments described, may be understood in conjunction with the accompanying figures, in which:

FIG. 2 displays a table providing the results of biochemical profiling of largazole analogues in terms of $IC_{50}$ (nM).

FIG. 8A shows a schematic outline of a haploid genetic screen in KBM7 cells. FIG. 8B shows enrichment results of genetrap insertion as a Circos plot. Every gene with at least one insertion is depicted as a circle, the location of which is based on chromosomal position. Circle size correlates with the number of insertions mapped for that gene. P-values decrease from inside-to-outside. Haploid genetic screens usually yield very few, but very high-confidence candidate genes. FIG. 8C shows a schematic outline of a genome-wide CRISPR screen. FIG. 8D shows a schematic depiction of enrichment results for DOT1L inhibition in MV4;11 as a Circos plot. Each gene represented in the library is depicted as a circle, based on chromosomal position. Circle size correlates with the number of sgRNAs significantly enriched (p<0.001). P-values for enrichments of sgRNAs targeting a certain gene are computed using the RIGER algorithm.

DETAILED DESCRIPTION OF THE INVENTION

I. Definitions

Figure 1A:
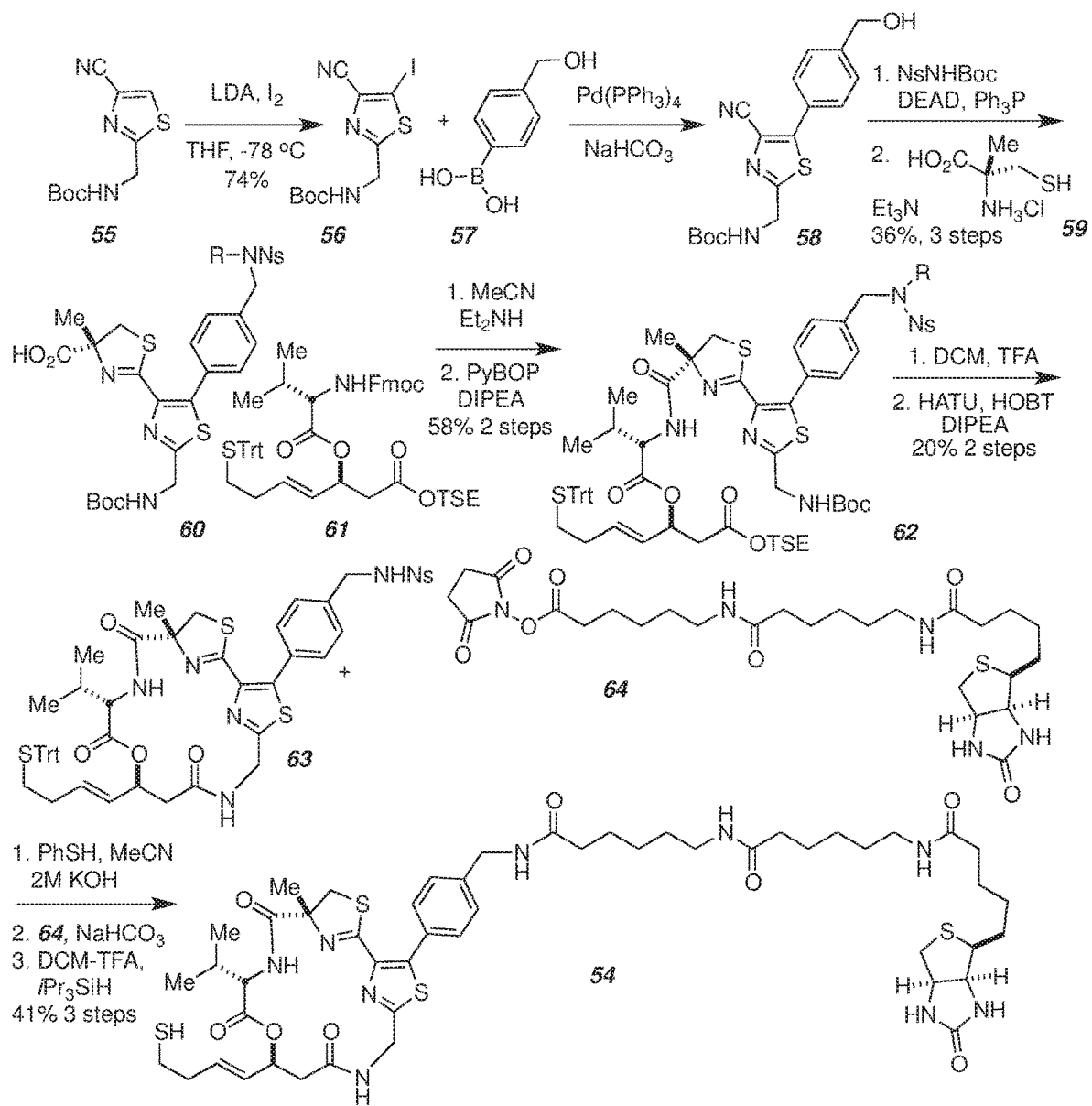
FIG. 1A shows the synthetic scheme and structure of Largazole-Biotin 54.
Figure 1B:
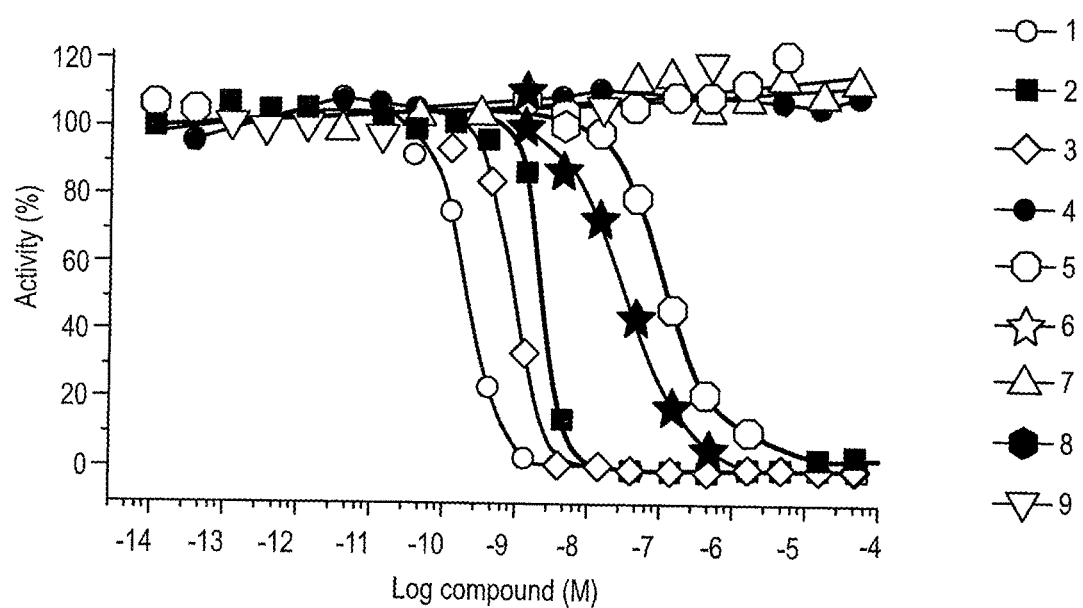
FIG. 1B shows the biochemical selectivity of Largazole-Biotin, which compares favorably to free Largazole-thiol.
Figure 1C:
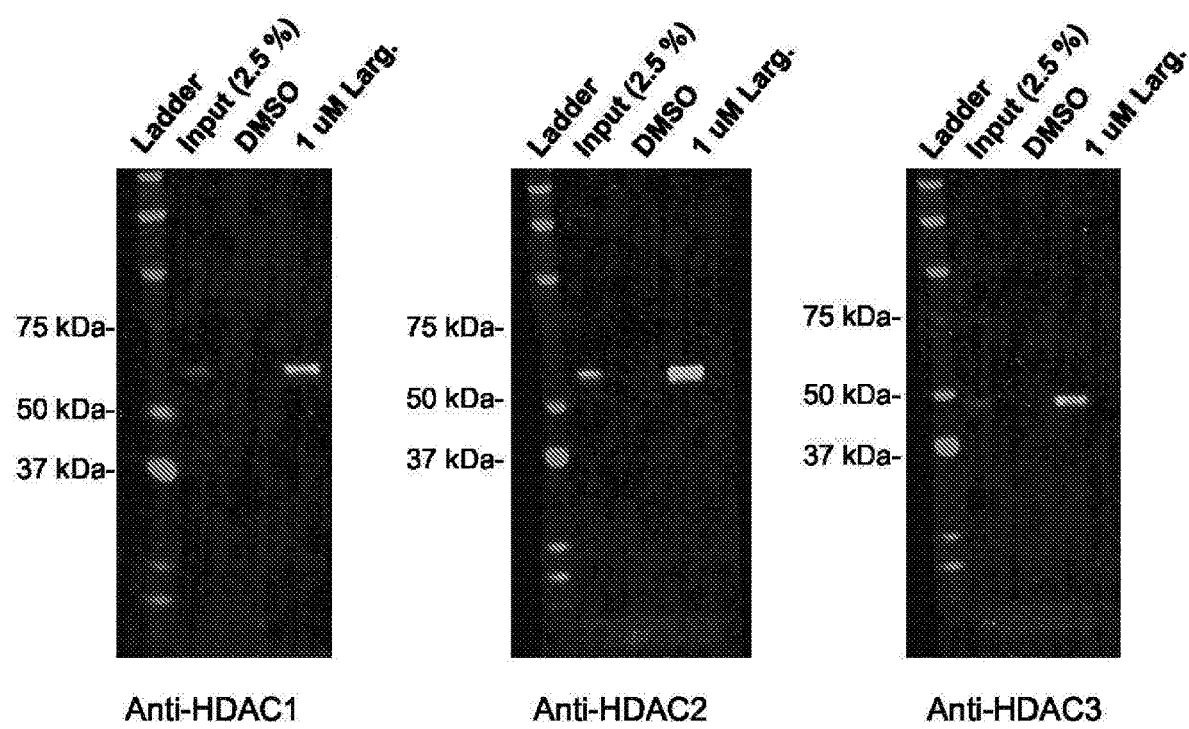
FIG. 1C shows the affinity precipitation of HDACs1, 2 & 3 by Largazole-Biotin (54), by immunoblot. 1 µM Largazole-Btn (54) in 200 µL of HeLa Nuclear Extract (~200 gig) mg of streptavidin beads added after 16 hr incubation with compound.

As used herein, the term "compound(s) of the invention" and similar terms refer to a compound of formula (I) or a pharmaceutically acceptable salt, solvate, clathrate, or prodrug thereof.

In the compound of Formula (I), the designation of one line parallel to a dotted line represents an optional double bond. When present, the double bond may be either is cis- or trans-configuration.

As used herein, "lower alkyl" or "lower alkyl moieties" contain from 1-12 carbon atoms, "lower aryl" or "lower aryl moieties" contain from 6-12 carbon atoms, and "lower arylalkyl" or "lower arylalkyl moieties" contain from 7-12 carbon atoms. In a preferred embodiment, lower alkyl refers to a $C_{1-7}$alkyl, lower aryl to a $C_{6-10}$aryl, and lower arylalkyl to a $C_{7-11}$aralkyl. Included are substituted derivatives of lower chain alkyl, aryl and arylalkyl moieties, wherein the substituent is selected from (but are not limited to) one or more of the following chemical moieties: —OH, —$OR_7$, —COOH, —$COOR_7$, —$CONH_2$, —$NH_2$, —$NHR_7$, —$NR_7R_7$, —SH, —$SR_7$, —$SO_2R_7$, —$SO_2H$, —$SOR_7$, —$PO_3R_7$, —$OPO_3R_7$, and halogen (including F, Cl, Br and I), wherein each occurrence of $R_7$ is independently selected from a lower chain alkyl, aryl or arylalkyl moiety. Moreover, cyclic lower chain alkyl, aryl and arylalkyl moieties of the invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole.

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 *J. Pharm. Sci.* 66:1-19). Prodrugs can typically be prepared using well-known methods, such as those described in Burger's Medicinal Chemistry and Drug Discovery (1995, Manfred E. Wolff ed., 5$^{th}$ ed. 172-178, 931-932).

It will be noted that the structure of some of the compounds of this invention includes asymmetric carbon atoms, and thus may exist as racemic mixtures or as isolated isomeric forms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Furthermore, some of the crystalline forms of the compounds of Formula (I) may exist as polymorphs, which are included in the present invention. In addition, some of the compounds of Formula (I) may also form solvates with water or other organic solvents. Such solvates are similarly included within the scope of this invention.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Cancer is a term used for diseases in which abnormal cells divide without control and are able to invade other tissues. There are more than 100 different types of cancer. Most cancers are named for the organ or type of cell in which they start—for example, cancer that begins in the colon is called colon cancer, cancer that begins in basal cells of the skin is called basal cell carcinoma. The main categories of cancer include carcinomas, sarcomas, leukemias, lymphomas and myelomas, and central nervous system cancers. Some common cancer types include, but are not limited to, bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer. In a preferred embodiment, the cancers contemplated for treatment herein include cutaneous T-cell lymphoma, non-Hodgkin's and Hodgkin's lymphoma, pancreatic cancer, and ovarian cancer.

Hemoglobinopathies and thalassemias can both be characterized as "blood disorders". Blood disorders include disorders that can be treated, prevented, or otherwise ameliorated by the administration of a compound of the invention. A blood disorder is any disorder of the blood and blood-forming organs. The term blood disorder includes nutritional anemias (e.g., iron deficiency anemia, sideropenic dysphasia, Plummer-Vinson syndrome, vitamin B12 deficiency anemia, vitamin B12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia, δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemoglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythoblastopenia), other aplastic anemias, such as constitutional aplastic anemia and Fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymphocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of ordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

The compounds of the invention that are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

Thus, as used herein, the term "pharmaceutically acceptable salt," is a salt formed from an acid and a basic group of a compound of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "subject" as used herein refers to a vertebrate, preferably a mammal, more preferably a primate, still more preferably a human. Mammals include, without limitation, humans, primates, wild animals, feral animals, farm animals, sports animals, and pets.

The term "therapeutically effective amount" as used herein refers to an amount sufficient to effect a beneficial or desired clinical result upon treatment. Specifically, the term "therapeutically effective amount" means an amount of a compound of this invention sufficient to measurably (i) reduce or inhibit the growth of transformed (cancer) cells in a relevant in vitro assay or cause a measurable improvement in an animal model of cancer and/or (ii) induce expression of fetal hemoglobin in a relevant in vitro assay or cause a measurable improvement in an animal model of a hemoglobinopathy and/or thalassemia, for example, a sickle cell disease. Alternatively, a "therapeutically effective amount" is an amount of a compound of this invention sufficient to confer a therapeutic or prophylactic effect on the treated subject against (i) cancer and/or (ii) a hemoglobinopathy and/or thalassemia. Therapeutically effective amounts will vary, as recognized by those skilled in the art, depending on the specific disease treated, the route of administration, the excipient selected, and the possibility of combination therapy.

Physiological effects that can be measured to determine the therapeutically effective amount include, without limitation, substrate protein hyperacetylation (histone, tubulin, hsp90, p53, STAT, etc.), gene induction (fetal hemoglobin, spinal muscle atrophy gene), impaired protein trafficking, improved neuronal vesicle trafficking, induction of apoptosis, cell cycle arrest, and induction of p21.

Relevant assays to measure such effects include, without limitation, Western (immuno)blot, RT-PCR, expression profile by microarray or other technology, high-content immunofluorescence, cytoblot, biochemical inhibition of HDAC proteins, alterations in chromatin structure by ChIP, and alterations in histone and/or other target protein modification by mass spectrometry.

The term "obtaining" as in "obtaining the compound" is intended to include purchasing, synthesizing or otherwise acquiring the compound (or indicated substance or material).

The terms "comprises", "comprising", are intended to have the broad meaning ascribed to them in U.S. Patent Law and can mean "includes", "including" and the like.

The invention can be understood more fully by reference to the following detailed description and illustrative examples, which are intended to exemplify non-limiting embodiments of the invention.

II. Embodiments of the Invention

Compounds of the Invention

The compounds of the invention are defined herein by their chemical structures and/or chemical names. The compounds of the invention are generally named according to the IUPAC or CAS nomenclature system. Abbreviations that are well known to one of ordinary skill in the art may be used. When a compound is referred to by both a chemical structure and a chemical name, and the chemical structure and chemical name conflict, the chemical structure is determinative of the compound's identity.

A dotted line parallel to a solid line in a chemical structure indicates the optional presence of a double bond. Two dotted lines parallel to solid lines adjacent to one another indicates the optional presence of a double bond in either, but not both, of the two positions. Either E (trans) or Z (cis) geometry is indicated. In fact, all alkenes contemplated herein can exist as either E (trans) or Z (cis) geometry.

When administered to a subject, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least about 80%, preferably at least about 90%, more preferably at least about 95% and even more preferably at least about 98%, of a single compound of the invention by weight of the isolate.

Radioactive compounds have a long history of use in the discovery of new drugs. The compounds of the invention all have the potential to be easily radiolabeled and can be used to discover other new agents that (i) reduce or inhibit the growth of transformed (cancer) cells and/or (ii) induce fetal hemoglobin expression. For example, radioactive compounds of the invention can be utilized to validate, optimize, and standardize bioassays used for discovery of other compounds that (i) reduce or inhibit the growth of transformed (cancer) cells and/or (ii) induce fetal hemoglobin expression. Likewise, radioactive compounds of the invention can be utilized as a benchmark to discover compounds that show improved activity in bioassays that (i) reduce or inhibit the growth of transformed (cancer) cells and/or (ii) induce fetal hemoglobin expression.

Preparation of Compounds of the Invention

The compounds of the invention can be prepared in an efficient, cost-effective manner. Syntheses of previous largazole analog compounds are described in U.S. Pat. No. 8,217,076, which is herein incorporated by reference. Specific syntheses are described in the examples.

Methods of Treatment

In one embodiment of the invention, a therapeutically effective amount of a compound of formula (I) or a pharmaceutically acceptable salt, solvate, clathrate, and prodrug thereof, or a pharmaceutical composition comprising a compound of formula (I) or a pharmaceutically acceptable salt, solvate, clathrate, and prodrug thereof, is administered to a patient in need of treatment of cancer. In another embodiment of the invention, a therapeutically effective amount of a compound of formula (I) or a pharmaceutically acceptable salt, solvate, clathrate, and prodrug thereof, or a pharmaceutical composition comprising a compound of formula (I) or a pharmaceutically acceptable salt, solvate, clathrate, and prodrug thereof, is administered to a patient in need of treatment of a blood disorder. Other conditions, diseases and disorders that would benefit from such uses are known to those of skill in the art.

The compounds of the invention are also contemplated for the treatment of inflammatory disorders (for example, of the skin, joints, etc.), immune tolerance, transplantation rejection, graft-versus-host disease, and the like.

The compounds of the invention are also contemplated for the treatment of auto-immune disease in a subject. Autoimmune diseases include, without limitation, rheumatoid arthritis, lupus, multiple sclerosis, and inflammatory bowel disease.

The compounds of the invention are also contemplated for the treatment of Alzheimer's Disease in a subject.

Responsiveness of the disease to compounds and compositions of the invention can be measured directly by comparison against conventional drugs (for example, for cancer, chemotherapeutics; for certain blood disorders, FK228 or SAHA), or can be inferred based on an understanding of disease etiology and progression. For example, there are a number of fetal hemoglobin expression assay systems that are widely accepted in the art as predictive of in vivo effects. Thus, the showing that a compound of this invention induces fetal hemoglobin expression in these assays is evidence of the clinical utility of these for treating a hemoglobinopathy and/or a thalassemia, i.e., a blood disorder.

In one embodiment of the invention, "treatment" or "treating" refers to an amelioration of cancer or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of cancer, either physically, e.g., stabilization of a discernible symptom, physiologically, e.g., stabilization of a physical parameter, or both. In yet another embodiment, "treatment" or "treating" refers to delaying the onset of cancer or symptoms thereof.

In another embodiment of the invention, "treatment" or "treating" refers to an amelioration of a hemoglobinopathy and/or a thalassemia, i.e., a blood disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a hemoglobinopathy and/or a thalassemia, i.e., a blood disorder, either physically, e.g., stabilization of a discernible symptom, physiologically, e.g., stabilization of a physical parameter, or both. In yet another embodiment, "treatment" or "treating" refers to delaying the onset of a hemoglobinopathy and/or a thalassemia, i.e., a blood disorder, or symptoms thereof.

In one embodiment of the invention, "treatment" or "treating" refers to an amelioration of an auto-immune disease or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of the auto-immune disease, either physically, e.g., stabilization of a discernible symptom, physiologically, e.g., stabilization of a physical parameter, or both. In yet another embodiment, "treatment" or "treating" refers to delaying the onset of the auto-immune disease or symptoms thereof.

The compounds of formula (I) or pharmaceutically acceptable salts, solvates, clathrates, and prodrugs thereof can be assayed in vitro or in vivo, for the desired therapeutic or prophylactic activity, prior to use in humans. For example, animal model systems can be used to demonstrate the safety and efficacy of compounds of this invention.

Without wishing to be bound by theory, it is believed that the compounds and compositions of this invention induce gene expression, for example, BDNF (for psychiatric disease), HbF, SMA, p53, and/or p21 expression and, as a result, may be used to treat or prevent cancer. Further without wishing to be bound by theory, it is believed that the compounds and compositions of this invention induce gene expression, for example, fetal hemoglobin expression and, as a result, may be used to treat or prevent a hemoglobinopathy and/or a thalassemia, i.e., a blood disorder. It should be noted, however, that the compounds might act by a secondary or a different activity, such as, without limitation, delaying the normally fixed fetal-to-adult globin gene switch or stimulating hematopoiesis, erythropoiesis, myelopoiesis and/or neutrophil production.

Pharmaceutical Compositions

In one embodiment, pharmaceutical compositions and dosage forms of the invention comprise a compound of formula (I) or a pharmaceutically acceptable prodrug, salt, solvate, or clathrate thereof, in relative amounts and formulated in such a way that a given pharmaceutical composition or dosage form reduces or inhibits the growth of transformed (cancer) cells. In another embodiment of the invention, such pharmaceutical compositions and dosage forms comprise one or more additional active agents such as chemotherapeutic agents known in the art.

In another embodiment, pharmaceutical compositions and dosage forms of the invention comprise a compound of formula (I) or a pharmaceutically acceptable prodrug, salt, solvate, or clathrate thereof, in relative amounts and formulated in such a way that a given pharmaceutical composition or dosage form induces the expression of fetal hemoglobin. In another embodiment of the invention, such pharmaceutical compositions and dosage forms comprise one or more additional active agents.

The compounds of the invention and pharmaceutically acceptable salts thereof can be administered via, for example, the oral, parenteral, topical, rectal, subcutaneous, transdermal, and/or pulmonary (inhaled) routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

In one embodiment, the pharmaceutical compositions of the invention may be administered alone or in combination with other known compositions for treating cancer in a subject, e.g., a mammal. Preferred mammals include cats, dogs, pigs, rats, mice, monkeys, chimpanzees, baboons and humans. In one embodiment, the subject is suffering from cancer. In another embodiment, the subject is at risk of suffering from cancer.

In another embodiment, the pharmaceutical compositions of the invention may be administered alone or in combination with other known compositions for treating blood disorders in a subject, e.g., a mammal. Preferred mammals include cats, dogs, pigs, rats, mice, monkeys, chimpanzees, baboons and humans. In one embodiment, the subject is suffering from a blood disorder. In another embodiment, the subject is at risk of suffering from a blood disorder.

The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating cancer or blood disorders can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

It will also be understood that normal, conventionally known precautions will be taken regarding the administration of the compounds of the invention generally to ensure their efficacy under normal use circumstances. Especially when employed for therapeutic treatment of humans and animals in vivo, the practitioner should take all sensible precautions to avoid conventionally known contradictions and toxic effects.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art, e.g., Remington's Pharmaceutical Sciences (1990) 18th ed., Mack Publishing, Eastern Pa.

The invention further encompasses pharmaceutical compositions and dosage forms that comprise one or more compounds that reduce the rate by which the compound of the invention will decompose. Such compounds, which are referred to herein as "stabilizer" include, but are not limited to, antioxidants such as ascorbic acid, pH buffers, or salt buffers.

The interrelationship of dosages for animals and humans (based on milligrams per meter squared of body surface) is described in Freireich, et al. 1966 *Cancer Chemother Rep* 50: 219. Body surface area may be approximately determined from height and weight of the patient, e.g., Scientific Tables, Geigy Pharmaceuticals, Ardley, N.Y., 1970, 537.

Like the amounts and types of excipients, the amount of the compound of the invention in a dosage form may differ depending on factors such as, but not limited to, the route by which it is to be administered to subjects. It is within the skill of the art to determine the appropriate dose and dosage form for a given patient.

Furthermore, the invention also pertains to the use of a compound of the invention for the preparation of a medicament. In one embodiment of the invention, the medicament may include a pharmaceutically acceptable carrier and the compound is an effective amount, e.g., an effective amount to treat cancer. In another embodiment of the invention, the medicament may include a pharmaceutically acceptable carrier and the compound is an effective amount, e.g., an effective amount to treat a blood disorder.

Kits

In one aspect, the invention provides kits comprising a unit dosage form of an effective amount of a compound of formula (I) or a pharmaceutically acceptable prodrug, salt, solvate, hydrate, or clathrate thereof, and a device that can be used to administer the compound. Examples of such devices include, but are not limited to, syringes, drip bags, patches, and inhalers.

Kits of the invention can further comprise pharmaceutically acceptable vehicles. For example, if a compound of the invention is provided in a solid form that must be reconstituted for parenteral administration, the kit can comprise a sealed container of a suitable vehicle in which the compound can be dissolved to form a particulate-free sterile solution that is suitable for parenteral administration.

Combination Therapy

The herein-described methods for treatment in a subject can further comprise administering to the subject being administered a compound of this invention, an effective amount of one or more other therapeutic agents. In one embodiment of the invention where another therapeutic agent is administered to a subject, the effective amount of the compound of the invention is less than its effective amount would be where the other therapeutic agent is not administered. In another embodiment, the effective amount of the other therapeutic agent is less than its effective amount would be where the compound of the invention is not administered.

In some aspects described herein, the method includes an additional therapeutic modality. For example, the additional therapeutic modality is radiation therapy or a cytotoxic chemotherapy agent, such as an anti-metabolite (e.g., 5-FU, with leucovorin), irinotecan, (or other topoisomerase inhibitor), doxorubicin, or any combination all of these agents, including administration of all of these agents.

The methods can further include the step of monitoring the subject, e.g., for a reduction in one or more of: a reduction in tumor size; reduction in cancer markers, e.g., levels of cancer specific antigen; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the compound of Formula (I) or for additional treatment with additional agents. Generally, a decrease in or stabilization of one or more of the parameters described above is indicative of the improved condition of the subject. Information about the monitoring can be recorded, e.g., in electronic or digital form.

The treatment methods disclosed herein can be used in combination with one or more additional treatment modalities, including, but not limited to: surgery; radiation therapy, and chemotherapy.

With reference to the methods disclosed herein, the term "combination" refers to the use of one or more additional agents or therapies to treat the same patient, wherein the use or action of the agents or therapies overlap in time. The additional agents or therapies can be administered at the same time as the compound of Formula (I) is administered, or sequentially in any order. Sequential administrations are administrations that are given at different times. The time between administration of the one agent and another agent can be minutes, hours, days, or weeks.

The additional agent or therapy can also be another anti-cancer agent or therapy. Nonlimiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., irinotecan, topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and depsipeptide (also referred to as FK228 or Romidepsin); biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl)propionanilide.

A combination therapy can include administering an agent that reduces the side effects of other therapies. The agent can be an agent that reduces the side effects of anti-cancer treatments. A combinational therapy can also include administering an agent that reduces the frequency of administration of other therapies. The agent can be an agent that decreases growth of tumor after the anti-cancer effects of other therapies have decreased.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation. For example, the compounds of the invention may be administered to the subject for treatment of a hemoglobinopathy and/or a thalassemia, i.e., a blood disorder, in combination with one or more cytokines. In one embodiment, the cytokine is selected from the group consisting of IL-3, GM-CSF, G-CSF, stem cell factor (SCF) and IL-6.

Further Contemplated Embodiments

Limiting the utility of known HDAC inhibitors more broadly in cancer and in non-malignant conditions has been (1) on-target toxicity and (2) a rather limited understanding of cancer cell sensitivity and resistance. Having established a platform capability to the chemical optimization of largazole, the mechanistic effects of natural product HDAC inhibitors on chromatin structure and function can be elucidated. The toxicity of Class I HDACs (1, 2, 3, and 8) represents a significant barrier to extending the therapeutic utility of such compounds beyond CTCL. Chemical approaches are directed at the targeted delivery of largazole-derived prototype therapeutics to leukemia and lymphoma cells.

It is hypothesized that largazole localizes genome-wide to sites of recruitment of HDACs1-3 containing repressive complexes, leading to enzyme inhibition and local hyperacetylation. Hyperacetylation subsequently spreads throughout bulk chromatin, causing (i) redistribution of bromodomain-containing transcriptional complexes, (ii) increased chromatin accessibility, and (iii) de-regulation of coordinated transcriptional elongation. Thus, conjugation of natural product-inspired HDAC inhibitors to cancer targeting small molecules and biomolecules is likely to enhance tumor-specific cytotoxicity, as will improving isoform-specific inhibition. Furthermore, it is likely that genetic determinants of resistance to epigenetic HDAC inhibitor therapy will map to chromatin complexes involved in transactivation and remodeling.

a) Establishment of the mechanism and site of largazole anti-cancer activity. The effect of largazole on chromatin structure and function is determined using genome-wide, integrated epigenomic analyses. A novel, retrievable derivative of Largazole allows the elucidation of engaged protein complexes by mass spectroscopy and the spatial localization of largazole within chromatin genome-wide by Chem-Seq.

b) Expansion of the cancer-specific therapeutic index of largazole through small molecule and biomolecule conjugation. To expand the therapeutic index of largazole, caged, releasable conjugates are prepared and characterized. Folate conjugation and cytokine bioconjugation (IL3 (interleukin 3)) allow selective targeting of leukemia and lymphoma, in vitro and in vivo.

c) Identification of genetic mechanisms of resistance to epigenetic HDAC inhibitor therapy. In an effort to better understand the mechanism of drug action, to anticipate clinical resistance to largazole therapy, and to explain clinical resistance to known FDA-approved HDAC inhibitors, the genetic determinants of epigenetic HDAC inhibitor resistance are elucidated using haploid genetic screens and CRISPR resistance selections.

d) Realization of next-generation macrocyclic HDAC inhibitors with improved isoform selectivity. Massively parallel synthesis and selection of RNA-encoded macrocycles are biased for HDAC activity with largazole-like pharmacophores and screened for isoform-specific inhibition. Selective compounds are resynthesized, characterized biochemically, and studied in models of cancer.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description and the examples that follow, one skilled in the art can easily ascertain the essential characteristics of the present invention, and without departing from the spirit and scope thereof, can make various changes and modifications of the invention to adapt it to various usages and conditions. For example, the compounds of the invention may be used as research tools (for example, to isolate new targets for performing drug discovery). The compounds may, for instance, be radiolabelled for imaging tissue or organs or be used to form bioconjugates for affinity assays. These and other uses and embodiments of the compounds and compositions of this invention will be apparent to those of ordinary skill in the art.

The disclosure also encompasses all possible permutations of the claim set, as if they were multiple dependent claims.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described was chosen and described in order to best explain the principles of the invention, the practical application, and to enable others of ordinary skill in the art to understand the invention for various embodiments with various modifications as are suited to the particular use contemplated.

The invention is further defined by reference to the following examples describing in detail the preparation of compounds of, the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

The following examples are provided for illustrative purposes only and are not intended to limit the scope of the invention.

General Experimental Methods

Unless otherwise noted, all reactions were run under an argon atmosphere in flame or oven dried glassware. Reactions were monitored using thin layer silica gel chromatography (TLC) using 0.25 mm silica gel 60F plates with fluorescent indicator (Merck). Plates were visualized by treatment with phosphomolybdic acid stain with gentle heating. Products were purified via column chromatography using the solvent system(s) indicated. Silica gel 60, 230-400 mesh (Sorbent Technologies). Tetrahydrofuran (THF), dichloromethane ($CH_2Cl_2$), acetonitrile ($CH_3CN$), triethylamine ($Et_3N$), toluene, diethyl ether ($Et_2O$), and N,N-dimethylformamide (DMF) were passed through an alumina drying column (Solv-Tek Inc.) using argon pressure. Melting points were determined in open-ended capillaries and are uncorrected. $^1H$ NMR and $^{13}C$ NMR spectra were recorded on Varian 300, 400, or 500 MHz NMR spectrometers. Chemical shifts are reported in ppm relative to $CHCl_3$ at $\delta=7.27$ ($^1H$ NMR) and $\delta=77.23$ ($^{13}C$ NMR) or tetramethylsilane (TMS) $\delta=0.00$, where noted. Mass spectra were obtained on Fisions VG Autospec. Optical rotations were collected at 589 nm on a Rudolph Research Automatic Polarimeter Autopol III.

Example 1. Establishment of the Mechanism and Site of Largazole Anti-Cancer Activity Despite extensive literature over a decade of research, the genome-wide effects of HDAC inhibitors on chromatin structure and function are unknown. It is hypothesized that Class I HDAC inhibitors, such as largazole, engage chromatin at sites of HDAC-containing repressive complexes, leading to local and then global histone hyperacetylation. Hyperacetylation of chromatin redistributes transcriptional complexes containing bromodomains (acetyl-lysine recognition modules), thus decreasing their effective molarity and deregulating transcriptional initiation and elongation at growth and survival genes. Using integrative epigenomic strategies comparing largazole to FDA-approved HDAC inhibitors (SAHA & Romidepsin), the genome-wide effects of Class I HDAC inhibitors on chromatin structure and function are definitively elucidated.

Figure 3A:
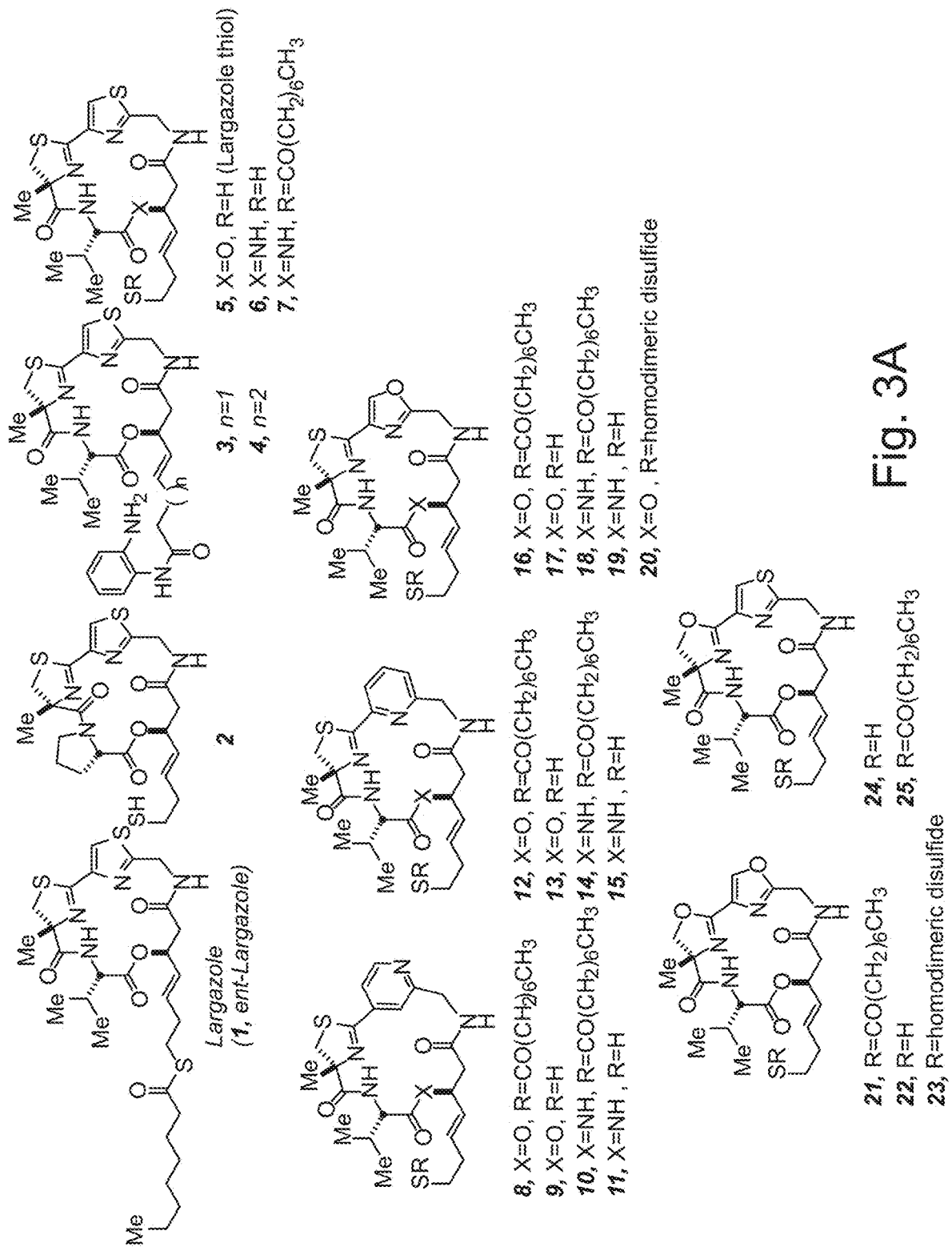
FIG. 3A provides a listing of certain largazole analogs synthesized by the inventors.
Figure 3B:
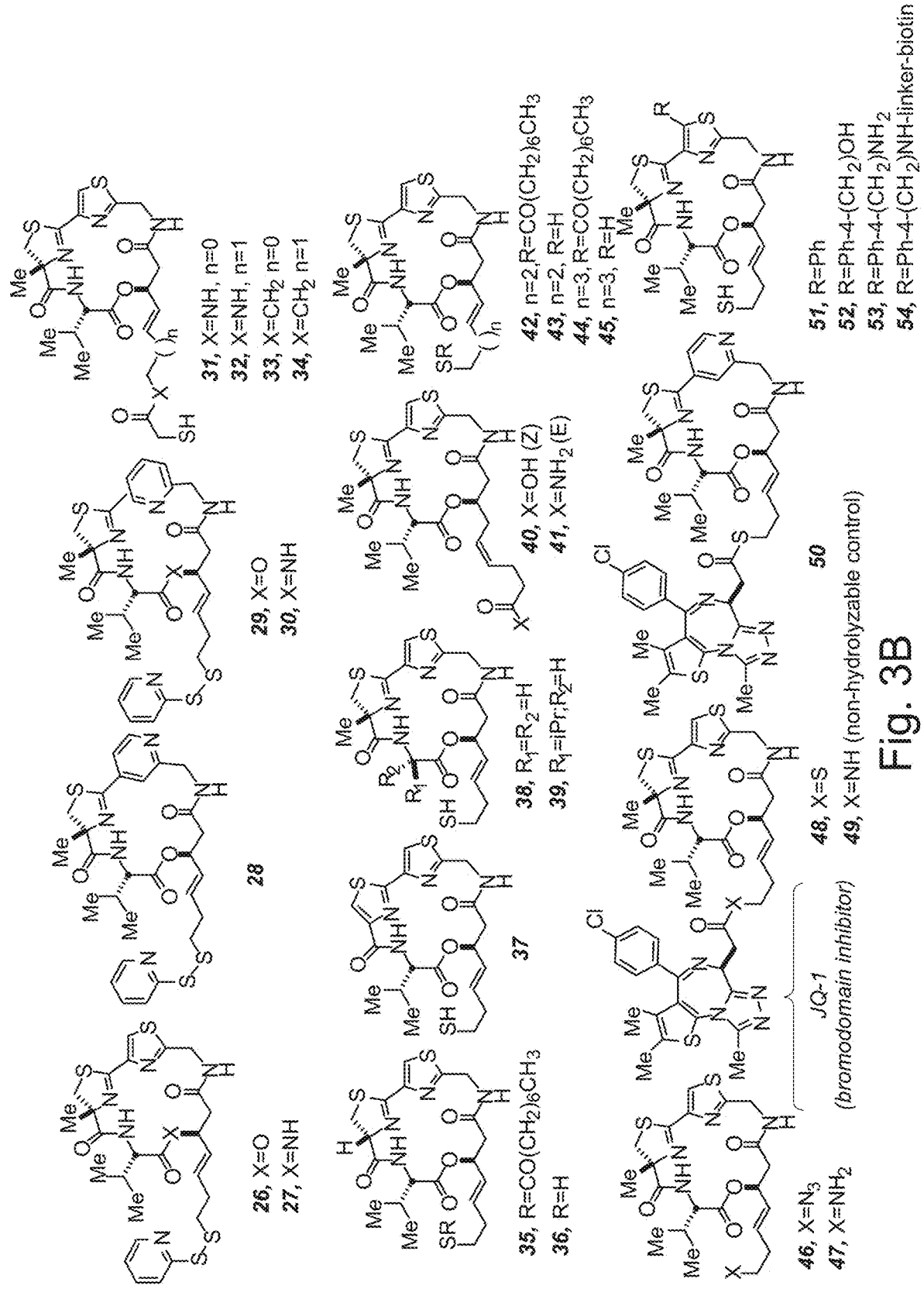
FIG. 3B provides a listing of certain largazole analogs synthesized by the inventors.

Largazole has been described as a highly potent, selective inhibitor for HDACs1-3. Subsequently, efforts have been made to understand the mode of molecular recognition of macrocyclic HDAC inhibitors and to improve the potency, selectivity, and drug-like qualities of largazole. The largazole scaffold is uniquely suited to exploit the differences in sequence and charges on the HDAC protein surface, because the rigidity of the macrocycle places functional groups in well-defined positions on the HDAC protein surface. By manipulating the structure of largazole through synthesis, analogs with increased selectivity, potency, and therapeutic value can be accessed. The inventors have synthesized over 50 largazole analogs, with some of the most recent species displayed in FIG. 3. One series involved switching the depsipeptide to a biochemically more robust peptide isostere (6/7; 10/11; 14/15; 18/19; 27; 30), manipulating the amino acid valine side chain within the macrocycle (2, 38, 39), alteration of the zinc-binding arm (3, 4, 31-34, 40, 41), and altering the cap group of the molecule (8-25, 35-37, 51-54) (Bowers, et al. 2009 *J Am Chem Soc* 131:2900-2905; Bowers, et al. 2009 *Org Lett* 11:1301-1304). Research efforts to increase the efficacy of largazole via analog development have furnished multiple new synthetic analogs with promising biochemical and biological properties. (Guerra-Bubb, et al. 2013 *Bioorg Med Chem Lett* 23:6025-6028). These consist of an oxazole substitution within the macrocycle (16-23), a thiazole to pyridyl substitution (8-15; 28-30), and derivatization of the thiazole ring (51-54). Compounds 8-15 (FIG. 3) were synthesized via similar routes based on efficient and scalable total synthesis of natural largazole (Bowers, et al. 2008 *J Am Chem Soc* 130:11219-11222). The depsipeptides were accessed via a similar pathway as the bottom fragments deployed for 8, 9, 12, and 13. The peptide precursor for compounds 10, 11, 14, and 15 were readily accessed from commercially available N-Boc(Asp)-OtBu-OH. The aryl fragment for species 12-15 were derived from 2,6-pyridinedicarboxylic acid. The thiazolidine-pyridine "N-OUT" fragment for 8-11 was similarly made from commercially available 2,4-pyridinecarboxylic acid. The fragments were joined utilizing amino acid coupling procedures similar to those described for the synthesis of the thiazoline-oxazole compounds.

Discovery Platform for Largazole-Inspired Probe Molecules

In order to facilitate an iterative design-synthesis testing cycle, a collaborative platform capability has been established to rapidly screen focused libraries of small-molecule largazole derivatives. Design of small molecules leverages high-resolution X-ray crystal structures of Largazole peptide isosteres 6, 11, and 15 bound to the Class I HDAC8 (Cole, et al. 2011 J Am Chem Soc 133:12474-12477). The side chain thiol group of each analog coordinates to the active site Zn2+ ion with nearly ideal geometry, thereby preserving the hallmark structural feature of inhibition by largazole. Synthesis of largazole derivatives has been coupled to real-time biochemical profiling for HDACi activity using a robust, miniaturized assay platform (HDAC1-9), as well as dose-ranging measurements of anti-cancer activity in hematologic and solid tumor cell lines. Data has been accumulated for >50 synthetic largazole analogs. HDAC inhibitory data for some representative species is provided in FIG. 2. Largazole shows $IC_{50}$ values below 20 nM for HDACs 1-3 and much higher values for HDACs 6 and 8. Compounds 5, 6, 9, 11, 13, and 26 display comparable or increased potency, with $IC_{50}$ values below 25 nM for HDACs 1-3. The pyridyl derivatives were also tested in the 797 and 10326 NUT midline carcinoma cell lines. Largazole peptide isostere analog 6 exhibited an $IC_{50}$ of 10 nM for both 797 and 10326, which are comparatively 10 nM and 20 nM below that of parent largazole, respectively.

Functionalization of the Thiazole Ring: A Retrievable Derivative of Largazole

In chemical biology, access to a retrievable small-molecule analogue creates a unique opportunity for mechanistic research. Indeed, the original discovery of HDAC1 and HDAC2 by Schreiber was enabled by appending the Trapoxin natural product to a solid support (Taunton, et al. 1996 Science 272:408-411; Grozinger, et al. 1999 PNAS USA 96:4868-4873). The inventors have identified a permissive site on largazole for linker substitution and have been able to prepare hitherto inaccessible analogs based on incorporating a functional handle in the cap group thiazole for new probes. As the thiazole is part of the "cap group" that protrudes away from the active site, modeling suggested that functionalization of the thiazole should not abrogate strong affinity for the target HDAC enzymes.

Preparation (FIG. 1A)

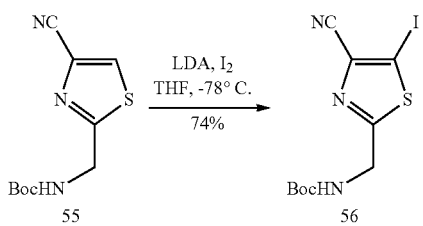 [SMILES: CC(C)(C)OC(=O)NCc1nc(C#N)cs1 ; CC(C)(C)OC(=O)NCc1nc(C#N)c(I)s1]

To a solution of thiazole 55 (85 mg, 0.36 mmol) in 7.2 mL of THF at −78° C., 1.1 mL of LDA (0.88 mmol, 0.8 M in THF) was added dropwise. (It should be noted that the addition of more than 3 equivalents of LDA would resulted in decomposition of SM). The mixture was stirred at −78° C. for 20 min, then a THF solution (1.44 mL) of 12 (365 mg, 1.44 mmol) was added. After stirred at the same temperature for 5 min, the solution was treated with saturated aq. $NH_4Cl$, diluted with ethyl acetate, separated, washed with brine, dried over $Na_2SO_4$, filtered, and concentrated under reduced pressure. The residue was purified by flash column chromatography on silica gel (0 to 9% ethyl acetate in DCM) to afford 97.4 mg (74% yield) of thiazole iodide 56 as a brown solid.

$^1$H NMR (400 MHz, $CDCl_3$) δ 5.29 (s, 1H), 4.57 (d, J=6.4 Hz, 2H), 1.46 (s, 9H); $^{13}$C NMR (100 MHz, $CDCl_3$) δ 176.5, 155.6, 134.6, 113.8, 85.0, 81.0, 42.6, 28.3; IR (neat) 3364, 2927, 1678, 1516; HRMS (ESI): m/z calcd. for $C_{10}H_{12}IN_3NaO_2S^+$ (M+Na)$^+$ 387.9587, found 387.9579.

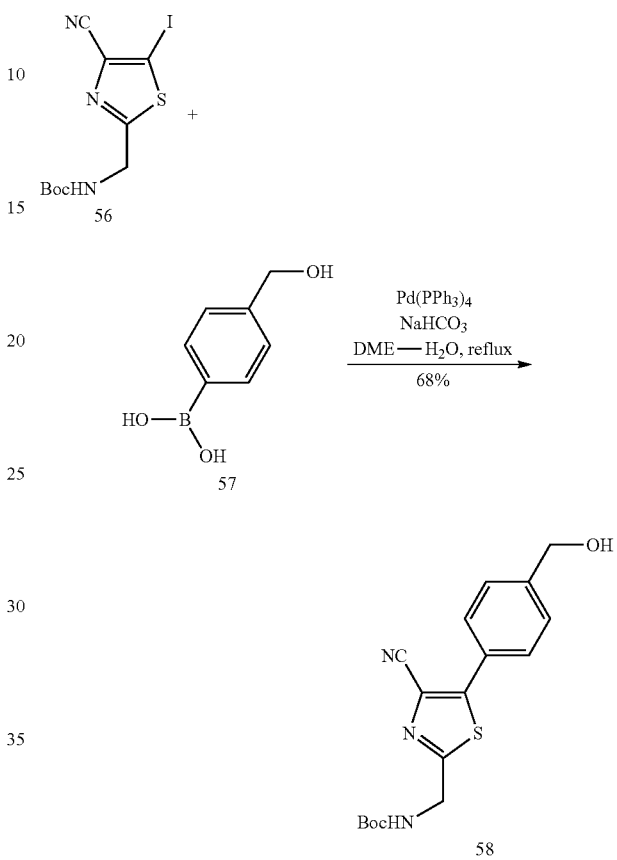

Thiazole iodide 56 (550 mg, 1.5 mmol), 4-(Hydroxymethyl)phenylboronic acid 57, (343 mg, 2.3 mmol), $NaHCO_3$ (380 mg, 4.5 mmol), $Pd(PPh_3)_4$ were combined and 16 mL of solvent ($DME/H_2O=3/1$, v/v) was added. The mixture was head to 120° C. and refluxed at that temperature for 14 hours, then cooled to room temperature and diluted with water. DME was evaporated, and the aqueous layer was extracted with ethyl acetate, separated. Organic layer was washed with brine, dried over $Na_2SO_4$, filtered, and concentrated under reduced pressure. The residue was purified by flash column chromatography on silica gel (0 to 11% ethyl acetate in DCM) to afford 67 mg (19% yield) of protonated compound 55 and 354 mg (68% yield) of desired coupling product 58 as a white solid and.

$^1$H NMR (400 MHz, $CDCl_3$) δ 7.61 (d, J=8.2 Hz, 2H), 7.41 (d, J=8.2 Hz, 2H), 5.64 (brs, 1H), 4.70 (s, 2H), 4.52 (d, J=4.6 Hz, 2H), 2.81 (brs, 1H), 1.45 (s, 9H); $^{13}$C NMR (100 MHz, $CDCl_3$) δ 169.1, 143.7, 128.7, 128.1, 127.5, 127.0, 120.4, 115.3, 114.6, 80.8, 64.2, 42.3, 28.3 (X3); IR (neat) 3332, 2978, 2227, 1689, 1513, 1279, 1248, 910, 728; HRMS (ESI): m/z calcd. for $C_{17}H_{19}N_3O_2S^+$ (M+Na)$^+$ 368.1039, found 368.1030.

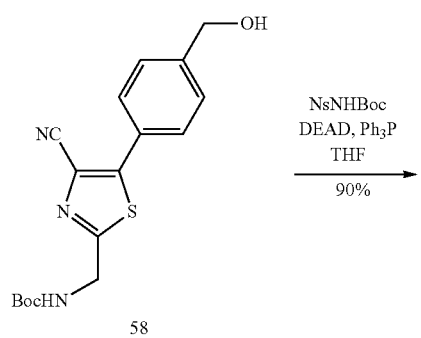

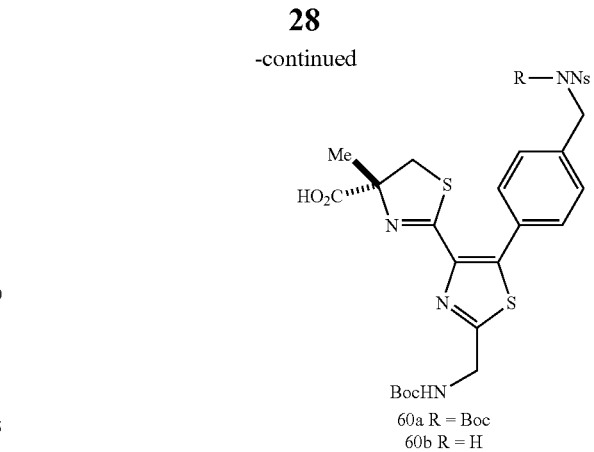

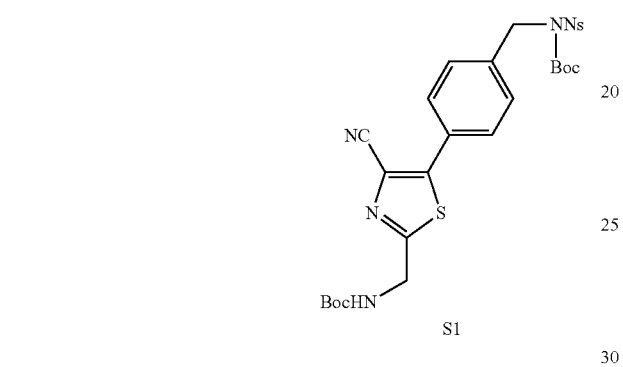

Thiazole nitrile S1 (377 mg, 0.6 mmol), α-methyl-cysteine-HCl (124 mg, 0.72 mmol), NaHCO$_3$ (76 mg, 0.9 mmol) were combined and 10 mL of methanol was added. To the mixture was added Et$_3$N (0.16 mL, 1.2 mmol). After refluxed at 70° C. for 36 hours, the solvent was removed under reduced pressure. The residue was purified by flash column chromatography on silica gel (9% to 30% ethyl acetate in DCM) to afford 230 mg (60a:60b=1:1, 59%) of 60a and 60b as a yellow foam.

60a and 60b were used as a mixture for the next reaction without further purification and characterization.

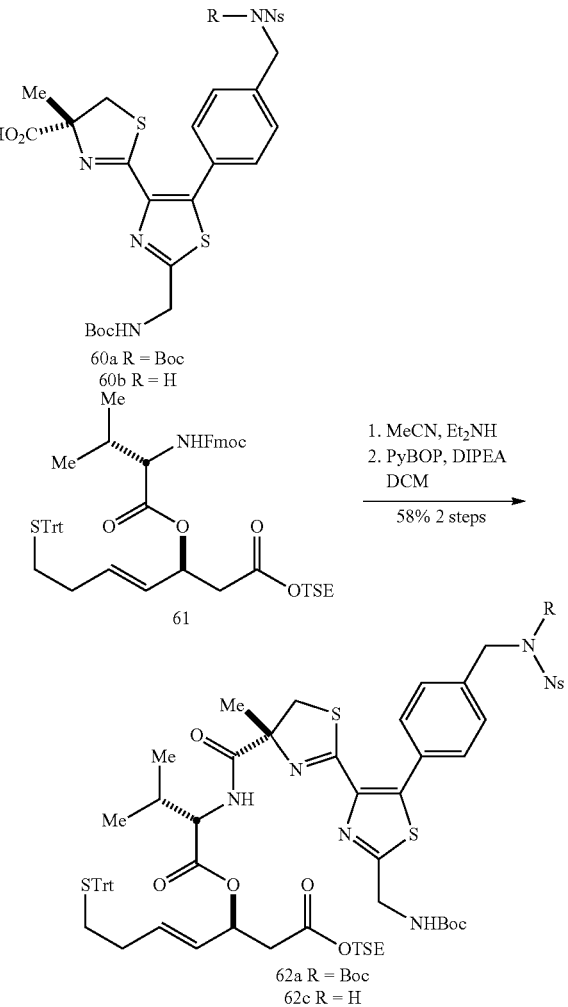

Benzyl alcohol 58 (35 mg, 0.1 mmol), NsNHBoc (45 mg, 015 mmol), PPh$_3$ (39 mg, 0.15 mmol) were combined and 1 mL of THF was added. To the mixture was added DEAD (40% in toluene, w/w, 75 μL, 0.15 mmol) at 0° C. After stirred at 0° C. for 30 min, the solution was washed with 1N HCl, dried over Na$_2$SO$_4$, filtered, and concentrated under reduced pressure. The residue was purified by flash column chromatography on silica gel (0% to 4% ethyl acetate in DCM) to afford 57 mg (90% yield) of S1 as a yellow solid.

$^1$H NMR (400 MHz, CDCl$_3$) δ 8.32 (dd, J=8.3, 1.7 Hz, 1H), 7.79-7.69 (m, 5H), 7.54 (d, J=8.2 Hz, 1H), 5.54 (brs, 1H), 4.99 (S, 2H), 4.57 (d, J=5.9 Hz, 2H), 1.46 (s, 9H), 1.28 (s, 9H); $^{13}$C NMR (100 MHz, CDCl$_3$) 176.2, 169.2, 150.2, 147.6, 140.0, 134.5, 133.8, 133.1, 132.4, 132.0, 128.5, 128.4, 127.5, 124.6, 120.7, 114.7, 85.7, 80.8, 50.6, 42.5, 28.3 (X3), 27.8 (X3).

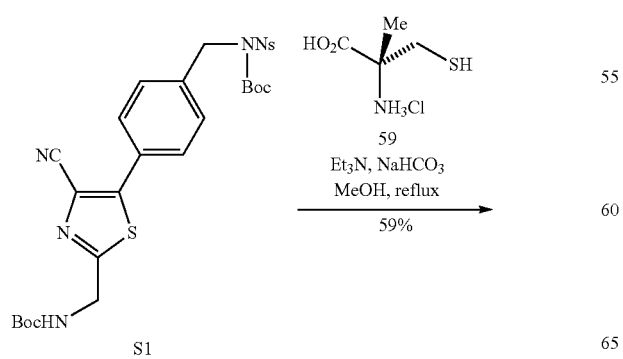

61 (336 mg, 0.4 mmol) was dissolved 40 mL of CH₃CN. 4 mL of diethylamine was added at 0° C. The bath was removed and the resulted solution was stirred at room temperature for 2 hours, then evaporated, azeotroped with toluene (2×2 mL), dried under vacuum. In another round flask, acid 60 (230 mg, 0.35 mmol, mixture of 60a and 60b, 1:1) was dissolved in 55 mL of DCM. PyBOP (416 mg, 0.8 mmol) and DIPEA (210 µL, 1.2 mmol) were added and the mixture was allowed to stir at room temperature for 20 minutes. To the resulting solution was added a DCM solution (totally 25 mL) of crude amine. After 3 hours, the reaction was concentrated and submitted immediately to column chromatography, (0% to 25% ethyl acetate in DCM) to afford macrocyclization precursor (236 mg, 58%, 62a: 62b=1:1) as a yellow foam.

62a and 62b were used as a mixture for the next reaction without further purification or characterization.

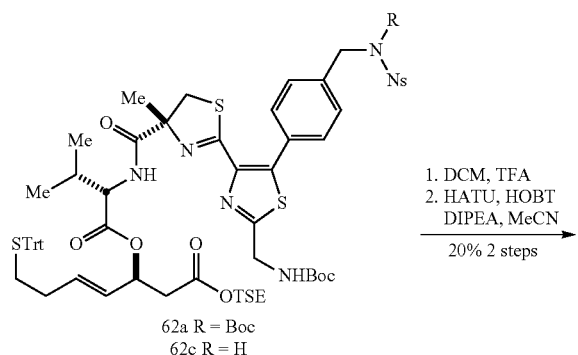

62a R = Boc
62c R = H

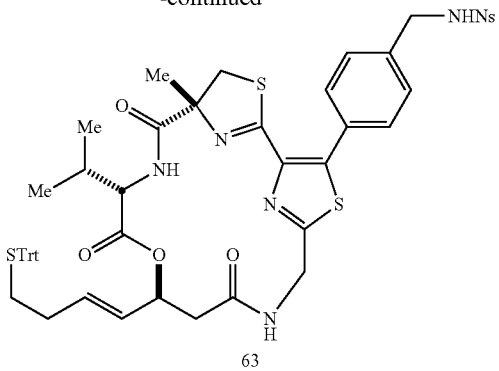

63

Acyclic precursor (236 mg, 0.2 mmol, mixture of 62a and 62b, 1:1) was dissolved in 30 mL of DCM, 6 mL of TFA was added to the solution at 0° C. The reaction was allowed to warm to room temperature and stirred for 16 hours. Solvents were evaporated and the crude amino acid was azeotroped with toluene (10×3 mL) to remove residual TFA. The crude amino acid was then dissolved in 300 mL of CH₃CN (to ~0.001M), DIPEA (0.32 mL, 1.8 mmol) was added. The resulting moderately opaque solution was allowed to stir for 10 min, before a MeCN (10 mL) solution of HATU (230 mg, 0.6 mmol) and HOBt (81 mg, 0.6 mmol) were added dropwise. The reaction was allowed to stir for 26 hours, then concentrated under reduced pressure. The residue was purified by flash column chromatography on silica gel (0% to 11% AcOEt in DCM for the first column, 25% to 75% ethyl acetate in hexane for the second column and 0% to 9% AcOEt in DCM for the third column) to afford 40 mg (20% yield for 2 steps) of 63 as a yellow foam.

63 was used for the next reaction without further characterization.

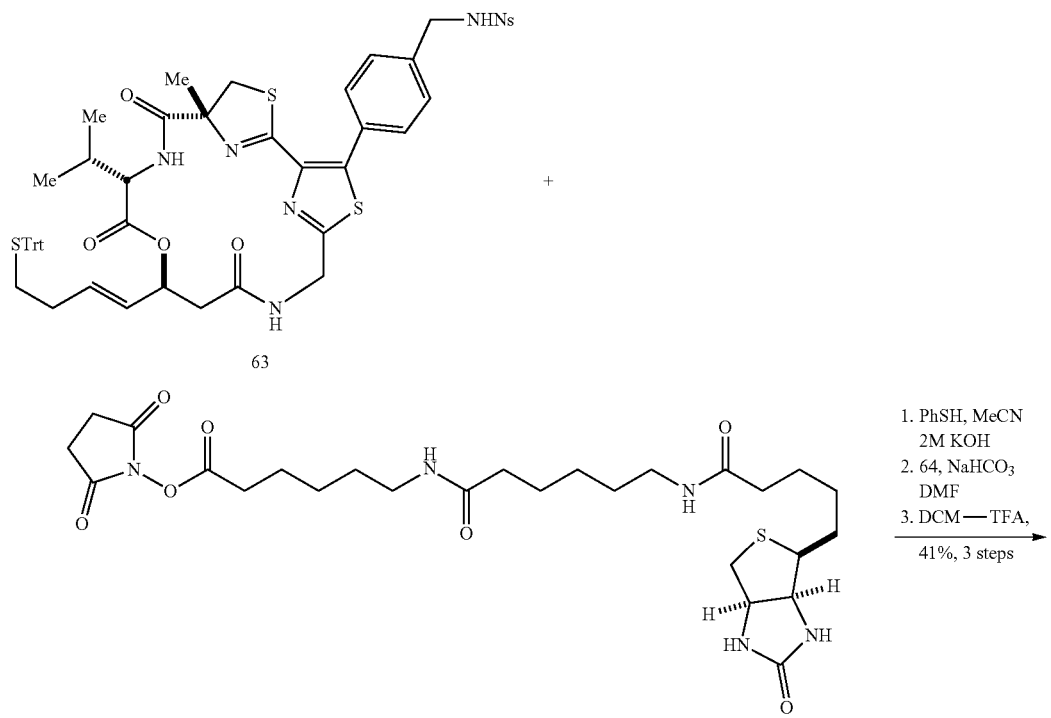

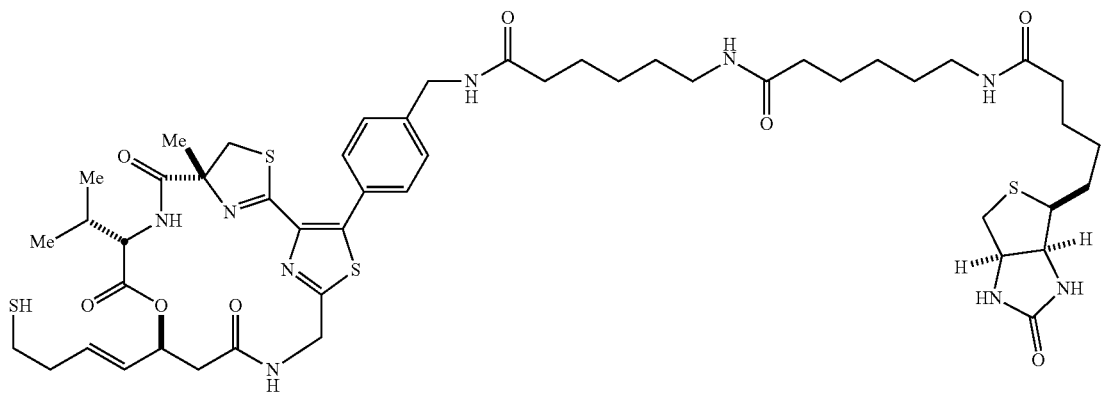

54

Thiophenol (10.4 µL, 0.1 mmol), KOH (3.6 mg, 64 µmol), water (30 µL) and acetonitrile (1.2 mL) were combined to give a colorless solution. To 8.2 mg (9.1 µmol) of Ns amine 63 was added 0.4 mL of above solution at room temperature. The reaction was allowed to stir for 2 hours. Then diluted with 4 mL of hexane and submitted directly to column chromatography (100% AcOEt then 25% MeOH in DCM) to afford 6.0 mg (78% yield) of free amine as a yellow oil.

Free amine (6.0 mg, 9 µmol), biotin derivative 64 (8.1 mg, 18 µmol), NaHCO$_3$ (1.5 mg, 18 µmol) were combined. DMF (0.3 mL) was added at and the reaction was allowed to stir for 14 h, then concentrated under reduced pressure. The residue was purified by flash column chromatography on silica gel (100% AcOEt then 5% to 11% MeOH in DCM) then by preparative TLC (9% MeOH in DCM for 3 times) to afford pure coupling product as a yellow oil.

Coupling product was dissolved in 0.6 mL of DCM and cooled to 0° C. TFA (30 µL) and iPr$_3$SiH (1.0 µL, 6 µmol) were added to the solution at 0° C. The bath was removed and the reaction was allowed to stir at room temperature for 1 h. Solvent was removed by argon flow and the residue was purified by flash column chromatography on silica gel (0 to 9% MeOH in CHCl$_3$) to afford 4.0 mg of free thiol 54 (53% for 2 steps). This is further purified by preparative TLC (9% MeOH in DCM for 2 times) to afford the pure sample for biological evaluation.

$[\alpha]_D^2$=+52.0° (C=0.05 in CH$_3$OH); $^1$H NMR (CD$_3$OD, 600 MHz) 7.48 (2H, d, J=8.0 Hz), 7.40 (2H, d, J=8.0 Hz), 5.92-5.82 (2H, m), 5.72-5.63 (2H, m), 5.13 (1H, d, J=8.0 Hz), 4.59-4.55 (2H, m), 4.49 (1H, dd, J=7.7, 4.7 Hz), 4.44-4.40 (3H, m), 4.30 (1H, dd, J=7.7, 4.7 Hz), 3.77 (1H, d, J=11.6 Hz), 3.60 (1H, s), 3.27 (1H, d, J=11.6 Hz), 3.21-3.15 (5H, m), 2.98-2.91 (2H, m), 2.76-2.69 (3H, m), 2.56 (1H, dd, J=6.9, 6.9 Hz), 2.45 (1H, dd, J=13.5, 6.5 Hz), 2.36 (1H, m), 2.28 (2H, dd, J=7.4, 7.4 Hz), 2.23-2.09 (6H, m), 1.81 (3H, s), 1.76-1.29 (23H, m), 0.74 (3H, d, J=6.9 Hz), 0.59 (3H, d, J=6.9 Hz); $^{13}$C NMR (CD$_3$OD, 125 MHz) 176.1, 176.0, 175.9, 175.8, 171.8, 170.4, 168.3, 167.2, 166.0, 144.7, 143.0, 142.5, 133.7, 131.4, 120.7, 129.1, 128.8, 84.0, 73.8, 64.3, 63.3, 61.6, 58.9, 57.0, 44.4, 43.6, 41.2, 41.0, 40.2, 38.7, 37.0, 36.9, 36.8, 35.2, 32.7, 30.1, 29.8, 29.5, 27.5, 26.9, 26.7, 26.6, 24.5, 19.8, 17.3; IR (neat) 3308, 2930, 2859, 1656, 1551, 1462, 1262, 667; HRMS (ESI): m/z calcd. for C$_{50}$H$_{72}$N$_9$O$_8$S$_4^+$ (M+H)$^+$ 1054.4381, found 1054.4346.

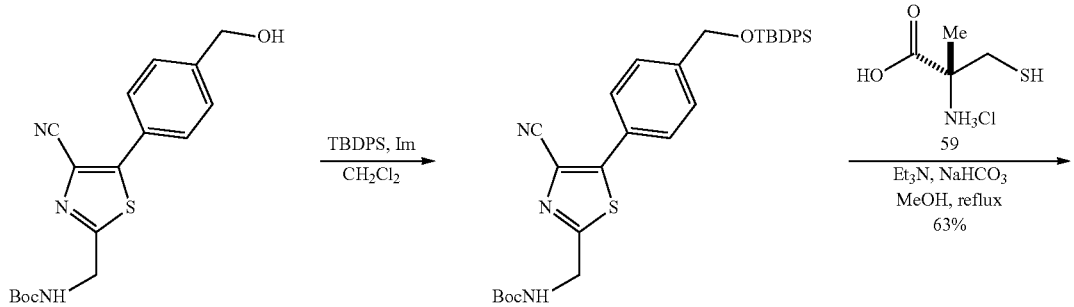

-continued
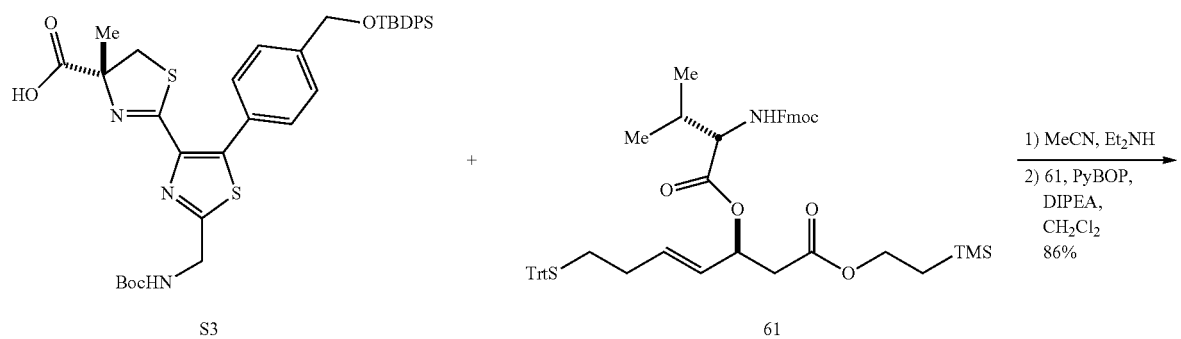
S3 + 61 → 1) MeCN, Et₂NH
2) 61, PyBOP, DIPEA, CH₂Cl₂
86%
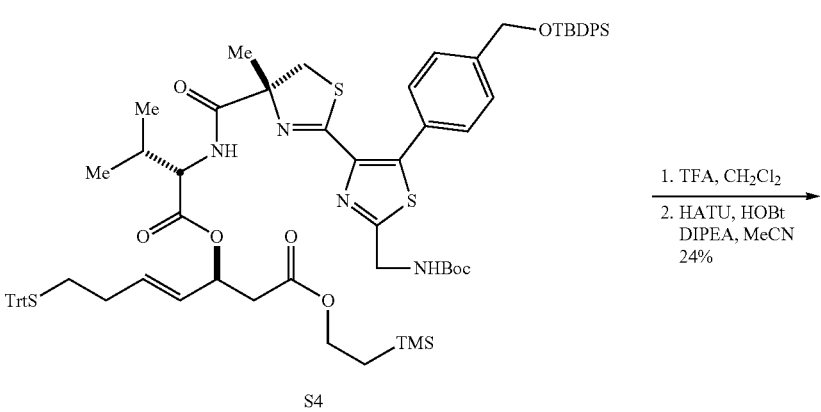
S4
1. TFA, CH₂Cl₂
2. HATU, HOBt DIPEA, MeCN
24%
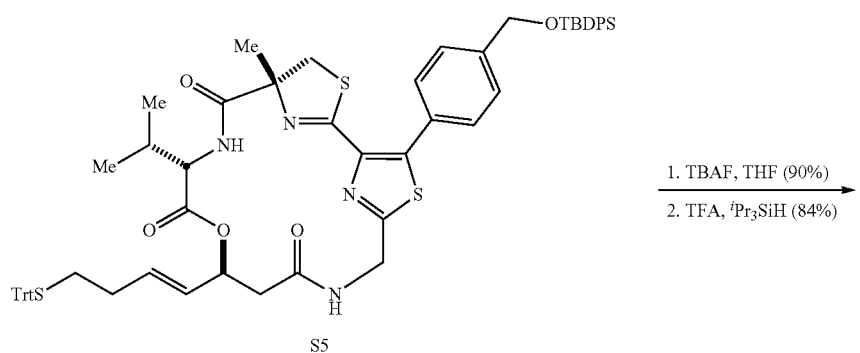
S5
1. TBAF, THF (90%)
2. TFA, ⁱPr₃SiH (84%)
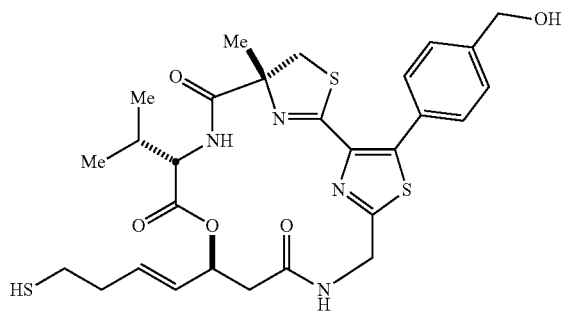
51

Preparation:

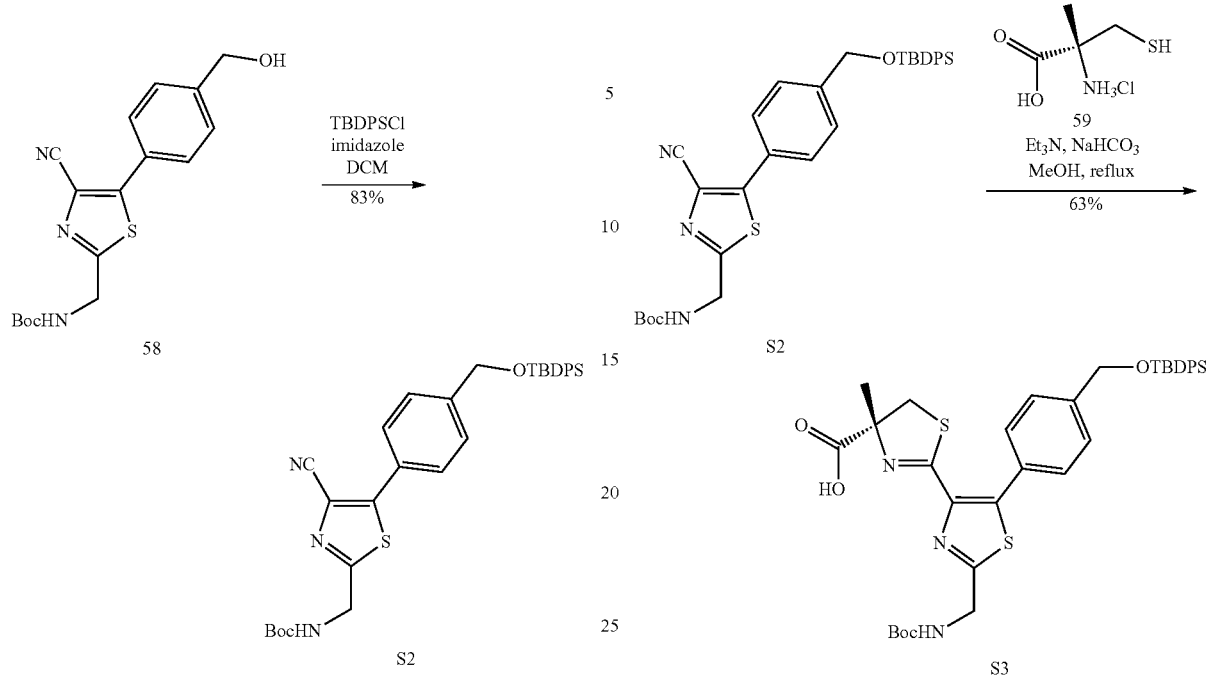

Free benzyl alcohol 58 (420 mg, 1.2 mmol), imidazole (245 mg, 3.6 mmol) was combined and 12 mL of DCM was added. To the resulted solution was added TBDPSCl (560 μL, 2.4 mmol). The mixture was allowed to stirred at room temperature for 14 hours, then treated with aq. $NH_4Cl$ (unsaturated), diluted with DCM, separated, dried over $Na_2SO_4$, filtered, and concentrated under reduced pressure. The residue was purified by flash column chromatography on silica gel (9% to 16% ethyl acetate in hexane) to afford 580 mg (83% yield) of silyl ether S2 as a yellow oil.

$^1$H NMR (400 MHz, $CDCl_3$) δ 7.71-7.69 (m, 6H), 7.48-7.37 (m, 8H), 5.38 (brs, 1H), 4.81 (s, 2H), 4.58 (d, J=8.2 Hz, 2H), 7.41 (d, J=8.2, 2H), 5.64 (brs, 1H), 4.70 (s, 2H), 4.52 (d, J=6.1 Hz, 2H), 1.48 (s, 9H), 1.11 (s, 9H); $^{13}$C NMR (100 MHz, $CDCl_3$) δ 168.6, 155.7, 144.0, 135.6, 133.2, 129.9, 128.1, 127.9, 126.9, 120.6, 114.8, 80.8, 65.0, 42.5, 28.4 (X3), 26.9 (X3), 19.4; IR (neat) 3352, 2930, 2856, 2227, 1705, 1507, 1366, 1247, 1106, 823, 700; HRMS (ESI): m/z calcd. for $C_{33}H_{37}N_3NaO_3SSi^+$ (M+Na)$^+$ 606.2217, found 606.2211.

Thiazole nitrile S2 (420 mg, 0.72 mmol), α-methyl-cysteine-HCl 59 (185 mg, 1.08 mmol), $NaHCO_3$ (91 mg, 1.08 mmol) were combined and 4 mL of methanol was added. To the mixture was added $Et_3N$ (0.19 mL, 1.44 mmol). After refluxed at 70° C. for 15 hours, the solvent was removed under reduced pressure and retreated with ethyl acetate. The suspension was washed with 1M aqueous $KHSO_4$ and brine, dried over $Na_2SO_4$, filtered, and concentrated under reduced pressure. The residue was purified by flash column chromatography on silica gel (9% ethyl acetate in DCM) to afford 120 mg (28% yield) of starting material and then (9% methanol in DCM) to afford 320 mg (63% yield) of S3 as a yellow oil.

$^1$H NMR (400 MHz, $CDCl_3$) δ 9.40 (brs, 1H), 7.73 (d, J=7.7 Hz, 4H), 7.48-7.26 (m, 10H), 5.56 (brs, 1H), 4.83 (s, 2H), 4.63 (d, J=5.7 Hz, 2H), 3.74, (d, J=11.5 Hz, 1H), 3.25 (d, J=11.5 Hz, 1H), 1.54 (s, 3H), 1.49 (s, 9H), 1.13 (s, 9H); $^{13}$C NMR (100 MHz, $CDCl_3$) δ 168.6, 155.7, 144.0, 135.6, 133.2, 129.9, 128.1, 127.9, 126.9, 120.6, 114.8, 80.8, 65.0, 42.5, 28.4 (X3), 26.9 (X3), 19.4; HRMS (ESI): m/z calcd. for $C_{37}H_{44}N_3O_5S_2Si^+$ (M+H)$^+$ 702.2486, found 702.2484.

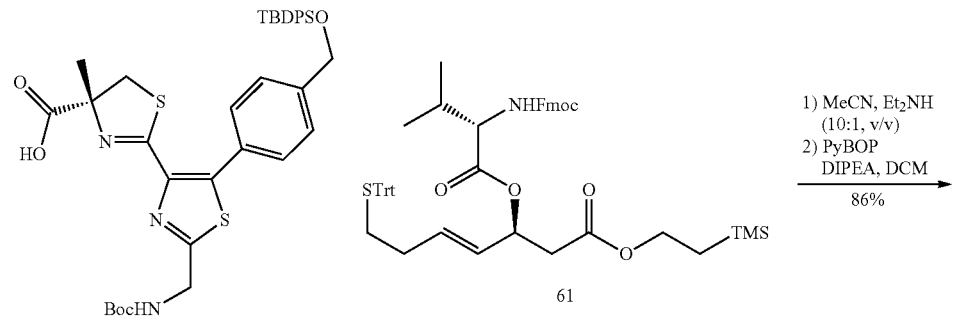

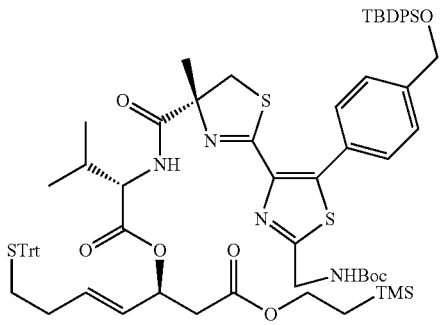

61 (490 mg, 0.58 mmol) was dissolved 50 mL of CH₃CN. 5 mL of diethylamine was added at 0° C. The bath was removed and the resulted solution was stirred at room temperature for 2 hours, then evaporated, azeotroped with toluene (2×2 mL), dried under vacuum. In another round flask, acid S3 (410 mg, 0.58 mmol) was dissolved in 75 mL of DCM. PyBOP (600 mg, 1.16 mmol) and DIPEA (300 μL, 1.74 mmol) were added and the mixture was allowed to stir at room temperature for 20 minutes. To the resulting solution was added a DCM solution (totally 25 mL) of crude amine. After 3 hours, the reaction was concentrated and submitted immediately to column chromatography, (6% to 25% ethyl acetate in hexane) to afford macrocyclization precursor S4 (650 mg, 86%) as a yellow foam.

¹H NMR (400 MHz, CDCl₃) δ 7.72-7.70 (m, 4H), 7.52 (d, J=8.1 Hz, 2H), 7.43-7.35 (m, 15H), 7.28-7.17 (m, 8H), 6.83 (d, J=8.8 Hz, 1H), 5.60-5.52 (m, 2H), 5.41 (brs, 1H), 5.32 (dd, J=15.4, 7.3 Hz, 2H), 4.86-4.78 (m, 2H), 4.63 (d, J=5.7 Hz, 2H), 4.31 (dd, J=8.7, 5.2 Hz, 2H), 4.14 (dd, J=9.0, 8.0 Hz, 2H), 3.63, (d, J=11.5 Hz, 1H), 3.23 (d, J=11.5 Hz, 1H), 2.63 (dd, J=15.4, 7.3 Hz, 1H) 2.50 (dd, J=15.6, 6.2 Hz, 1H), 2.16-2.12 (m, 2H), 2.00-1.93 (m, 2H), 1.50 (s, 9H), 1.47 (s, 3H), 1.12 (s, 9H), 0.98-0.92 (m, 2H), 0.74 (d, J=6.8 Hz, 3H), 0.60 (d, J=6.8 Hz, 3H), 0.04 (s, 9H); ¹³C NMR (100 MHz, CDCl₃) δ 1174.5, 170.0, 169.5, 162.7, 144.8, 142.4, 141.5, 135.5, 133.3, 130.1, 129.8, 129.5, 128.5, 127.9, 127.8, 126.6, 125.7, 80.4, 71.3, 66.6, 65.1, 63.0, 56.9, 42.3, 41.0, 39.7, 31.3, 31.1, 28.4, 26.9, 24.5, 19.3, 19.0, 17.5, 17.3, −1.4; IR (neat) 3379, 3054, 2959, 2930, 2857, 1737, 1675, 1507, 1444, 1366, 1249, 1166, 1111, 835, 752; HRMS (ESI): m/z calcd. for $C_{78}H_{88}N_4NaO_8S_3Si_2^+$ (M+Na)⁺ 1323.5200, found 1323.5165.

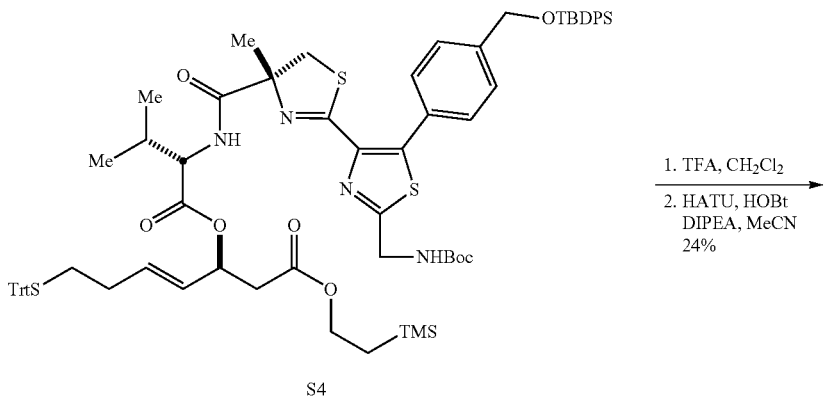

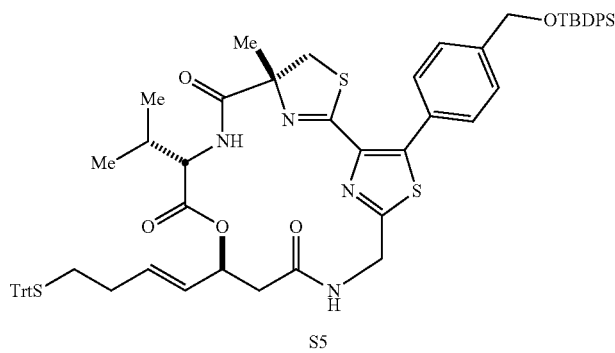

Acyclic precursor S4 (55 mg, 0.042 mmol) was dissolved in 5 mL of DCM, 1 mL of TFA was added to the solution at 0° C. The reaction was allowed to warm to room temperature and stirred for 16 hours. Solvents were evaporated and the crude amino acid was azeotroped with toluene (2×2 mL) to remove residual TFA. The crude amino acid was then taken up in 2 mL DCM and added to a stirred solution of DIPEA (50 µL, 0.25 mmol) in 40 mL of $CH_3CN$ (to ~04.001M). The resulting moderately opaque solution was allowed to stir for 10 min., before a MeCN (10 mL) solution of HATU (31 mg, 0.084 mmol) and HOBt (11 mg, 0.08 mmol) were added dropwise. The reaction was allowed to stir for 26 hours, then concentrated and redissolved in AcOEt. The solution was washed with saturated aqueous $NH_4Cl$, $NaHCO_3$ and brine, dried over $Na_2SO_4$, filtered, and concentrated under reduced pressure. The residue was purified by flash column chromatography on silica gel (9% methanol in DCM for the first column and 16% to 50% ethyl acetate in hexane for the second column) to afford 10.9 mg (24% yield) of S5 as a yellow foam.

$[\alpha]_D^{25}$=+25.3° (C=0.154 in $CHCl_3$); $^1H$ NMR (400 MHz, $CDCl_3$) δ 7.67 (d, J=7.0 Hz, 4H), 7.45-7.13 (m, 25H), 6.79 (brs, 1H), 5.74-5.64 (m, 2H), 5.41 (dd, J=11.5, 6.0 Hz, 1H), 5.10 (dd, J=17.6, 8.0 Hz, 1H), 4.81 (s, 2H), 4.61 (dd, J=9.4, 3.7 Hz, 1H), 4.23 (dd, J=17.4, 1.8 Hz, 1H), 3.86 (d, J=11.4 Hz, 1H), 3.18 (d, J=11.4 Hz, 1H), 2.70-2.69 (m, 2H), 2.25-2.01 (m, 5H), 1.80 (s, 3H), 1.23 (dd, J=6.9, 6.4 Hz, 1H), 1.09 (s, 9H), 0.72 (d, J=6.7 Hz, 3H), 0.61 (d, J=6.8 Hz, 3H); 172.5, 169.1, 168.9, 165.6, 145.0, 135.7, 133.3, 130.2, 130.0, 129.7, 128.0, 127.9, 127.7, 126.8, 126.2, 71.7, 66.9, 65.2, 58.0, 44.1, 41.0, 40.8, 34.1, 31.7, 31.4, 27.0, 19.5, 19.2, 17.4; IR (neat) 3227, 2959, 2868, 103, 1484, 1250, 1195 1036, 738; HRMS (ESI): m/z calcd. for $C_{63}H_{67}N_4O_5S_3Si$ $(M+H)^+$ 1083.4037, found 1083.4021.

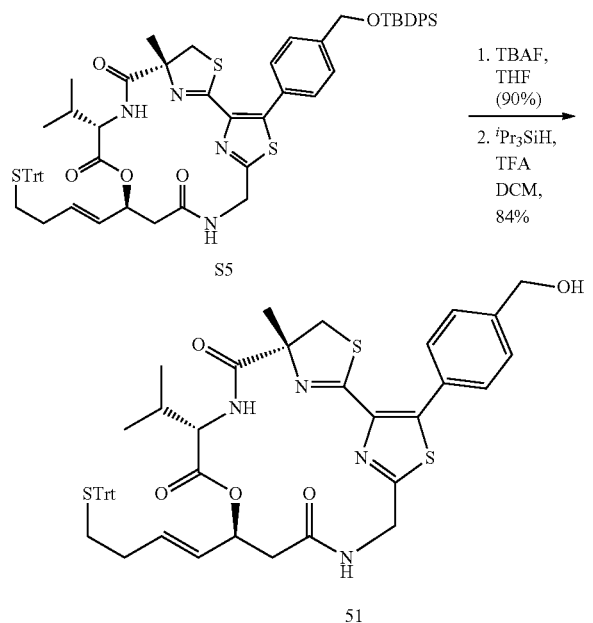

TBDPS protect benzyl alcohol S5 (7.0 mg, 6 µmol) was dissolved in 0.2 mL of THF, TBAF (1.0 M in THF, 6 µL, 6 µmol) was added to the solution. The reaction was allowed to stir at room temperature for 1 hour. Solvents were evaporated and the residue was purified by flash column chromatography on silica gel (1 to 7% methanol in DCM) to afford 4.6 mg (90% yield) of free benzyl alcohol as a yellow foam.

Trityl thiol (3.6 mg, 4 µmol) was dissolved in 0.2 mL of DCM. 10 µL of TFA and $iPr_3SiH$ (1.7 µL, 8 µmol) were added to the solution at 0° C. The reaction was allowed to warm to room temperature and stirred for 2 hours. Solvents were evaporated and the residue was purified by flash column chromatography on silica gel (1 to 6% methanol in DCM) to afford 2.0 mg (84% yield) of free thiol 51 as a yellow foam.

$^1H$ NMR (400 MHz, $CDCl_3$) δ 7.53-7.44 (m, 3H), 7.32 (dd, J=10.1, 0.4 Hz, 1H), 6.80 (brs, 1H), 5.86 (ddd, J=15.5, 7.6, 7.4 Hz, 1H), 5.76 (dd, J=13.0, 6.8 Hz, 1H), 5.58 (dd, J=15.6, 6.3 Hz, 1H), 5.13 (dd, J=17.7, 7.7 Hz, 1H), 4.78 (s, 2H), 4.68 (dd, J=9.7, 4.3 Hz, 1H), 4.44 (dd, J=17.8, 3.2 Hz, 1H), 3.87 (d, J=11.5 Hz, 1H), 3.16 (d, J=11.5 Hz, 1H), 2.76 (d, J=5.9 Hz, 2H), 2.56 (dd, J=14.5, 7.6 Hz, 2H), 2.36 (m, 2H), 2.09 (ddd, J=11.3, 7.1, 4.4 Hz, 2H), 1.84 (s, 3H), 1.23 (dd, J=6.9, 6.4 Hz, 1H), 0.76 (d, J=6.7 Hz, 3H), 0.64 (d, J=6.8 Hz, 3H); HRMS (ESI): m/z calcd. for $C_{28}H_{35}N_4O_5S_3$ $(M+H)^+$ 603.1764, found 603.1769.

Example 2. Identification of the Protein Targets of Largazole

The mechanistic characterization of largazole drug action was begun with experiments directed at the elucidation of the protein complexes engaged by the natural product HDACi. Biochemical profiling in homogeneous assays suggests selective inhibition of HDACs1-3. However, these targets exist in disparate regulatory complexes. A chemoproteomics study of pharmaceutical (synthetic) HDAC inhibitors by Bantscheff and colleagues identified surprising complex-specific binding of hydroxamic acid and benzamide HDAC inhibitors that could not have been predicted by homogenous assays (Bantscheff, et al. 2011 Nature Biotech 29:255-265). To elucidate the largazole target complexes in an unbiased manner, ligand-affinity chromatography and mass spectroscopy are used.

Specifically, Largazole-Biotin is used as an affinity reagent, and SILAC (stable isotope labeling by amino acids in cell culture)-based target identification technology resolved by mass spectrometry (Ong, et al. 2009 PNAS US 106:4617-4622) is employed. In brief (FIG. 4), cells are grown in labeling media containing either 'light' forms of arginine and lysine or 'heavy' L-Arg-$^{13}C6$ and L-Lys-$^{13}C6$-$^{15}N2$ for at least six cell divisions before being lysed. The "light" lysate is pre-incubated with excess free largazole thiol, while the heavy is pre-incubated with an equal amount of DMSO. Immobilized Largazole-Biotin is then added separately to the 'light' or 'heavy' lysates. Excess soluble Largazole thiol is added to the 'light' lysates to compete with proteins for binding to immobilized compound. SILAC ratios based on relative abundances of proteins enriched in 'heavy' versus 'light' pulldowns are then modeled using MaxQuant software and a modified T-test.

For these studies, target identification of largazole is performed in one cutaneous T-cell lymphoma cell line (Hut78), one multiple myeloma cell line (MM1.S), and one acute leukemia cell line (MV4;11). Proteomic data is analyzed using protein-protein interaction knowledge-bases (e.g. STRING, Reactome) to suggest stable complexes. Discrete interactions are confirmed by affinity purification against a dose-response of free largazole thiol, with confirmation of target enrichment by immunoblot. The targets of largazole are then further explored as cancer-specific dependencies by orthogonal genetic perturbation in the corresponding cellular context (shRNA and/or Cas9-CRISPR genome editing). Knowledge of targets also informs late-stage studies reporting on modulation of chromatin structure and function and largazole thiol binding genome-wide, both described herein.

Example 3. Establishment of the Mechanism of Largazole Anti-Proliferative Activity by Characterizing Functional Effects on Chromatin Structure and Transcriptional Output The locus-specific transcriptional consequences of BET bromodomain inhibitors in hematologic malignancies have recently been elucidated (Loven, et al. 2013 *Cell* 153:320-334; Chapuy, et al. 2013 *Cancer Cell* 24:777-790). These studies established capabilities in integrated epigenomics: genome-wide chromatin mark or factor enrichment (ChIP-Seq) and quantitative analysis of transcriptional kinetics (gene expression profiling; GEP). Together, these instruments report on the structure and function of chromatin pre- and post-compound exposure. The kinetic effects of largazole HDAC inhibition are studied in myeloma (MM1.S) and CTCL (MJ) to understand the mechanistic consequence of global hyperacetylation and to test the hypothesis that epigenomic reprogramming occurs with BET bromodomain redistribution.

Specifically, ChIP-Seq is used to generate and integrate Class 1 HDAC localization data with global maps of chromatin acetylation, histone occupancy, and transcription in CTCL (Hut78) and MM (MM1.S) cells. Chromatin and transcriptional maps will be produced using ChIP-Seq for well-established surrogate marks for chromatin state including pan-H3 (histone occupancy), H3K27ac and H3K9/K14ac (acetylated chromatin), H3K4me3 (transcription initiation), BRD4 (BET bromodomain/chromatin co-activator occupancy), and RNA PolII (transcription). As Class I HDACs have been shown to localize to promoters of active genes, integrative analysis of comprehensive HDAC1-3 occupancy establishes the spatial relationship between HDACs and local chromatin structure throughout the MM and CTCL tumor genome.

Treatment with HDACi's has been shown to globally de-compact chromatin through widespread histone hyperacetylation, however the global consequences of HDACi treatment on tumor transcriptional output are poorly characterized. Given the global effects of HDACi on tumor cell chromatin, precise cell count normalized measurements of chromatin and transcription dynamics are required to understand the kinetic absolute effects of largazole HDAC inhibition. Recently, highly quantitative techniques have been developed to measure cell count normalized changes in chromatin state and gene expression (Orlando, et al. 2014 *Cell Reports* 9:1-8). These techniques incorporate exogenous spike-ins added in cell count equivalents to enable normalization of chromatin occupancy or gene expression to cell number. Additionally, analysis methods have been established to quantify global redistribution of chromatin co-activators and their consequent effects on transcriptional output in response to cell state transition and drug treatment (Brown, et al. 2014 *Mol Cell* 56:219-231). Using these combined approaches, the kinetic chromatin structure of largazole treated MM1.S and Hut78 cells are interrogated at high temporal resolution (0, 4, 12, and 24 hours after treatment). Specifically, cell count-normalized dynamic measurements of H3K9/K14ac, H3K27ac, RNA Pol II, BRD4 are obtained, as well as gene expression at each time point in response to largazole treatment.

Inhibition of Class I HDAC activity at active gene promoters will likely result in focal hyperacetylation that at later time points escalates into global chromatin de-compaction and widespread hyperacetylation. As such, the high temporal resolution of the proposed measurements helps elucidate and distinguish direct and early deregulating transcriptional consequences from indirect and late secondary consequences. Changes in chromatin can impact transcription by altering the activity of gene regulatory cis elements at promoters and gene distal enhancers. Using ATAC-Seq, a measure of accessible nucleosome free regions, the formation of de novo cis-regulatory elements established is mapped by transcription factor binding to newly accessible hyperacetylated chromatin. Computational analysis of dynamic enhancer composition identifies candidate tumor cell transcription factors with altered target genes as likely mediators of largazole HDAC inhibition anti-proliferative response. It is hypothesized that largazole HDAC inhibition causes the disruption of established tumor transcriptional programs through the aberrant recruitment and redistribution of chromatin co-activators. The net effect of this transcriptional "chaos" resulting from largazole inhibition is investigated and validated globally through identification of selectively deregulated pathways and via locus-specific assays measuring deregulation of critical oncogene such as p21, HEXIM1, and MYC.

Example 4. Spatial Localization of Sites of Largazole Action Genome-Wide

Finally, to understand the effects of largazole HDAC inhibition in cancer, genome-wide chromatin studies of drug molecules to allow spatial resolution of drug binding to the epigenome has been created by combining ligand affinity chromatography with massively parallel epigenomic sequencing. ChemSeq identifies sites of enriched binding within cancer epigenomes in a manner unbiased by knowledge of protein target (Anders, et al. 2014 *Nature Biotechnol* 32:92-96). In the index study, biotinylated derivatives of the JQ1 BET bromodomain inhibitor, a CDK9 inhibitor, and the DNA binding agent psoralen were used. Here, Largazole-Biotin is employed to enrich CTCL (Hut78) and MM (MM1.S) chromatin using two methods: pull-downs of pre-fragmented, fixed chromatin (in vitro ChemSeq) and chromatin from treated cells (in vivo ChemSeq). Largazole-Biotin binding to the epigenome is then integrated with (a) HDAC1-3 ChIP-Seq data to confirm target co-localization, (b) enhancer/promoter marks to identify regional engagement, (c) heterochromatin marks to discover novel binding regions, and (d) transcriptional profiling data to explore the hypothesis that genes bound disproportionately by Largazole thiol (featuring early regional hyperacetylation as in Example 19) are more sensitive by transcriptional response. Studies of Largazole dynamic response are informed previously published research that has characterized the kinetic effects of chromatin-active small molecules dynamically in multiple myeloma, diffuse lymphoma (DLBCL), and heart failure (Anand, et al. 2013 *Cell* 154:569-582).

Data Interpretation

Figure 4:
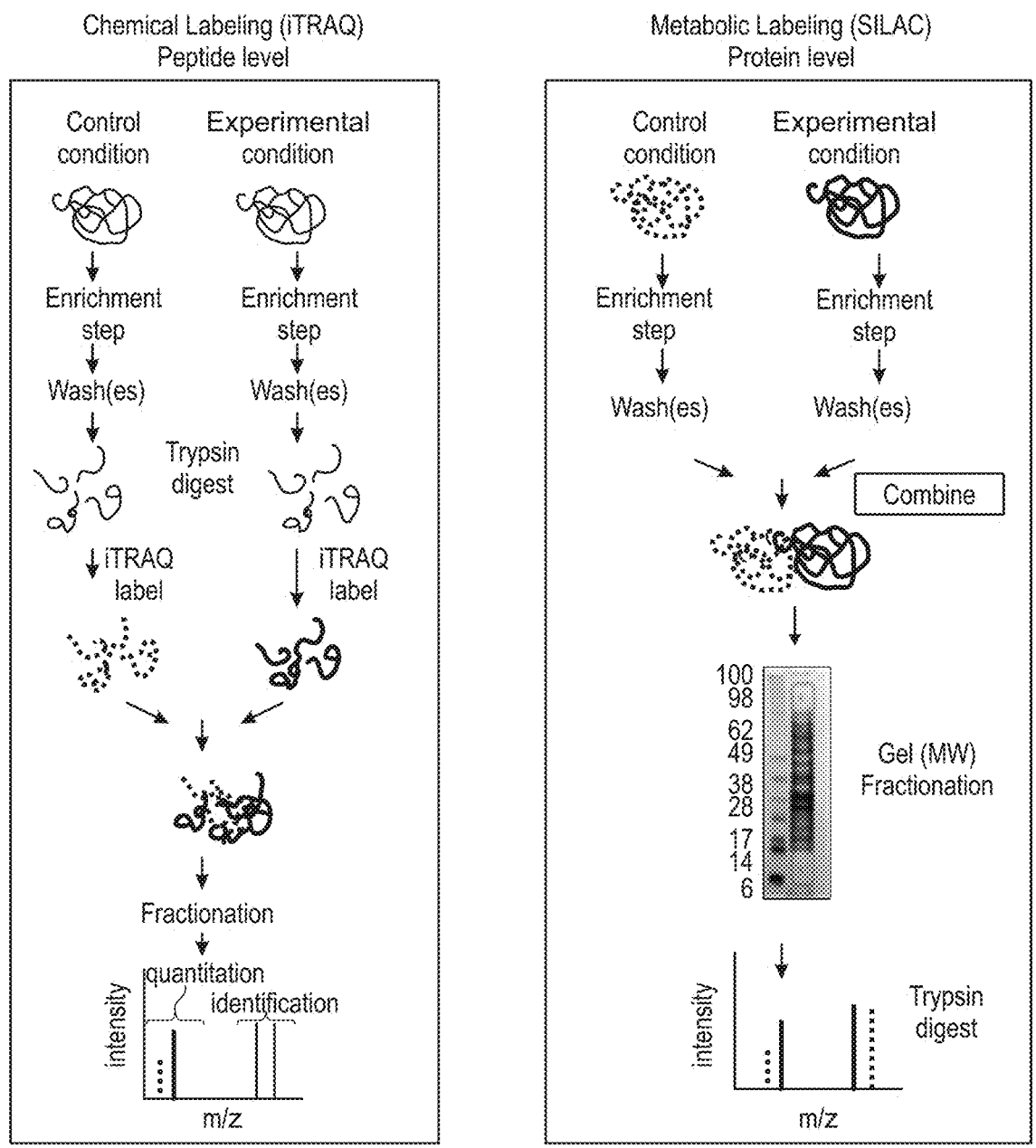
FIG. 4 shows a schematic comparison of affinity enrichment methods using chemical (iTRAQ) and metabolic (SILAC) screening.

Regarding chemoproteomic characterization of largazole, conditions have already been established for isotope labeling for MM1.S and MV4 (Taori, et al. 2008 *J Am Chem Soc* 130:1806-1807). If Hut78 cells are not amenable to SILAC labeling, the experiment can be performed using chemical labeling at the peptide level, most commonly using isobaric tags for relative and absolute quantitation (iTRAQ; FIG. 4) (Ross, et al. 2004 *Mol & Cell Proteomics* 3:1154-1169). The kinetic study of chromatin structure may produce global changes as early as 4 hours. If this occurs, additional time-points are added at 30 minutes and 60 minutes. Regarding Chem-Seq, if Largazole-Biotin does not prove capable of retrieving nuclear chromatin post-fixation, UV photo-affinity reagents are created for largazole via conjugation of an appending benzo-phenone alkyne (Salisbury, et al. 2008 *J Am Chem Soc* 130:2184-2194; Salisbury, et al. 2007 *PNAS USA* 104:1171-1176). Alternatively, the retrievable biotinylated linker is conjugated to the cysteine feature of Romidepsin, allowing characterization of the FDA-approved natural product.

Example 5. Expansion of the Leukemia-Specific Therapeutic Index of Largazole Through Small Molecule and Biomolecule Conjugation The synthetic accessibility of largazole, a strong mechanistic rationale, and the extraordinary anti-proliferative activity of HDAC inhibition are leveraged to direct unusually potent largazole derivatives to leukemia and lymphoma cells as targeted therapy. Regrettably, there does not exist an adequate therapeutic index to achieve the exposures required to inhibit leukemia and lymphoma growth in humans in early phase clinical trials as a single agent. Recent research in drug delivery has defined conjugation strategies to deliver highly toxic substances to cellular compartments. Typically, these are highly toxic agents (e.g. diphtheria toxin, tubulysin) which are not targeted to a disease-specific mechanism. Rather, the targeting strategy is the single layer of therapeutic index expansion. Therefore, a pair of targeting strategies is proposed to deliver chromatin-targeted largazole derivatives to lymphoid malignancies, bridging advances in natural product chemistry and drug delivery.

Feasibility and Preliminary Studies

The use of Class I HDAC inhibitors broadly in cancer is supported in the literature, and a particularly strong rationale exists in acute leukemia. Lymphoid malignancies arise from deregulation of the MYC master regulatory transcription factor and oncogene, which functions to drive growth and survival gene regulatory pathways in collaboration with chromatin complexes. Aggressive diffuse large Bcell lymphoma (DLBCL) has a high rate of MYC amplification and overexpression, and the Burkitt sub-type is characterized by MYC rearrangement. T-cell leukemia is typified by alterations in NOTCH1, which drive MYC expression in greater than 60% of cases. Very recently, focal amplifications of the MYC enhancer region have been identified in acute myeloid leukemia (Shi, et al. 2013 *Genes & Dev* 27:2648-2662). Disruption of chromatin-dependent signaling from MYC to RNA polymerase II can be accomplished by abrogating pathways of histone lysine acetylation (Delmore, et al. 2011 *Cell* 146:903-916). Indeed, HDAC inhibition is accompanied by potent down-regulation of MYC, likely by redistributing enhancer factors genome-wide, as described above. A challenge to developing HDAC inhibitors such as largazole to target MYC in cancer is the narrow therapeutic index. Conjugation strategies to deliver unusually potent (pM IC50) Largazole derivatives to lymphoid cancer cells, the characterization of such compounds, and pre-clinical development is described as follows.

Delivery of Potent Largazole Derivatives Selectively to Tumor Cells Via Folic Acid Conjugation Lymphoid cancer cells are uniquely addicted to folate. The high rate of cellular turnover establishes a constant need for folate as a source of carbon for de novo ribonucleotide biosynthesis. In particular, purine biosynthesis is highly sensitive to the availability of free folate owing to the precursor requirements of thymidylate synthetase. This addiction created the first effective therapeutic intervention for lymphoid leukemia with the development of aminopterin (4-amino folic acid). The near chemical derivative methotrexate (4-amino, 10-methyl folate) is a cornerstone of lymphoid leukemia and lymphoma therapy. Folate is actively transported into cells via folate receptors, principally in adults by FOLR1. High affinity binding to folate and reduced folate derivatives occurs on the plasma membrane, upon which folate enters the cell in an energy-dependent manner for further metabolic processing. Elevations of FOLR1 on cancer cells has prompted the conjugation of folate to imaging agents and cytotoxins for the detection and treatment of cancer (Leamon, et al. 2001 *Drug Discov Today* 6:44-51). Folate-conjugation of thapsigargin can inhibit NOTCH-dependent activation of MYC in T-ALL. Synthesis of potent largazole analogs conjugated to folate are characterized in pre-clinical models of leukemia and lymphoma.

Figure 5A:
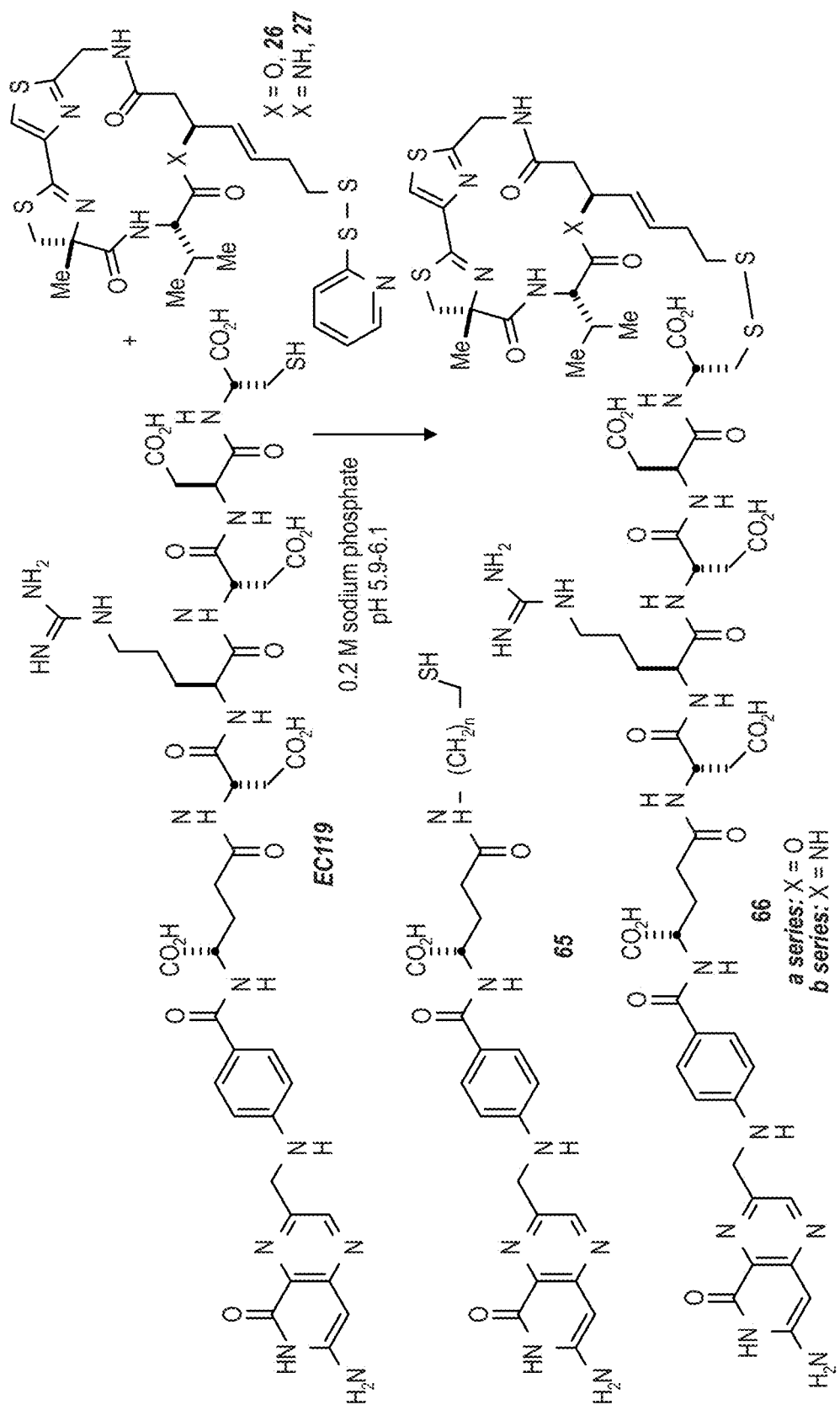
FIG. 5A shows the first portion of folate conjugation via disulfide or thiolester linker.
Figure 5B:
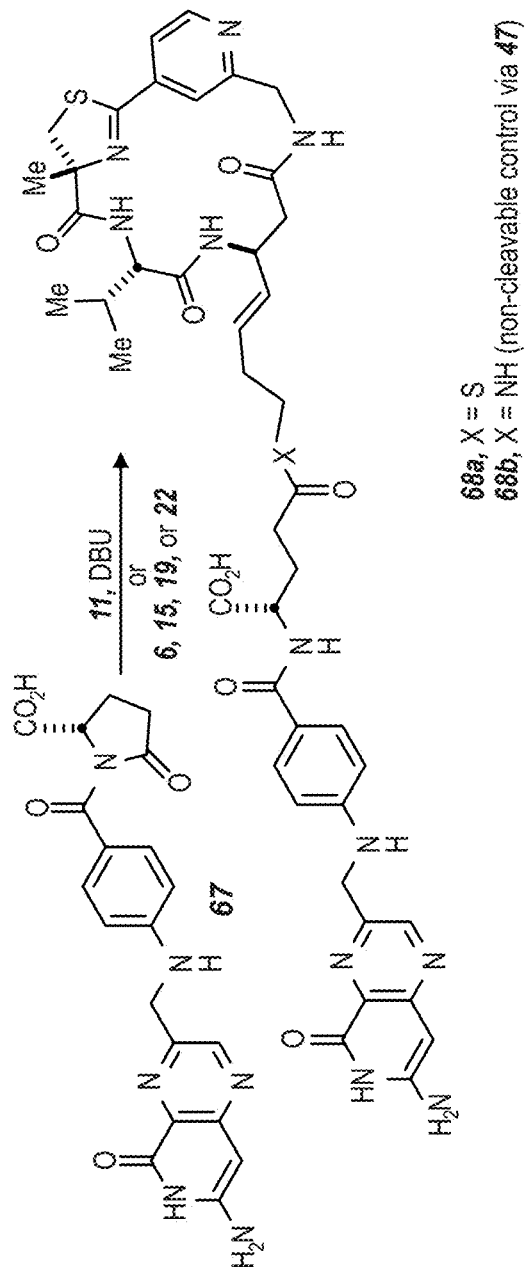
FIG. 5B shows the second portion of folate conjugation via disulfide or thiolester linker.
Figure 6:
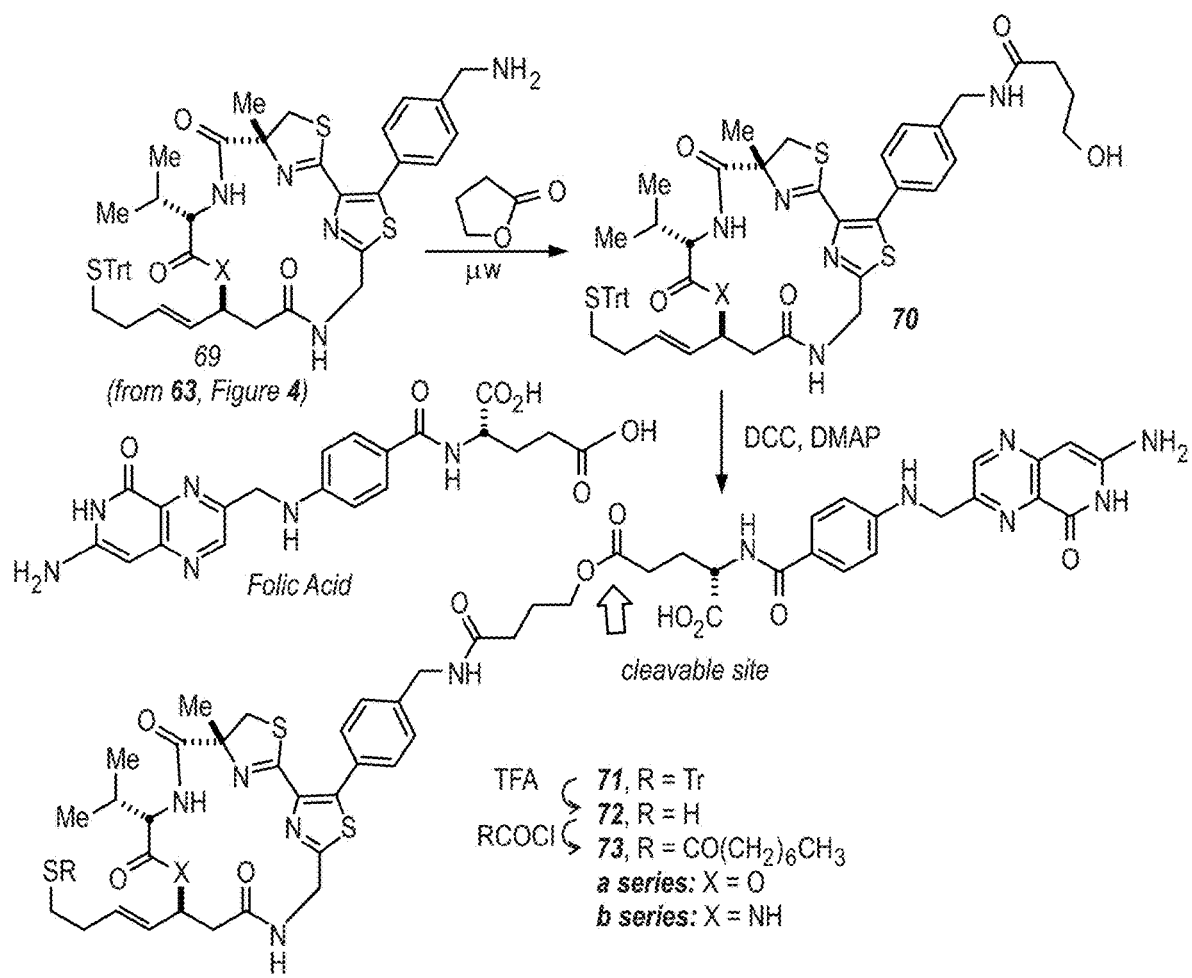
FIG. 6 shows folate conjugation via ester linker to cap group.
Figure 7A:
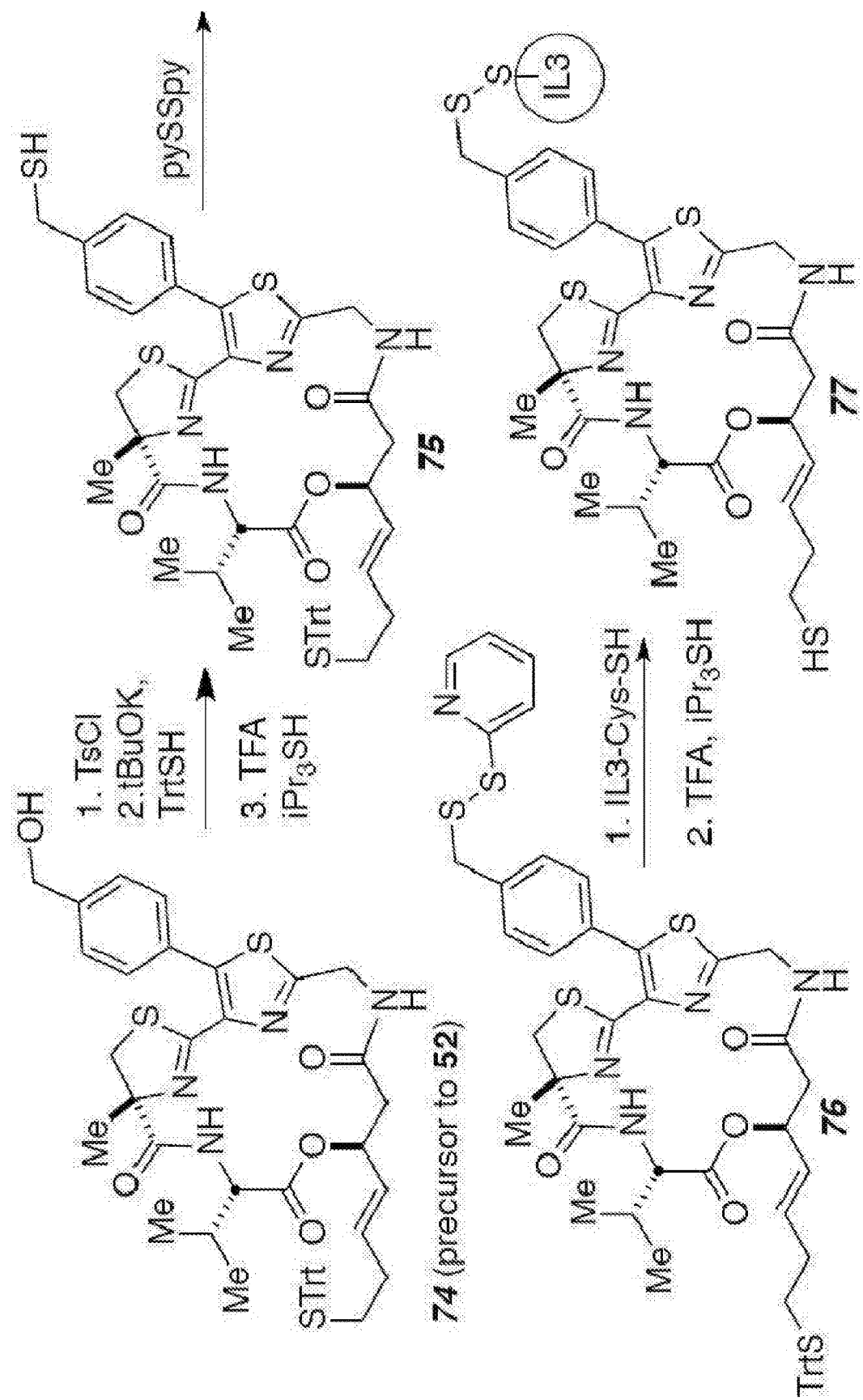
FIG. 7A shows cap-group strategy for IL3 conjugation.
Figure 7B:
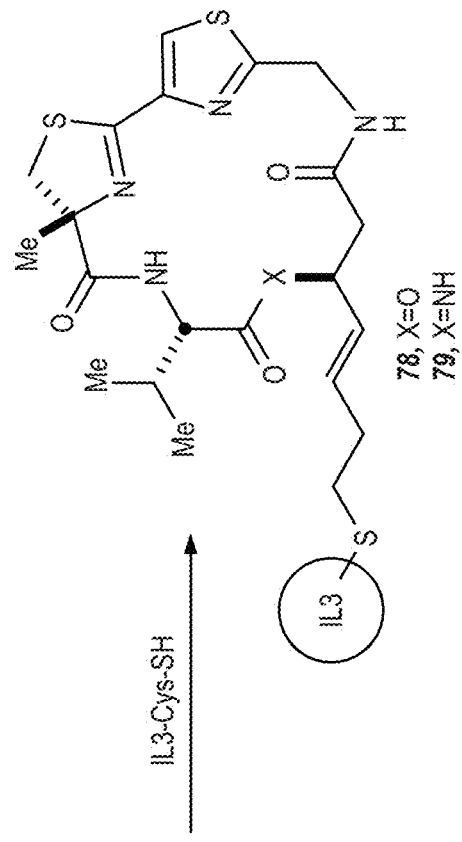
FIG. 7B shows zinc-binding arm strategy for IL3 conjugation.
Figure 7B:
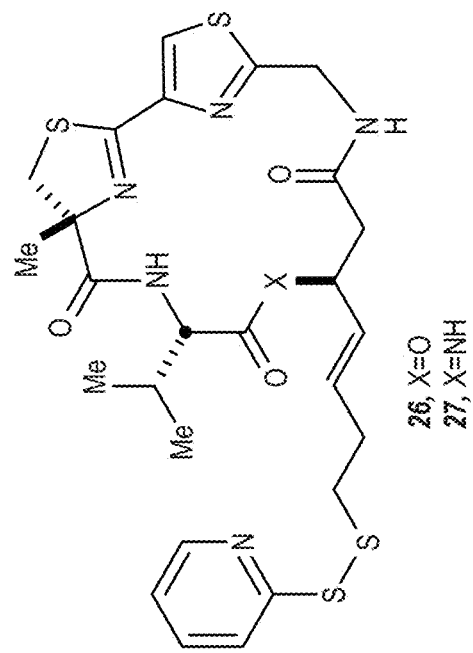

The activated, mixed pyridyl disulfides 26-30 have been prepared and can be used to directly cross-couple known folate-linked peptide EC11974 to prepare conjugate 66 (FIG. 5), and IL3 to prepare conjugates 78, 79 (FIG. 7). Simpler linkers to folate, such as that in 65 are also investigated. Selective coupling to the least-hindered carboxyl group of folic acid has been successfully used, and alternative activation strategies are known (Luo, et al. 1997 *J Am Chem Soc* 119: 10004-10013). Using chemistry developed to derivatize the thiazole ring, conjugation of folic acid can be accomplished via an in vivo cleavable ester linkage (72, 73, FIG. 6).

Additional folate conjugates contemplated by the inventors include:

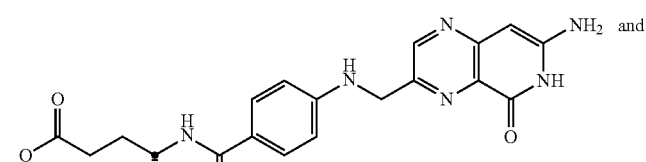

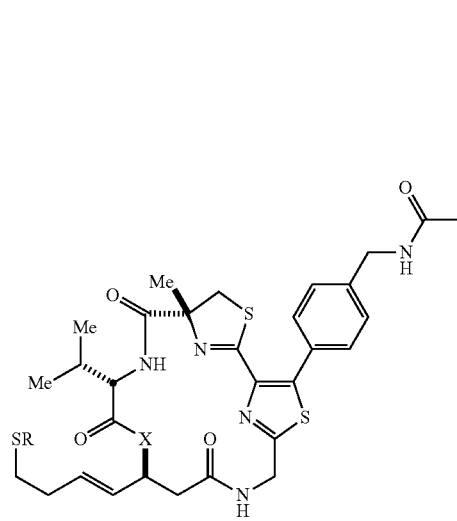

R = H, acyl
X = O; NH; NR

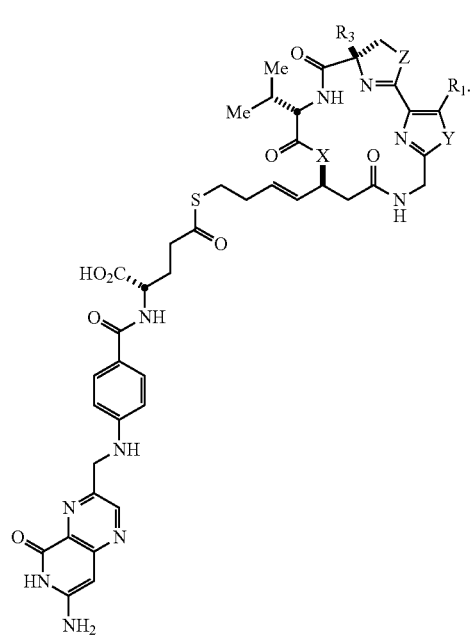

X = O; NH; NR
Y = S; O; NH; NR
Z = S; O; NH; NR

Additional IL-3 conjugates contemplated by the inventors include:

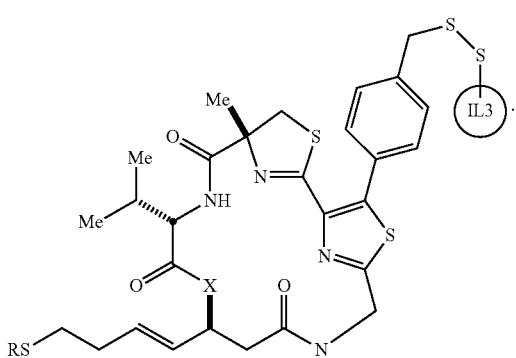

R = H, acyl
X = O; NH; NR

Pharmacokinetic Properties and Translational Research

Both in vitro and in vivo studies were performed for largazole, compounds 8-15, and 28. This data led to the conclusion that alteration of the macrocycle was both tolerable and beneficial to the therapeutic activity of the parent largazole. Significantly, the peptide isostere (7) shows increased selectivity towards Class I HDAC inhibition and the highest tumor growth inhibition of 66 percent when compared to largazole and largazole thiol, 34% and 44%, respectively. Although the distribution effect of these compounds is similar, there is a notable difference in drug exposure of ~30 percent for the peptide isostere. Follow-up PK studies on the proposed ligands and others help to improve the therapeutic impact of largazole.

All Largazole-folate derivatives are studied in a panel of mechanistic and translational assays. In brief effects on cell proliferation are determined using a panel of MYC-dependent leukemia and lymphoma cell lines: CUTTL1 (T-ALL), CAL1 (blastic plasmacytoid dendritic cell neoplasm;

BPDC), Daudi (DLBCL/Burkitt), and MM1.S (MM). Inhibition of growth over time and ATP content (ATPLite) are determined in comparative dose-response, with appropriate largazole, largazole-thiol, and free folate controls. Active compounds are studied for receptor-mediated uptake by competition with free folate. FOLR1-dependent uptake is assessed using shRNA knock-down (or CRISPR-Cas9 deletion) to FOLR1. Cellular response to drug therapy is assessed for cell cycle arrest (flow cytometry), apoptosis (Annexin V staining), and pharmacodynamics hyperacetylation of chromatin (immunoblot, immunofluorescence). Importantly, a subset of solid tumors overexpress FOLR1, and some re-express the fetal FOLR2 folate carrier. These focused studies can be augmented in blood cancers with cell line profiling to discover new opportunities for collaborative study in solid tumors.

Compounds exhibiting marked activity (nM) are advanced for consideration in vivo. In brief, pharmacokinetics and acute toxicity of test articles are assessed in Balb/c mice using established protocols. These data are utilized to establish a multiple dosing therapeutic strategy in efficacy studies in murine models of lymphoid malignancies. Largazole folate derivatives as therapeutic agents can be studied in dogs with spontaneous DLBCL (Childress, et al. 2014 *Am J Vet Res* 75:187-194). A biologically effective dose (BED) of 68a and/or 73b (selection to be made after PK study) is determined in dogs with spontaneous NHL through the completion of a pharmacodynamically and pharmacokinetically intensive phase-I trial. Changes in global histone acetylation constitute the primary biologic endpoint. Secondary endpoints include toxicity/adverse effects and changes in proliferation and apoptosis markers. The results allow efficacy studies of folate-conjugate (68a or 73b) in dogs with NHL and other FR-expressing malignancies. To determine initial tolerability and establish a starting dose for client-owned dog studies, a phase-0 microdose PK study is initially completed in 3 purpose-bred dogs. Briefly, these dogs receive a dose corresponding to approximately ⅒th of the allometric MTD based on preliminary murine tolerability studies. 72-hour plasma PK is then performed, and after a 2-week washout, a prediction of the biologically effective dose based on mouse exposure is extrapolated. After a 2-week washout, this calculated dose is administered daily for 3 days to the same dogs, PK repeated, and tolerability monitored through daily examinations and clinical pathology. Changes in PBMC histone acetylation are assessed after 3 days, using methods previously described (Wittenburg, et al. 2010 *Clin Cancer Res* 16:4832-4842).

Following completion of these studies and establishment of a tolerable canine starting dose, dogs with spontaneous NHL presenting as patients to the Animal Cancer Center are enrolled in a phase-I clinical trial of folate-conjugate, evaluating tolerability, PK and biologic effects (modulation of histone acetylation in tumor and PBMC, changes in proliferation/apoptosis markers) (Wittenburg, et al. 2011 *Cancer Chemother and Pharmacol* 67:83-92). Dose escalation is according to a standard 3+3 design, with evaluation of target modulation after 3 days of drug exposure. All adverse effects are prospectively graded (Vail, et al. 2004 *Vet Compar Oncol* 2:194-213). Together, these studies establish a new paradigm of HDAC inhibitor-based therapy for hematologic malignancies in animals and man.

Example 6. Delivery of Largazole-Derivatives Selectively to Lymphoid Cancer Cells Via IL3 Bio-Conjugation An alternative strategy to targeting largazole therapeutics to lymphoid malignancies may be achieved through bioconjugation. The established efficacy of biomolecules (e.g. immunoglobulins) conjugated to cytotoxic proteins, small molecules, or radioisotopes creates an opportunity for linkage of pathway-targeting agents for further disease-specific activity. Therefore, largazole-conjugated biologic agents are developed for preclinical study and eventual therapeutic development. Indeed, the zinc-binding thiol of largazole affords a unique opportunity for bioconjugation to cysteine residues on engineered proteins. Largazole-thiol can be conjugated to a lymphoid-specific cytokine (interleukin-3; IL3), as ALL and BPDC therapy. IL3 binds with high potency and specificity to CD123 (IL3 receptor), which binds CD131 as a heterodimer to transduce immune signals. The selective expression of CD123 on lymphoid cells led to the development of IL3-toxin conjugates (for example, diphtheria toxin; DT). These conjugates have demonstrated remarkable anti-leukemia efficacy in preclinical models, with limited toxicity in mice, leading to the clinical development of IL3-conjugated toxins as investigational agents. An advantage of small-molecule conjugation, as here, is the likely reduced risk of neutralizing antibodies.

To conjugate Largazole derivatives to IL3, recombinant human IL3 is first prepared in *E. coli*, engineered to possess a unique reactive cysteine at a permissive attachment site. Using the aforementioned chemistry developed to derivatize the thiazole ring, the mixed disulfide IL3-conjugate 75 is created. These targeted drug conjugates are prepared in both the depsipeptide (X═O) and peptide isostere (X═NH) series.

As above, IL3-largazole conjugates are studied for effects on cell proliferation using a panel of leukemia and lymphoma cell lines: CUTTL1 (T-ALL), CAL1 (blastic plasmacytoid dendritic cell neoplasm; BPDC), Daudi (DLBCL/Burkitt), and MM1.S (MM). Here, cell lines expressing (CAL1) and not expressing (MM1.S) the IL3 receptor are used to gauge IL3-mediated cytotoxicity. Inhibition of growth over time and ATP content (ATPLite) are determined in comparative dose-response, with appropriate largazole, largazole-thiol, and free IL3 controls. Active compounds are studied for receptor-mediated uptake by competition with free excess IL3. CD123 and CD131-dependent uptake are assessed using shRNA knock-down (or CRISPR-Cas9 deletion) to these receptors, using paired cell lines. Cellular response to drug therapy is assessed for cell cycle arrest (flow cytometry), apoptosis (Annexin V staining), and pharmacodynamics hyperacetylation of chromatin (immunoblot, immunofluorescence).

Data Interpretation

Folate-conjugated largazole likely enters cells in a FOLR1-dependent manner. However, limitations in potency, if any, may be related to the linker region of the molecule. In this case, alternative linker strategies are established, including increasing peptidyl character (Henne, et al. 2006 *Bioorg Med Chem Let* 16:5350-5355). Polycationic potential may also be employed to promote cell uptake. As described, for the folate- and IL3-conjugate research, cell line screening is used to provide new, unforeseen opportunities for development.

Example 7. Identification of Genetic Mechanisms of Resistance to Epigenetic HDAC Inhibitor Therapy In an effort to understand the mechanism of drug action, to anticipate clinical resistance to largazole therapy, and to explain clinical resistance to FDA-approved HDAC inhibitors, the genetic determinants of epigenetic HDAC inhibitor resistance are elucidated using haploid genetic screens and CRISPR resistance selections. To determine the genetic requirements for HDACi-induced cell death, two complementary genetic strategies are proposed: haploid genetic screens and a new technology employing Cas9-CRISPR genome editing.

Identification of Genetic Determinants of HDAC Inhibitor Efficacy Using Haploid Genetic Screens Haploid genetic screens performed in human cells afford a unique opportunity to characterize mechanisms of drug resistance. Large-scale insertional mutagenesis of (near) haploid cell lines, such as the KBM7 leukemia cell line, infected with a retroviral gene-trap vector effectively creates a heterogeneous mixture of knock-out cells (Carette, et al. 2009 *Science* 326:1231-1235). Gene-trap insertions occur genome-wide, preferentially at actively transcribed genes, disrupt the genomic locus, and confer truncations of the underlying transcript via a strong spice acceptor site coupled to a stop codon (Carette, et al. 2011 *Nature Biotechnol* 29:542-546). This represents a facile approach to generate true null-alleles and, thus, a straight-forward platform to create loss of function phenotypes that enable one to uncover genes that, upon knockout, confer resistance to largazole, as well as the FDA-approved, structurally divergent HDAC inhibitors SAHA and FK228.

Populations of $1\times10^8$ haploid cells are heavily mutagenized and the selective pressure of each agent listed above titrated to yield clonal outgrowth of about $2\times10^4$ resistant clones (FIG. 8A). This remarkable stringency of the selective pressure elicited distinguishes haploid genetics from genetic screening approaches based on barcoded libraries (exemplified below) and is, thus, best suited to uncover genes underlying a very pronounced phenotype and large amplitude in the modulatory effect. In line with that, haploid genetic screens have predominantly uncovered genes that are involved in pharmacological processes like cellular uptake mechanisms or drug metabolism. Given the structural diversity of Largazole, SAHA, and FK228, chemotype-selective gene-drug interactions are expected to elucidate the pathways involved in and required for compensatory mechanisms. Significance of enrichment of insertions in a given gene is calculated by comparing it to a much larger control dataset of a non-selected cell population. Candidate genes show a high enrichment in gene-trap insertions compared to the non-selected pool and are validated in different disease-relevant cell lines for cutaneous T-cell lymphoma (CTCL; Hut78, MJ) and multiple myeloma (MM1S, OMP-2) via CRISPR mediated loss of function, as well as overexpression studies.

Example 8. Identification of Genetic Determinants of HDAC Inhibitor Efficacy Using Functional Genetic Screening by CRISPR-Cas9

While haploid genetic screens have proven powerful enough to detect genes implicated in upstream processes such as cellular availability or drug metabolism, they are less powerful to detect modulator genes implicated in biological compensatory mechanisms. This relates to the stringency of the selective pressure commonly applied. Moreover, this strategy is limited to the two currently available human haploid cell lines KBM7 and HAP1 and can, consequently, not be readily performed in disease-relevant settings such as CTCL and MM. Thus, an orthogonal approach is proposed to identify genes that modify sensitivity to HDAC inhibition by functional genetic screening using the CRISPR-Cas9 system (FIG. 8C). The CRISPR-Cas9 system has been established as a powerful tool to selectively create complete null alleles by introducing indel mutations at a given locus in the human genome where a synthetic guide RNA (sgRNA) recruits the Cas9 protein to the site of interest (Hsu, et al. 2014 *Cell* 157:1262-1278). Subsequently, Cas9 executes sequence-specific nuclease function to introduce DNA double strand breaks that are repaired by the very error-prone process of non-homologous end-joining, leaving either insertions or deletions that eventually lead to a premature stop codon and a non-functional gene-product. Recently, this approach has been highly multiplexed in order to allow genome-scale, pooled screens where libraries of different sgRNAs are stably expressed, and abundance of any given sgRNA can be determined by highly parallel sequencing (Shalem, et al. 2014 *Science* 343:84-87).

The newest 120,000 sgRNA guide library has been successfully packaged using a second-generation vector system that allows for more efficient viral infectivity (Sanjana, et al. 2014 Nature Methods 11:783-784). This technology enables the identification of gene-drug interactions in the relevant cellular context and using a less stringent selective pressure. Thus, genome-scale CRISPR screens are conducted in CTCL (Hut78) and MM (MM1.S), representing indications where HDAC inhibitors are clinically approved, and acute leukemia (MV4; 11) to extend HDAC inhibitor therapy with largazole derivatives. Screens for MV4; 11 leukemia cells cultured in the DOT1L lysine methyltransferase inhibitor EPZ-5676 have already been completed (FIG. 8D), establishing the feasibility of this research. In brief, cells are first infected with a lentiviral construct expressing Cas9 and, subsequently, with a lentiviral pool of 120,000 sgRNAs at 800-fold coverage. The transduced cell population is expanded under selection for another 10 days to allow complete allele modification in the entire population. Subsequently, cell pools are selected with largazole, SAHA, and FK228 at concentrations representing the EC80 in a three-day dose-response experiment. Selective pressure is maintained for at least six population doublings to allow sufficient enrichment for sgRNAs that confer a growth advantage in the respective condition. The surviving fraction from each pool is serially tracked by massively parallel sequencing. Enriched loss-of-function alleles in the surviving fraction of treated pools are validated using six divergent sgRNAs in focused experiments and in an expanded series of cell lines. Rescue experiments are conducted by reintroducing the cDNAs encoding the respective candidate genes to show on-target effect.

Data Interpretation

Combining two orthogonal genetic screening approaches allows the identification of genes that are required to induce cell death after treatment with largazole and two structurally diverse Class I HDAC inhibitors, SAHA and FK228. Charting the genetic determinants of these agents should improve the understanding of the emergence of resistance to HDAC inhibition in cancer and deliver mechanistically understood biomarkers for clinical use. Differential analysis by intersecting the modulator genes of the individual HDAC inhibitors should distinguish between chemotype-selective, as well as chemotype-independent, gene-drug interactions. A global analysis of the gene-drug interaction networks is expected to shed light on the pathways governing HDAC inhibitor efficacy and aid in rationalizing strategies for drug combinations involving HDAC inhibitors. Additional established screening strategies may be pursued, such as genome-wide shRNA, siRNA, or ORFeome screens, to establish genetic contributors to drug resistance. These studies can be repeated when functionally validated folate-conjugated or IL3-conjugated largazole reagents are in-hand.

Example 9. Folate Receptor Expression in T-Cell Acute Lymphoblastic Leukemias (T-ALL)

T-cell acute lymphoblastic leukemias (T-ALL) are aggressive and uncontrolled proliferations of transformed T-cell progenitors. Multiple strategies have been developed to deliver highly toxic drugs for the treatment of cancer. Described herein is a general strategy for efficient drug delivery using a folate-based approach to transfer the inhibitor specifically to the cancer cells.

Folate enters cells by two mechanisms: 1) the reduced folate carrier (RFC), or 2) folate receptors (FR), virtually absent in normal cells, but with high affinity for folic acid. The FR family consists of four different proteins: FR1-4 or α, β, γ, δ (Antony, A. C. 1992 *Blood* 79: 2807-2820; Antony 1996 *Annual review of nutrition* 16:501-521). Several lines of evidence suggest that FRs are aberrantly expressed in rapidly dividing cells, including cancer cells (Lynn, et al. 2015 *Blood* 125:3466-3476; Ross, et al. 1999 *Cancer* 85: 348-357; Wang, et al. 2000 *Blood* 96: 3529-3536).

Figure 9:
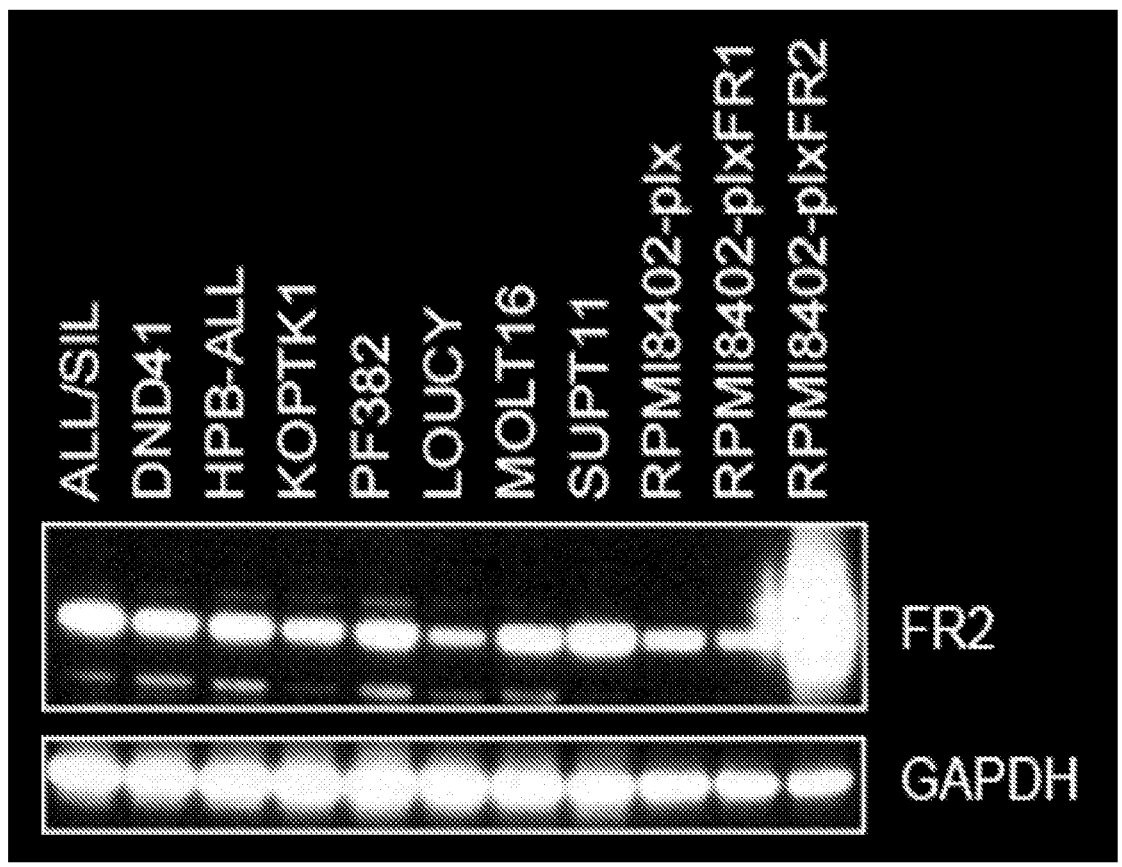
FIG. 9 shows a Western Blot in which expression of FR2 in T-ALL cell lines.
Figure 10A:
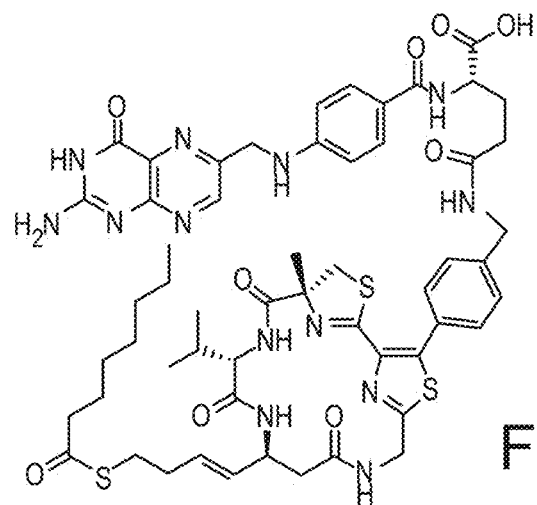
FIG. 10A schematically depicts Octanoylated Largazole Peptide Folate (Amide Linker) (relatively pure, HRMS) $C_{55}H_{67}N_{13}O_9S_3$, Mol. Wt.: 1150.3972, soluble in mixture of $CH_2Cl_2$-MeOH, or DMSO.
Figure 10B:
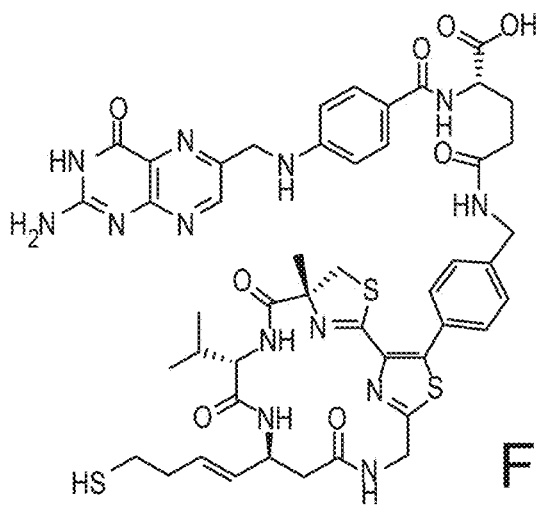
FIG. 10B schematically depicts Largazole Thiol Peptide Folate (Amide Linker) ca. 1.0 mg (crude) $C_{47}H_{53}N_{13}O_8S_3$, Mol. Wt.: 1024.2010, only soluble in DMSO.
Figure 10C:
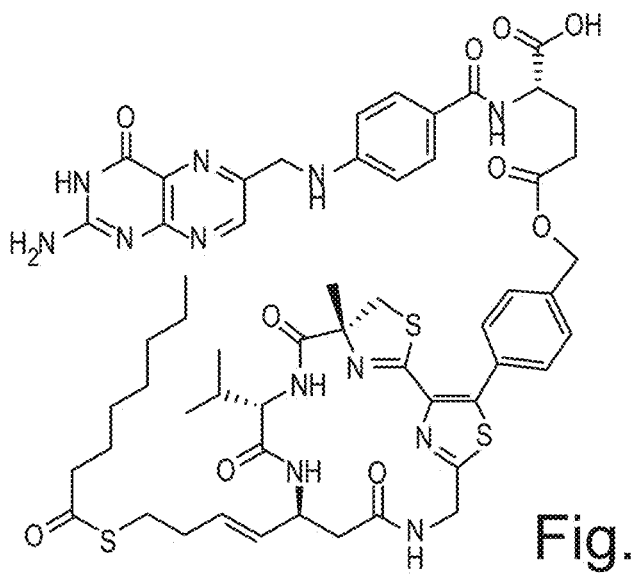
FIG. 10C schematically depicts Octanoylated Largazole Peptide Folate (Ester Linker) 1.6 mg (pure, $^1$H NMR, HRMS) $C_{55}H_{66}N_{12}O_{10}S_3$, Mol. Wt.: 1151.3819, soluble in MeOH, $CHCl_3$, DMSO.
Figure 11:
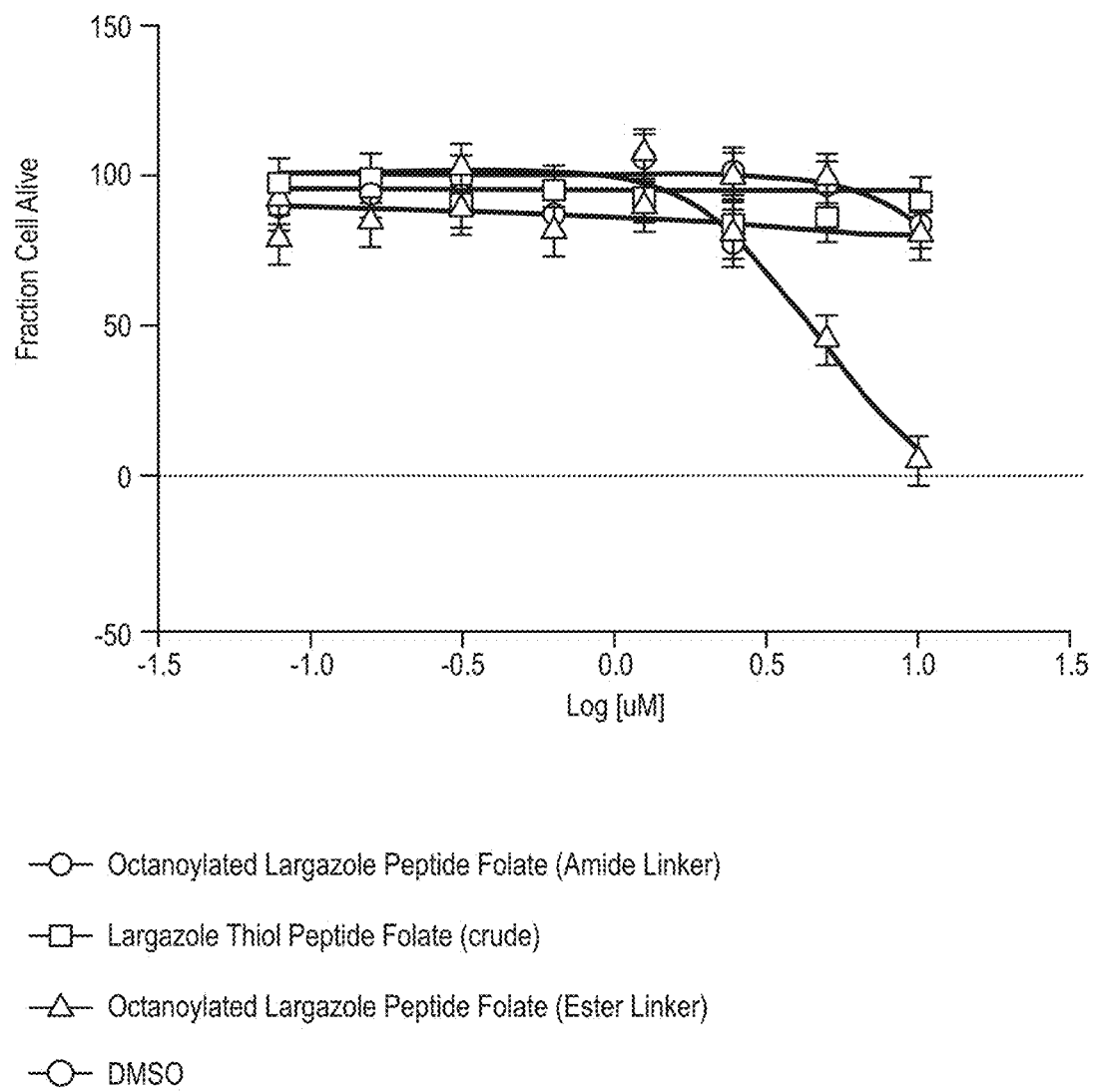
FIG. 11 shows a graph depicting the effect of Octanoylated Largazole Peptide Folate (Amide Linker), Largazole Thiol Peptide Folate (crude), Octanoylated Largazole Peptide Folate (Ester Linker) treatment on cell viability after 72 hours of treatment in NOTCH) mutated T-ALL cells (DND41).
Figure 12:
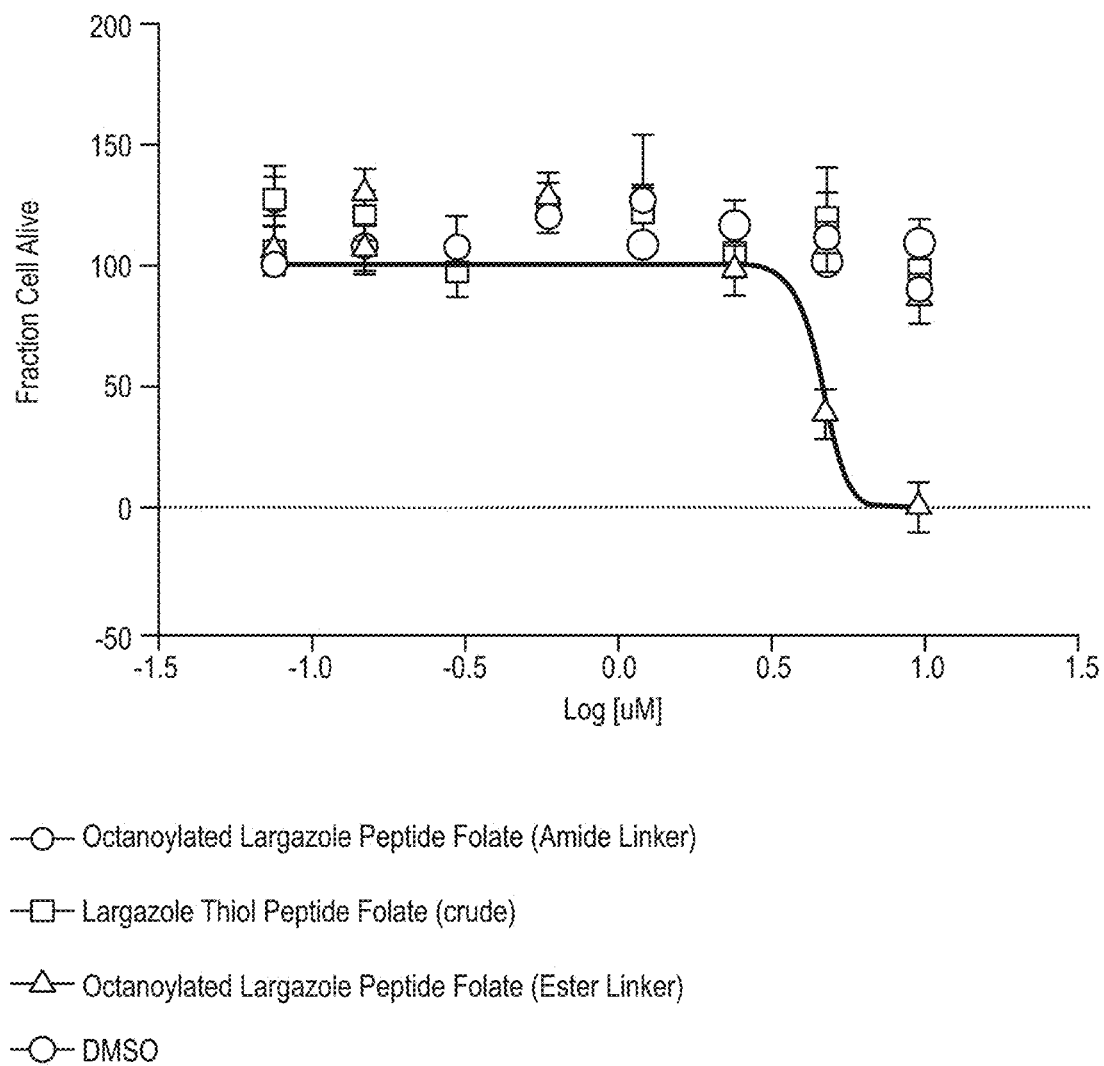
FIG. 12 shows a graph depicting the effect of Octanoylated Largazole Peptide Folate (Amide Linker), Largazole Thiol Peptide Folate (crude), Octanoylated Largazole Peptide Folate (Ester Linker) treatment on cell viability after 144 hours of treatment in NOTCH1 mutated T-ALL cells (DND41).
Figure 13:
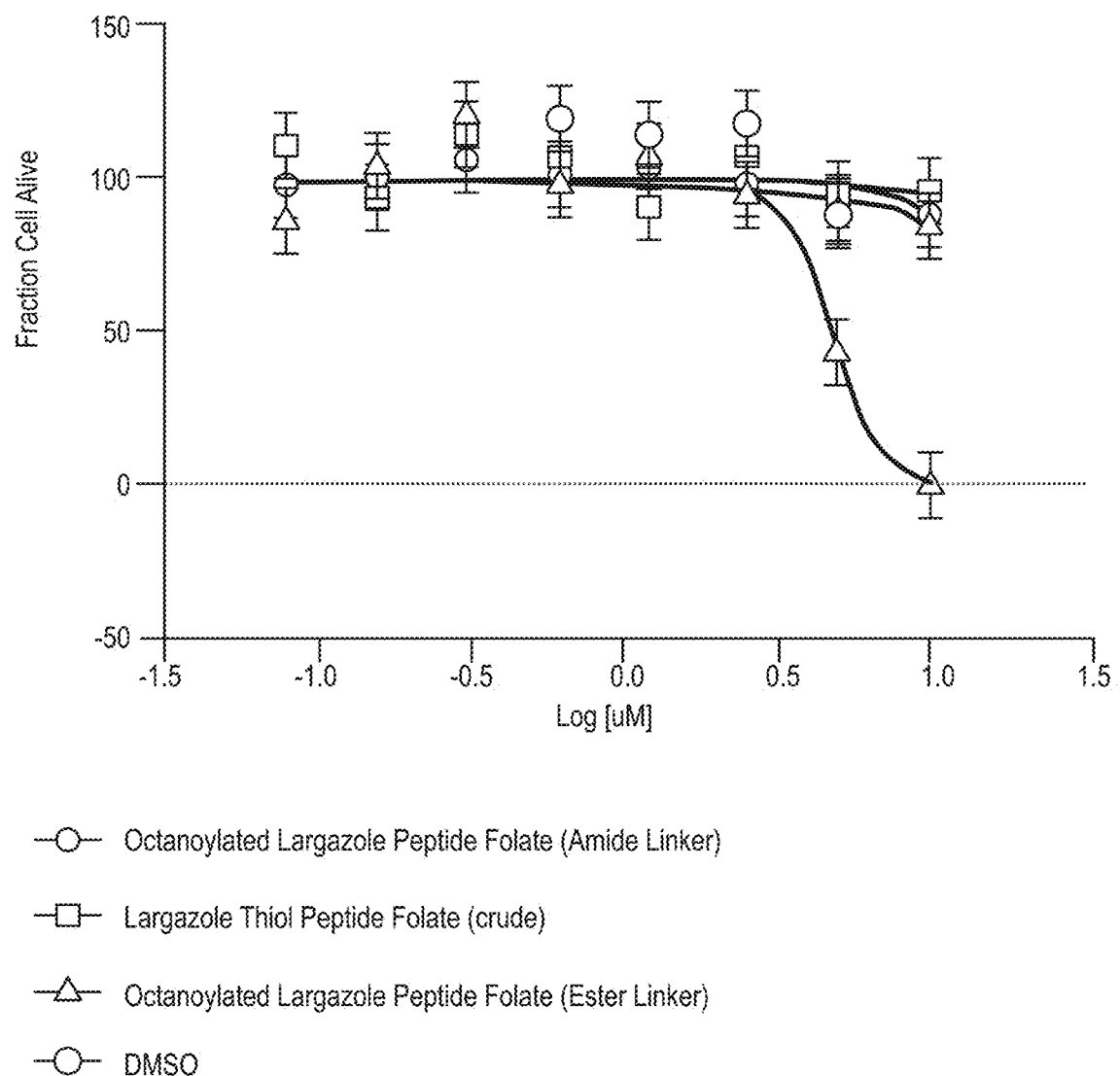
FIG. 13 shows a graph depicting the effect of Octanoylated Largazole Peptide Folate (Amide Linker), Largazole Thiol Peptide Folate (crude), Octanoylated Largazole Peptide Folate (Ester Linker) treatment on cell viability after 216 hours of treatment in NOTCH1 mutated T-ALL cells (DND41).
Figure 14:
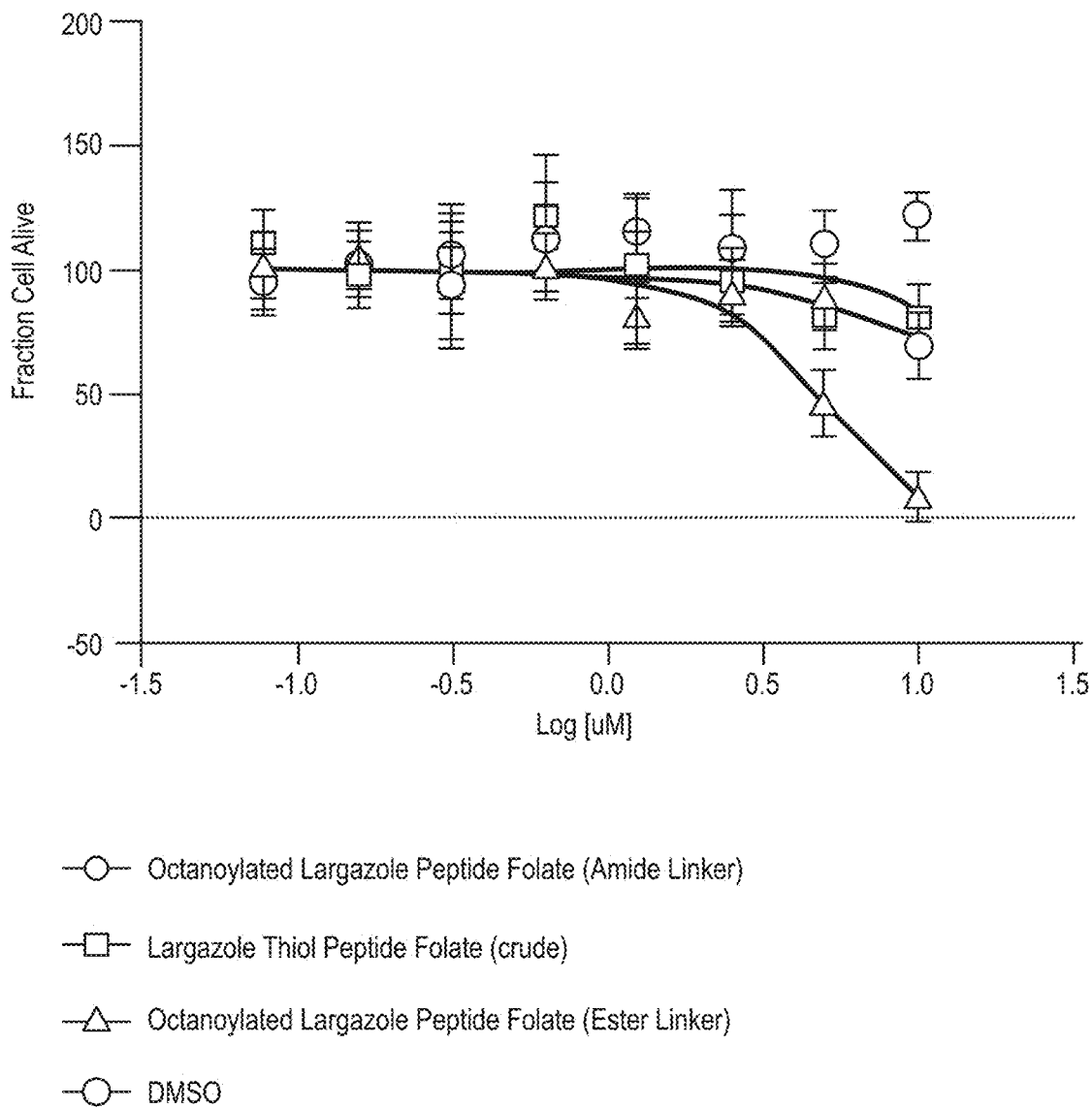
FIG. 14 shows a graph depicting the effect of Octanoylated Largazole Peptide Folate (Amide Linker), Largazole Thiol Peptide Folate (crude), Octanoylated Largazole Peptide Folate (Ester Linker) treatment on cell viability after 72 hours of treatment in NOTCH1 mutated T-ALL cells (ALL/SIL).
Figure 15:
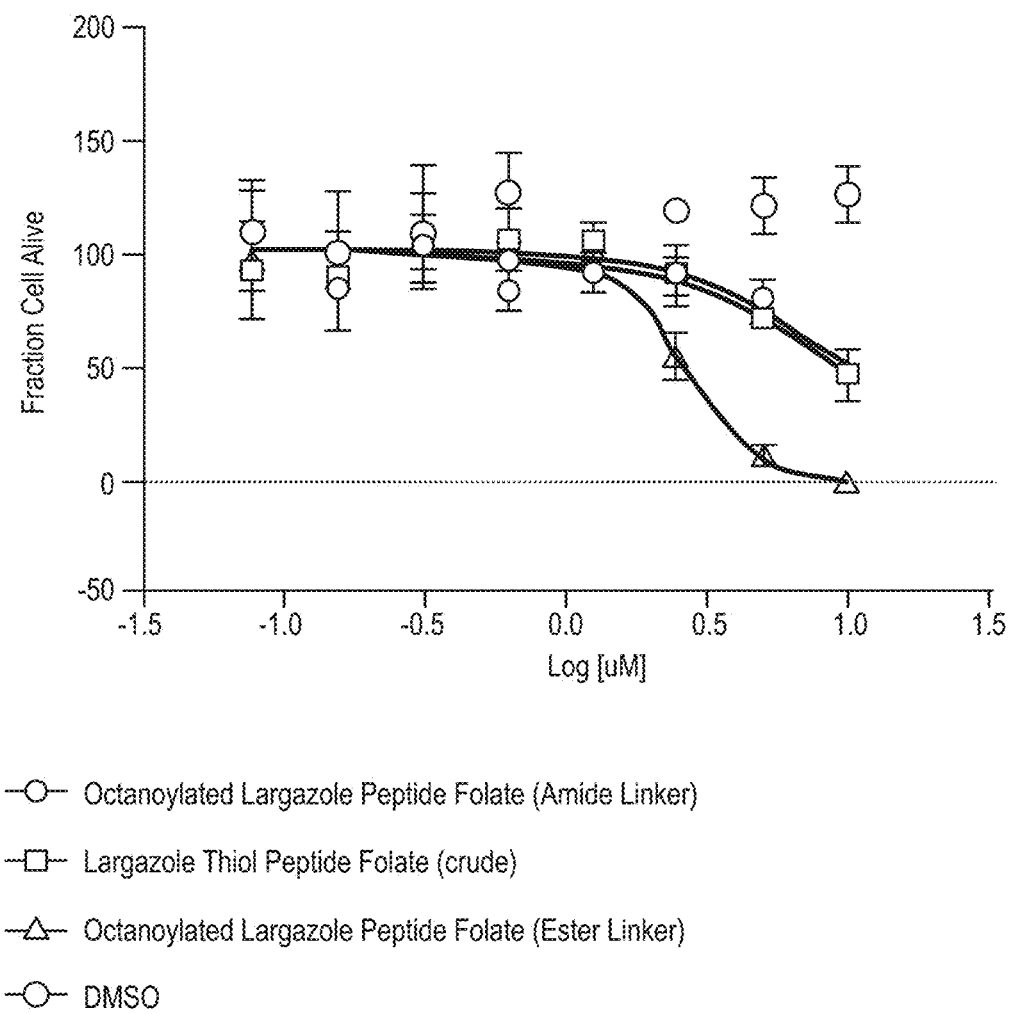
FIG. 15 shows a graph depicting the effect of Octanoylated Largazole Peptide Folate (Amide Linker), Largazole Thiol Peptide Folate (crude), Octanoylated Largazole Peptide Folate (Ester Linker) treatment on cell viability after 144 hours of treatment in NOTCH1 mutated T-ALL cells (ALL/SIL).
Figure 16:
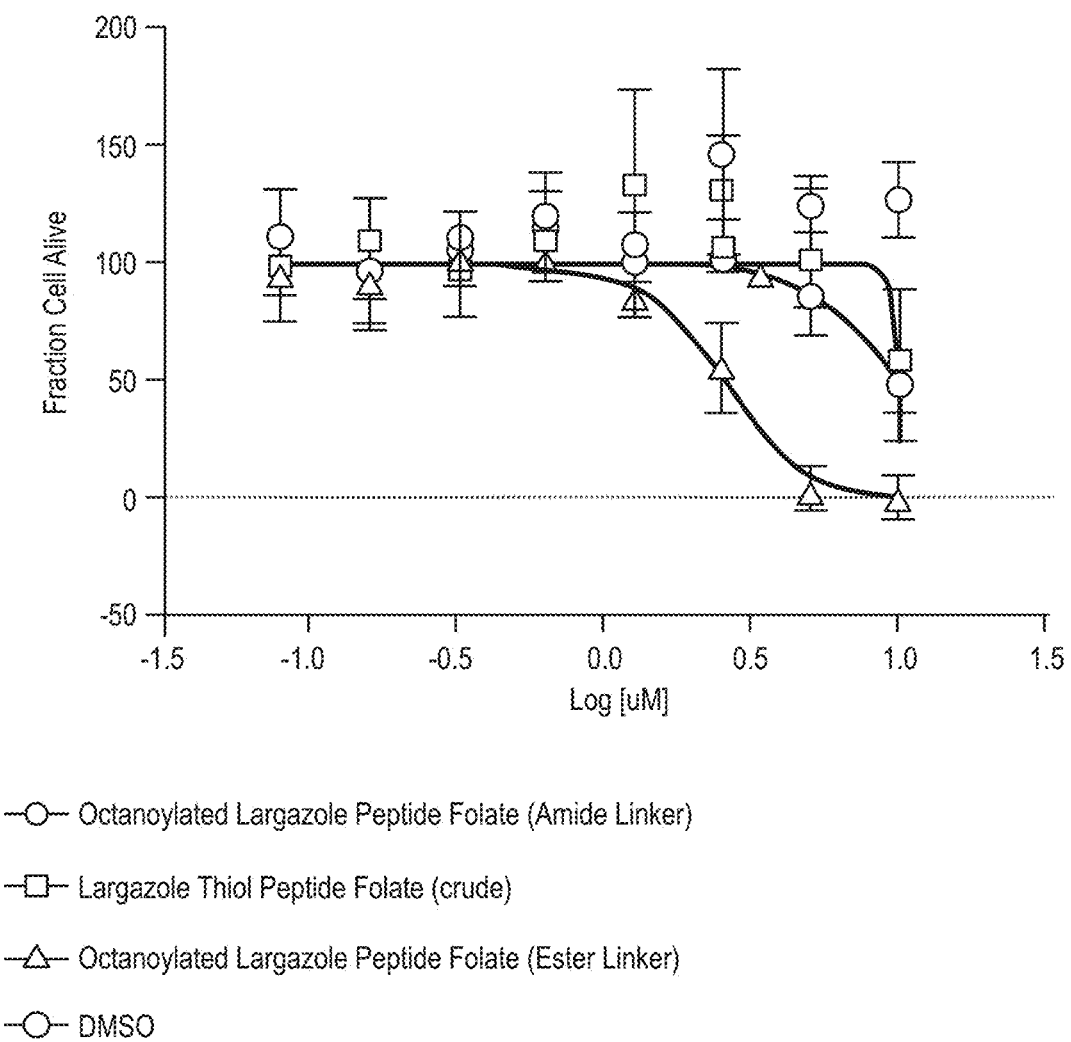
FIG. 16 shows a graph depicting the effect of Octanoylated Largazole Peptide Folate (Amide Linker), Largazole Thiol Peptide Folate (crude), Octanoylated Largazole Peptide Folate (Ester Linker) treatment on cell viability after 216 hours of treatment in NOTCH1 mutated T-ALL cells (ALL/SIL).

FR2 is constitutively overexpressed in activated macrophages and in acute myeloid leukemia (AML) (Pan, et al. 2002 *Blood* 100:594-602). Because of the high dependency of leukemia cells on folate metabolism, it was speculated that T-ALL cells might express FRs on their cellular surface. To test this hypothesis, the mRNA transcript levels of FR1 and FR2 were analyzed in 17 T-ALL cell lines and in 3 primary leukemia samples by RT-qPCR. FR2 is expressed in all of the leukemia samples, while FR1 expression appears to be measurable only in 2/20 cases tested (data not shown). Western blot (WB) of lysates from 9 T-ALL cell lines with the isoform-specific FR2 antibody demonstrated the expression of FR2 across all of the samples (FIG. 9).

Example 10. Synthesis of Largazole-Peptide Folate (Ester Linker)

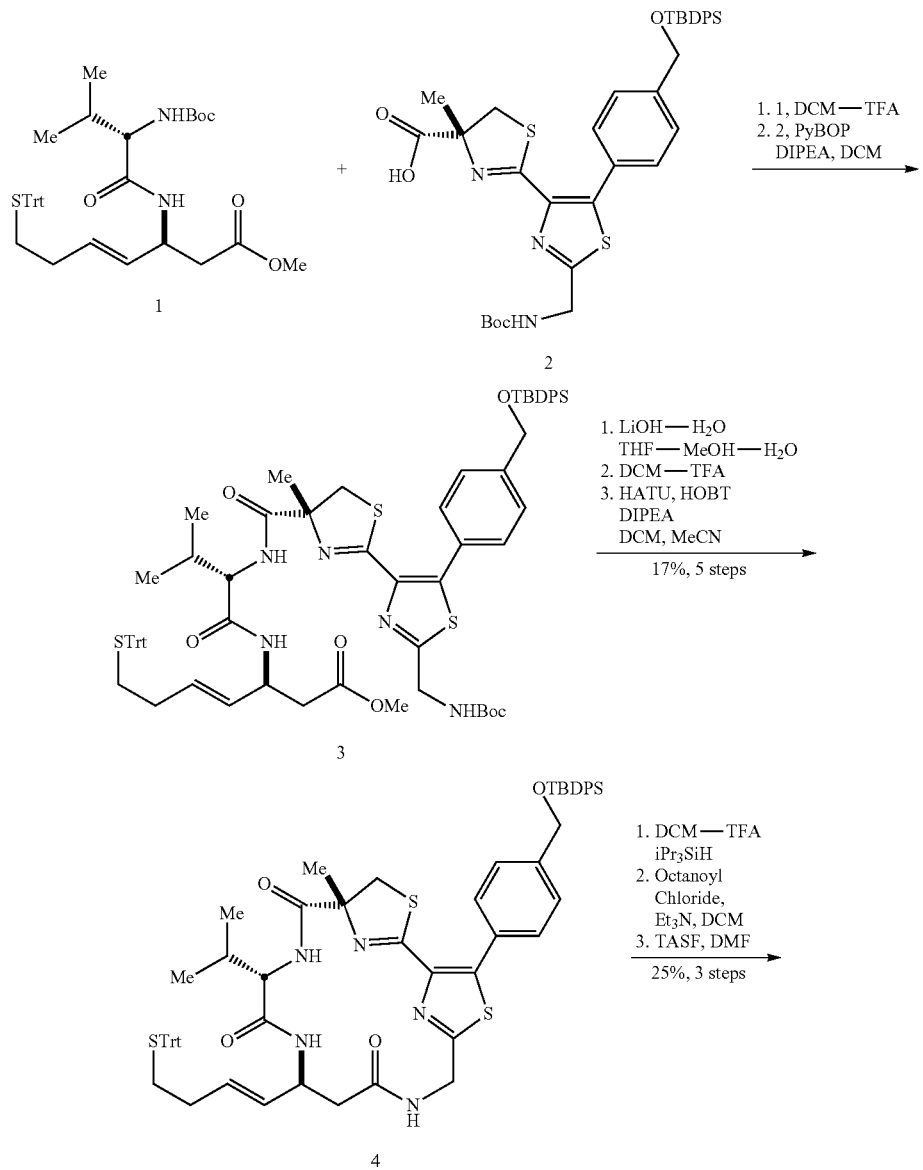

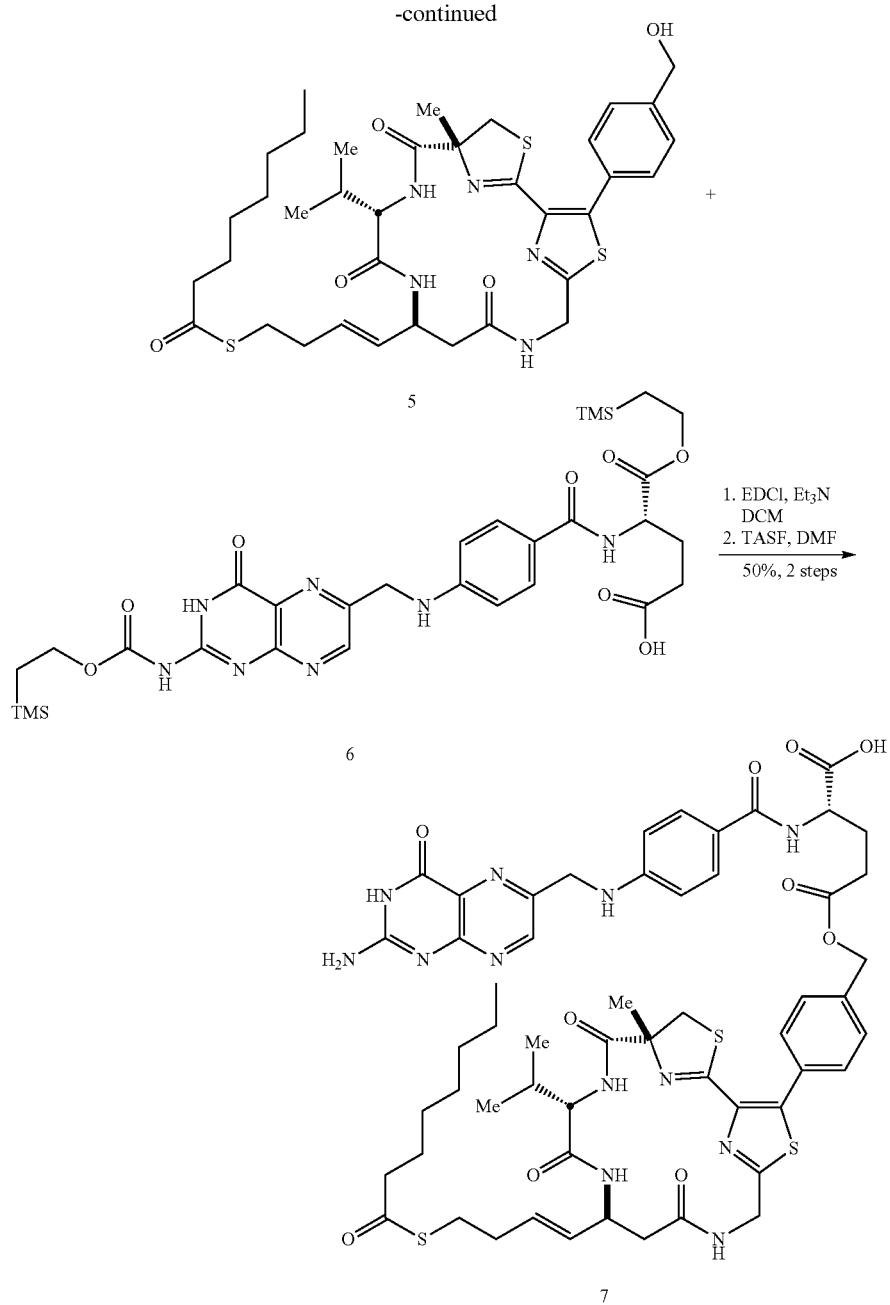
Preparation:
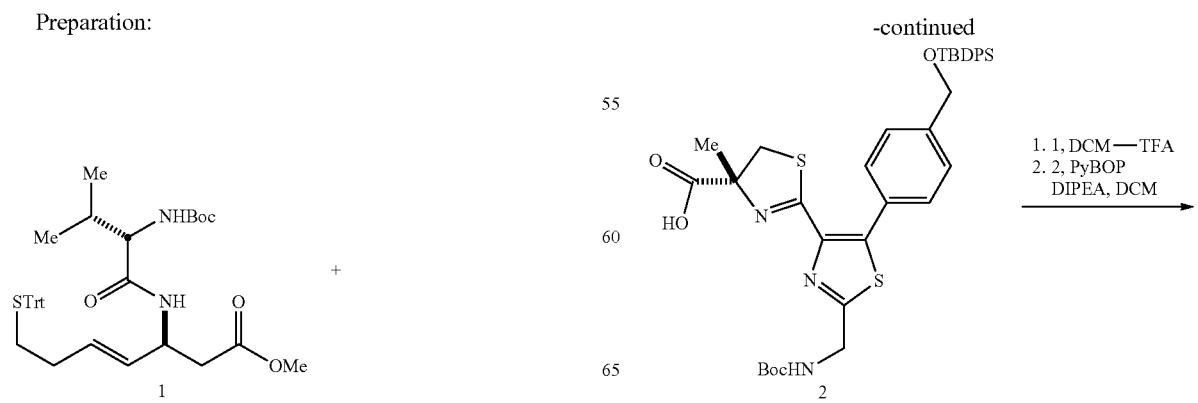

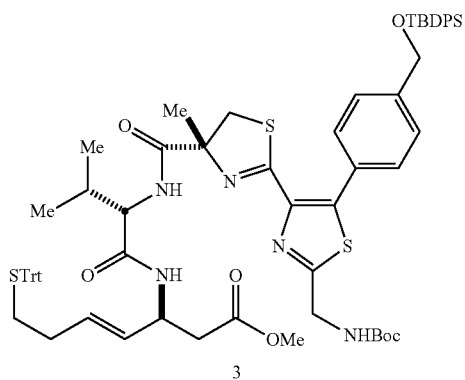

Boc-amine 1 (42 mg, 0.066 mmol) was dissolved in 2 mL of DCM, 0.2 mL of TFA was added to the solution at 0° C. The reaction was allowed to warm to room temperature and stirred for 2 hours. Solvents were evaporated and the crude amino acid was azeotroped with toluene (2×2 mL) to remove residual TFA. Acid 2 (46 mg, 0.066 mmol) was dissolved 5 mL of DCM. PyBOP (73 mg, 0.14 mmol) and DIPEA (63 μL, 0.36 mmol) were added, and the mixture was allowed to stir at room temperature for 20 minutes. To the resulting solution was added a DCM solution (totally 2 mL) of crude amine. After 4 hours, the reaction was concentrated and submitted to column chromatography, (16% to 33% ethyl acetate in hexane) to afford cyclization precursor 3 as a yellow foam.

$^1$H NMR (400 MHz, CDCl$_3$) δ 7.67 (d, J=6.4 Hz, 1H), 7.48 (d, J=8.2 Hz, 2H), 7.40-7.14 (m, 23H), 6.85 (d, J=8.5 Hz, 1H), 6.72 (d, J=8.6 Hz, 1H), 5.45-5.30 (m, 3H), 4.80 (s, 2H), 4.66 (dd, J=5.2, 3.2 Hz, 1H), 4.58 (d, J=5.8 Hz, 2H), 3.96 (dd, J=8.3, 7.1 Hz, 1H), 3.58 (m, 1H), 3.52 (s, 3H), 3.21 (dd, J=11.5, 11.3 Hz, 1H), 2.53-2.42 (m, 2H), 2.13-2.00 (m, 4H), 1.46 (s, 9H), 1.45 (m, 2H), 1.32-1.30 (m, 2H), 1.09 (s, 9H), 0.74 (d, J=6.7 Hz, 3H), 0.59 (d, J=6.7 Hz, 3H); $^{13}$C NMR (100 MHz, CDCl$_3$) δ 175.1, 171.4, 169.5, 167.3, 163.0, 155.7, 144.8, 143.8, 142.5, 141.8, 141.2, 136.1, 134.9, 133.2, 130.8, 130.9, 130.3, 130.1, 129.6, 129.5, 129.2, 128.9, 128.3, 127.2, 126.2, 125.9, 125.0, 85.4, 80.4, 77.9, 70.9, 66.5, 65.1, 58.4, 52.2, 51.0, 47.6, 46.5, 42.3, 41.0, 38.7, 31.3, 28.3, 26.8, 19.3; HRMS (ESI): m/z calcd. for C$_{69}$H$_{79}$N$_5$NaO$_7$S$_3$Si$^+$ (M+Na)$^+$ 1236.4803, found 1236.4726.

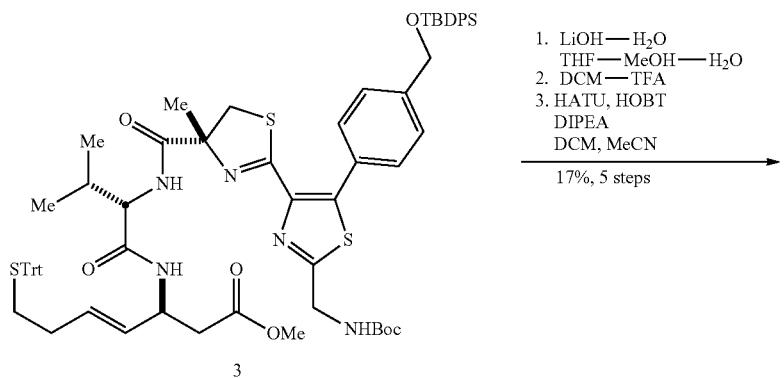

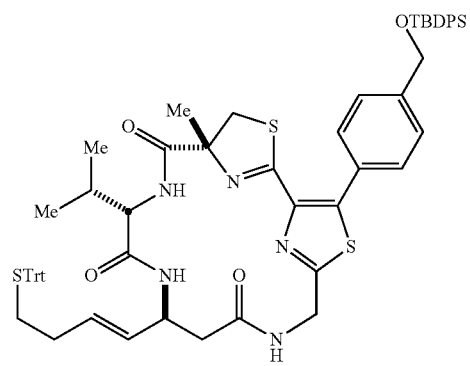

Acyclic precursor 3 obtained above was azeotroped with toluene (2×2 mL) to remove residual AcOEt, then combined with LiOH.H$_2$O (14 mg, 0.33 mmol). Solvent (THF MeOH.H$_2$O, 1+1+0.5 mL) was added, and the reaction mixture was allowed to stirred for 2.5 hours. The reaction mixture was diluted with 5 mL of water, then adjusted pH to 2 by using 1N HCl. Organic solvents were evaporated and the remained aqueous layer was extracted with DCM (3×5 mL), then dried over Na$_2$SO$_4$, filtered and evaporated. The crude acid was dissolved in 2.5 mL of DCM. 0.5 mL of TFA was added to the solution at 0° C. The reaction was allowed to warm to room temperature and stirred for 3 hours. Solvents were evaporated and the crude amino acid was azeotroped with toluene (2×2 mL) to remove residual TFA. The crude amino acid was then taken up in 70 mL of solvent (MeCN-DCM, 1:1, v/v) and DIPEA (0.1 mL, 0.57 mmol) was added. The resulting moderately opaque solution was allowed to stir for 10 min., before HATU (50 mg, 0.1:3 mmol) and HOBt (18 mg, 0.13 mmol) were added. The reaction was allowed to stir for 14 hours, then concentrated and redissolved in AcOEt. The solution was washed with saturated aqueous NH$_4$Cl, NaHCO$_3$ and brine, dried over Na$_2$SO$_4$, filtered, and concentrated under reduced pressure. The residue was purified by flash column chromatography on silica gel (0% to 16% AcOEt in DCM for the first column and 25% AcOEt in DCM for PLTC) to afford 12 mg (17% yield for 5 steps) of 4 as white foam.

$^1$H NMR (300 MHz, CD$_2$Cl$_2$) δ 7.71 (d, J=6.5 Hz, 4H), 7.47-7.21 (m, 22H), 6.67-6.63 (m, 3H), 5.58-5.42 (m, 3H), 5.07 (dd, J=17.4, 8.9 Hz, 1H), 4.86 (s, 2H), 4.48 (dd, J=4.6, 3.1 Hz, 1H), 4.20 (d, J=16.9 Hz, 1H), 3.72 (d, J=11.5 Hz, 1H), 3.28 (d, J=11.5 Hz, 1H), 2.68 (dd, J=14.9, 4.2 Hz, 1H), 2.56-2.33 (m, 2H), 2.34-2.00 (m, 6H), 1.80 (s, 3H), 1.12 (s, 9H), 0.75 (d, J=6.7 Hz, 3H), 0.45 (d, J=6.7 Hz, 3H).

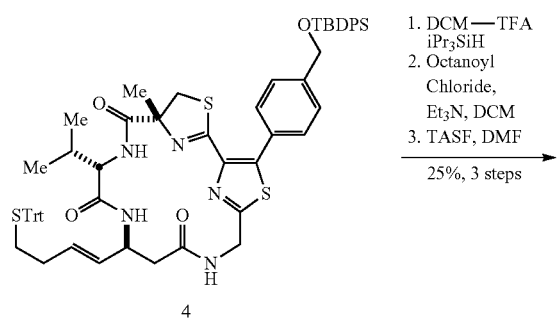

4

1. DCM—TFA iPr$_3$SiH
2. Octanoyl Chloride, Et$_3$N, DCM
3. TASF, DMF

25%, 3 steps

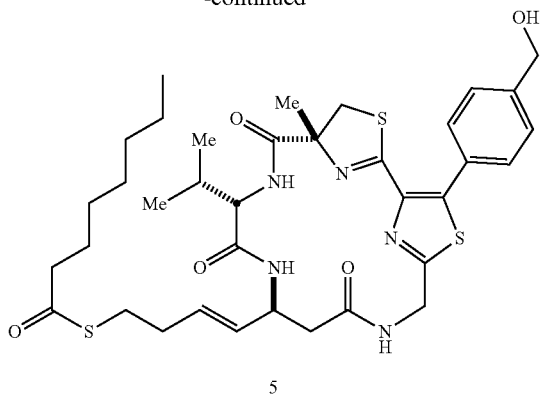

5

Trityl thiol 4 (12 mg, 11 μmol) was dissolved in 0.5 mL of DCM. 25 μL of TFA and iPr$_3$SiH (4.6 μL, 22 μmol) were added to the solution at 0° C. The reaction was allowed to warm to room temperature and stirred for 30 min. Solvents were evaporated and the residue was azeotroped with toluene (2×2 mL) to remove residual TFA.

Crude thiol was dissolved in 0.5 mL of DCM and cooled to 0° C. The mixture was successively treated with Et$_3$N (15 μL, 0.11 mmol) and octanoyl chloride (3.7μ, 22 μmol). The reaction was allowed to warm to room temperature and stirred for 2 hours. The reaction was cooled to 0° C. and quenched with 0.1 mL of 3N NH$_4$OH, before being concentrated and chromatographed (20% AcOEt in DCM) to provide thioester.

TBDPS-protected thioester (6.2 mg, 6.4 μmol) was dissolved in 0.5 mL of DMF and TASF (3.5 mg, 12.8 μmol) was added at room temperature. The reaction was allowed to warm to room temperature and stirred for 6 hours. Solvent was evaporated, and the residue was purified by flash column chromatography on silica gel (50% to 75% AcOEt in DCM) to afford 2.0 mg (25% yield for 3 steps) of 5 as yellow foam.

$^1$H NMR (300 MHz, CD$_2$Cl$_2$) δ 7.48-7.41 (m, 4H), 6.74-6.66 (m, 3H), 5.64-5.37 (m, 3H), 5.16-5.08 (m, 1H), 4.74 (s, 2H), 4.54 (dd, J=12.7, 0.9 Hz, 1H), 4.44 (dd, J=17.4, 1.4 Hz, 1H), 3.75 (d, J=11.8 Hz, 1H), 3.29 (d, J=11.8 Hz, 1H), 2.93-2.87 (m, 3H), 2.66-2.28 (m, 7H), 1.87 (s, 3H), 1.62-1.61 (m, 3H), 0.90-0.86 (m, 3H), 0.72 (d, J=6.8 Hz, 3H), 0.41 (d, J=6.8 Hz, 3H).

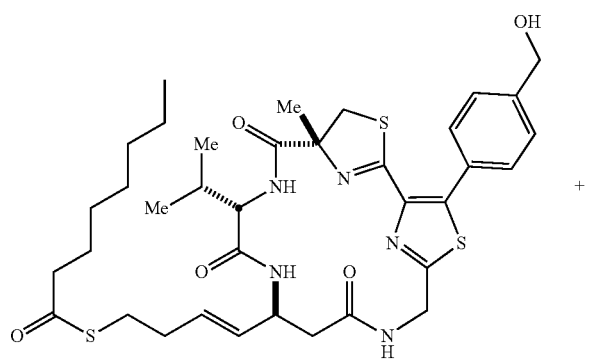

5

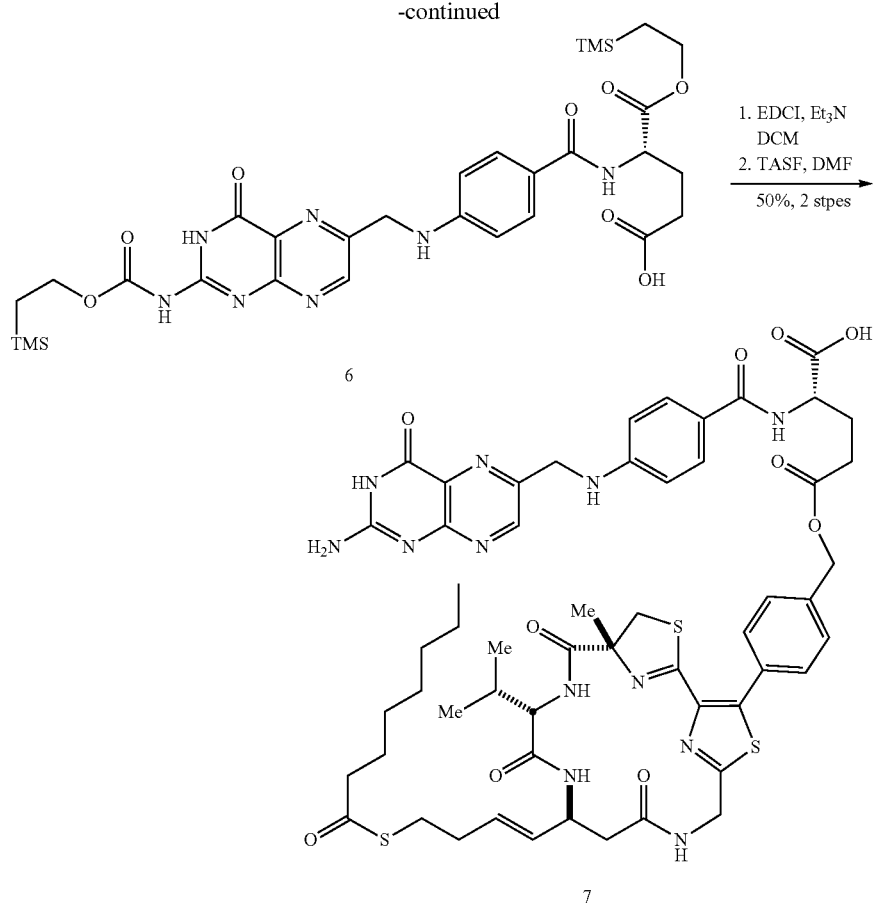

Benzyl alcohol 5 (2 mg, 2.7 μmol) was combined with protected folic acid (2.2 mg, 3.3 μmol). The mixture was then taken up in 0.5 mL, of DCM and Et$_3$N (2 μL, 14 μmmol) was added. To the resulting yellow solution was added trace DMAP and EDCI (1.1 mg, 5.5 μmol). The reaction was allowed to stir for 20 hours, then concentrated and purified by preparative TLC (DCM:AcOEt:MeOH=5:10:2, v/v/v) to afford 2.5 mg of coupling product. Protected folate obtained above (2.5 mg, 1.8 μmol) was dissolved in 0.3 mL of DMF and TASF (2.5 mg, 9 μmol) was added at room temperature. The reaction was allowed to warm to room temperature and stirred for 18 hours. Solvent was evaporated and the residue was purified by preparative TLC (25% MeOH in CHCl$_3$) to afford largazole peptide folate with an ester linker 7 (1.6 mg, 50% yield for 2 steps).

$^1$H NMR (400 MHz, CD$_3$OD-CD$_2$Cl$_2$=5:1, v/v) δ 8.68 (s, 1H), 8.55 (s, 1H), 7.66 (d, J=8.7 Hz, 2H), 7.46 (d, J=8.0 Hz, 2H), 7.39 (d, J=8.0 Hz, 2H), 6.70 (d, J=8.7 Hz, 2H), 5.65-5.53 (m, 3H), 5.17 (d, J=17.1 Hz, 1H), 5.07 (d, J=5.6 Hz, 2H), 4.36 (d, J=17.1 Hz, 1H), 3.98 (dd, J=13.2, 6.6 Hz, 1H), 3.69-3.59 (m, 2H), 3.39 (m, 1H), 3.05 (dd, J=14.5, 7.7 Hz, 1H), 2.90 (d, J=7.1 Hz, 1H), 2.69-2.29 (m, 6H), 2.15 (m, 1H), 1.86 (s, 3H), 1.63-1.61 (m, 2H), 1.28 (m, 10H), 0.88 (m, 3H), 0.72 (d, J=6.8 Hz, 3H), 0.39 (d, J=6.8 Hz, 3H); HRMS (ESI): m/z calcd. for C$_{55}$H$_{67}$N$_{12}$O$_{10}$S$_3^+$ (M+H)$^+$ 1151.4260, found 1151.4258.

Example 11. Synthesis of Largazole-Peptide Folate (Amide Linker)

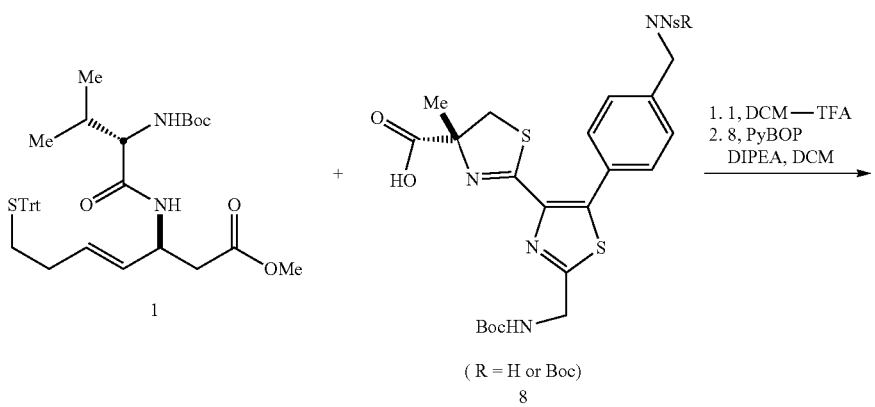

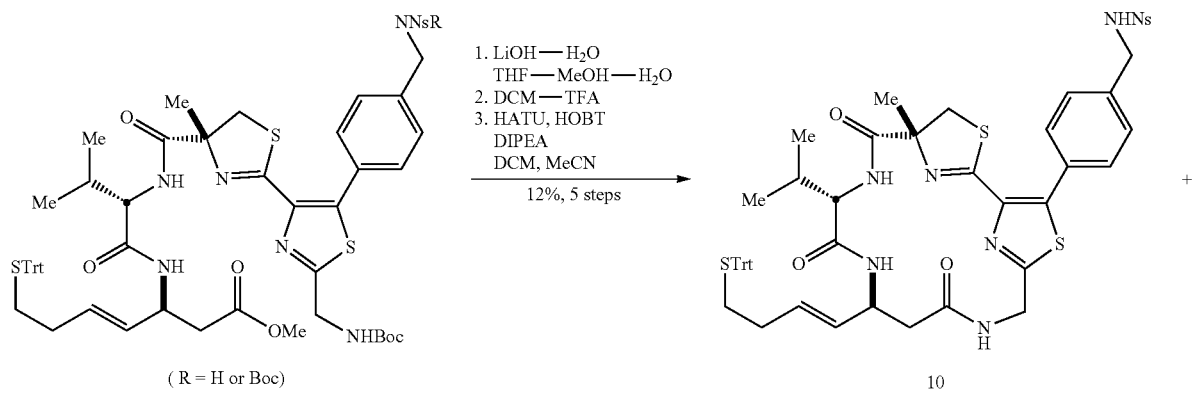
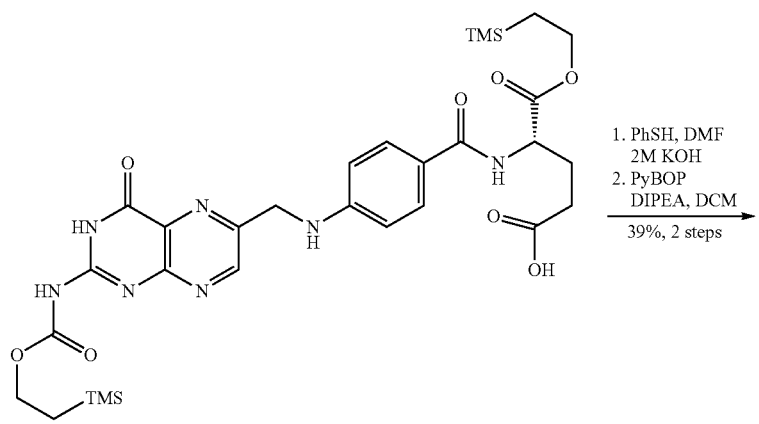
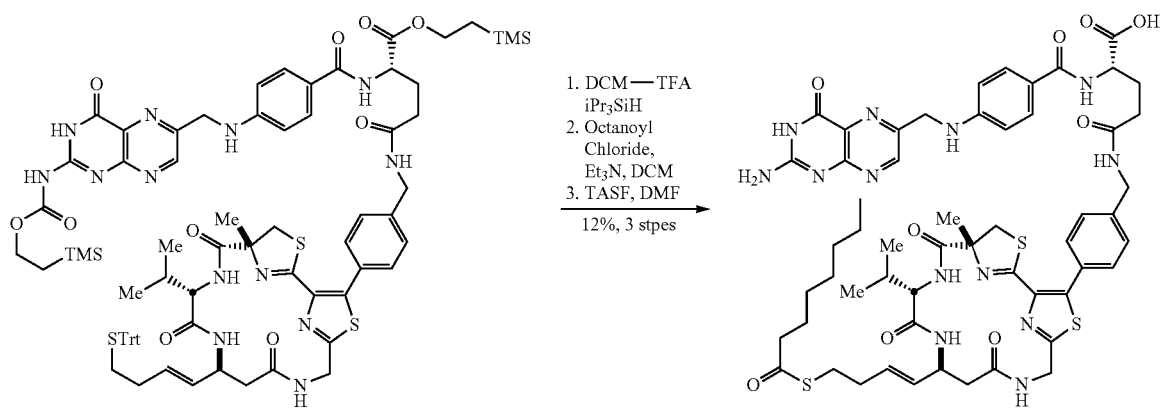

-continued

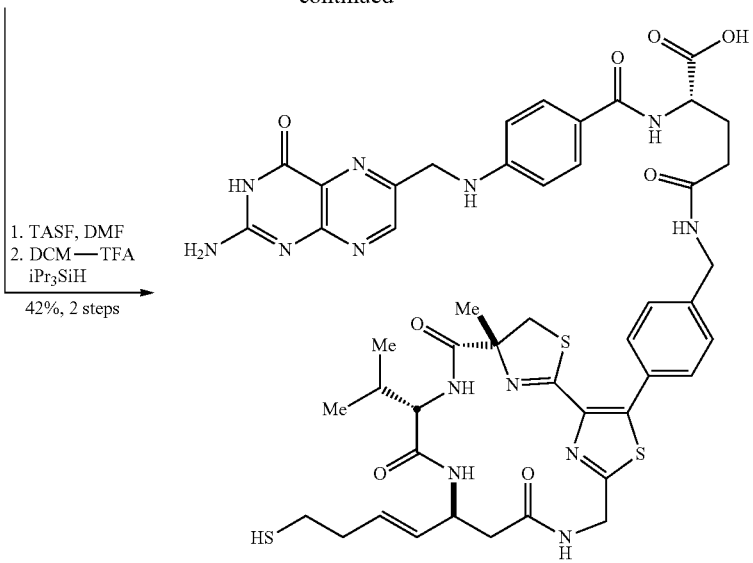

Preparation

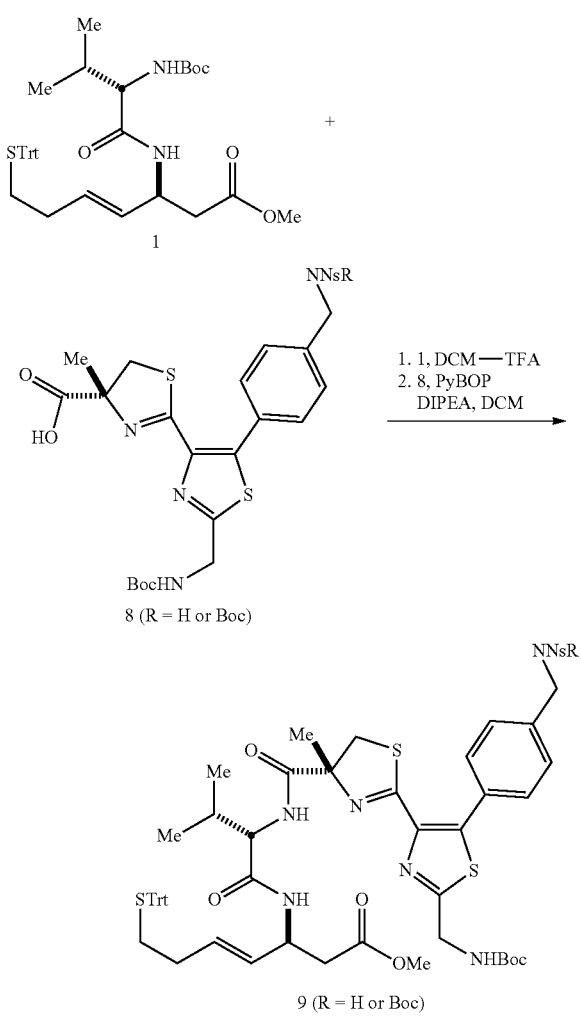

Boc-amine 1 (420 mg, 0.66 mmol) was dissolved in 10 mL of DCM, 1 mL of TFA was added to the solution at 0° C. The reaction was allowed to warm to room temperature and stirred for 2 hours. Solvents were evaporated, and the crude amino acid was azeotroped with toluene (2×2 mL) to remove residual TFA. Acid 8 (470 mg, ca. 0.72 mmol. R=Boc or H, ca 1:1) was dissolved 50 mL of DCM. PyBOP (730 mg, 1.4 mmol) and DIPEA (630 µL, 3.6 mmol) were added, and the mixture was allowed to stir at room temperature for 20 minutes. To the resulting solution was added a DCM solution (total 10 mL) of crude amine. After 4 hours, the reaction was concentrated and submitted immediately to column chromatography. (16% to 33% ethyl acetate in DCM) to afford macrocyclization precursor as a yellow foam.

For R=H, $^1$H NMR (400 MHz, CDCl$_3$) δ 8.04 (m, 1H), 7.67 (m, 1H), 7.61-7.58 (m, 2H), 7.36-7.34 (m, 10H), 7.27-7.14 (m, 13H), 6.63 (d, J=8.9 Hz, 1H), 6.46 (d, J=9.4 Hz, 1H), 5.87 (brs, 1H), 5.46 (ddd, J=15.4, 6.8, 6.3 Hz, 1H), 5.37-5.31 (m, 2H), 4.76 (m, 1H), 4.57 (d, J=6.0 Hz, 2H), 4.31 (m, 2H), 3.93 (dd, J=8.9, 8.6 Hz, 2H), 3.67 (m, 2H), 3.56 (m, 1H), 3.53 (s, 3H), 3.45 (d, J=11.6 Hz, 1H), 3.19 (d, J=11.6 Hz, 1H), 2.52 (m, 2H), 2.13-1.98 (m, 2H), 1.73 (m, 1H), 1.44 (s, 12H), 1.26-1.20 (m, 41H), 0.77 (d, J=6.7 Hz, 3H), 0.62 (d, J=6.7 Hz, 3H); $_{13}$C NMR (100 MHz, CDCl$_3$) δ 174.4, 171.7, 169.8, 167.4, 162.3, 148.0, 144.8, 141.6, 137.8, 134.2, 132.3, 130.6, 130.5, 130.3, 129.6, 129.5, 129.4, 127.8, 127.6, 126.5, 124.5, 85.5, 80.4, 66.5, 58.6, 51.7, 47.2, 47.1, 43.7, 42.3, 40.6, 38.6, 31.4, 31.3, 30.5, 29.6, 24.1, 19.2, 18.4, 18.1, 17.0, 14.1, 12.6: HRMS (ESI): m/z calcd. for $C_{59}H_{65}N_7NaO_{10}S_{4+}$ (M+Na)$_+$ 1182.3568, found 1182.3583.

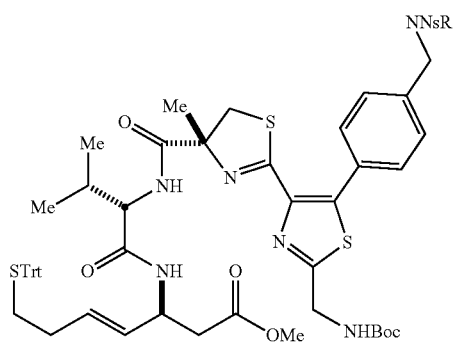

9 (R = H or Boc)

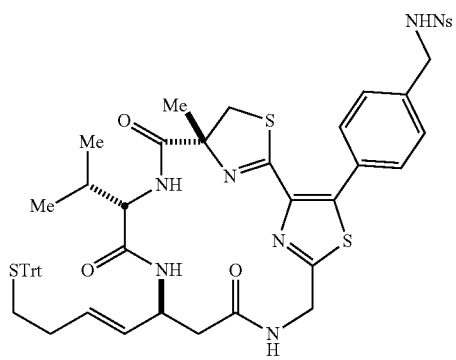

10

Acyclic precursor 9 obtained above was azeotroped with toluene (2×2 mL) to remove residual AcOEt, then combined with LiOH.H$_2$O (139 mg, 3.3 mmol). Solvent (THF-MeOH—H$_2$O, 2+2+1 mL) was added, and the reaction mixture was allowed to stirred for 2.5 hours. The reaction mixture was diluted with 10 mL of water, then adjusted pH to 2 by using 1N HCl. Organic solvents were evaporated, and the remained aqueous layer was extracted with DCM (3×10 mL), then dried over Na$_2$SO$_4$, filtered and evaporated. The crude acid was dissolved in 15 mL of DCM, 3 mL of TFA was added to the solution at 0° C. The reaction was allowed to warm to room temperature and stirred for 3 hours. Solvents were evaporated and the crude amino acid was azeotroped with toluene (2×2 mL) to remove residual TFA. The crude amino acid was then taken up in 700 mL MeCN, and DIPEA (1 mL, 5.7 mmol) was added. The resulting moderately opaque solution was allowed to stir for 10 min., before HATU (500 mg, 1.32 mmol) and HOBt (178 mg, 1.32 mmol) were added. The reaction was allowed to stir for 14 hours, then concentrated and redissolved in AcOEt. The solution was washed with saturated aqueous NH$_4$Cl, NaHCO$_3$ and brine, dried over Na$_2$SO$_4$, filtered, and concentrated under reduced pressure. The residue was purified by flash column chromatography on silica gel (0% to 33% AcOEt in DCM for the first column and 16% to 33% AcOEt in DCM for the second column then 33% to 66% AcOEt in DCM for PLTC) to afford 80 mg (12% yield for 5 steps) of 10 as white foam. (The product does dissolve in pure DCM and mixture of DCM/AcOEt, DCM/MeOH and CHCl$_3$/MeOH, but does not dissolve in pure CHCl$_3$, AcOEt or MeOH.

Use 66% AcOEt in DCM for developing TLC.)[α]$_{D30}$=+17.5° (C=0.257 in CH$_2$Cl$_2$); $_1$H NMR (400 MHz, CDCl$_3$) δ 8.03 (dd, J=7.5, 2.2 Hz, 1H), 7.82 (dd, J=7.8, 1.5 Hz, 1H), 7.72-7.68 (m, 2H), 7.31-7.18 (m, 23H), 6.92 (d, J=8.1 Hz, 1H), 6.72 (d, J=9.5 Hz, 1H), 6.63 (d, J=10.5 Hz, 1H), 6.21 (dd, J=6.4, 6.4 Hz, 1H), 5.52-5.40 (m, 2H), 5.07 (dd, J=17.5, 8.4 Hz, 1H), 4.86 (m, 2H), 4.47 (dd, J=10.4, 3.3 Hz, 1H), 4.35 (dd, J=6.4, 1.8 Hz, 1H), 4.24 (dd, J=17.5, 3.1 Hz, 1H), 3.71 (d, J=11.7 Hz, 1H), 3.24 (d, J=11.7 Hz, 1H), 2.67 (dd, J=14.6, 4.2 Hz, 1H), 2.52 (dd, J=14.8, 9.1 Hz, 1H), 2.37 (m, 1H), 2.20 (dd, J=7.7, 7.1 Hz, 2H), 2.02-1.98 (m, 2H), 1.77 (s, 3H), 0.87 (dd, J=6.9, 6.6 Hz, 1H), 0.71 (d, J=6.8 Hz, 3H), 0.40 (d, J=6.8 Hz, 3H); 173.7, 170.1, 170.0, 166.0, 147.7, 14.8, 142.1, 141.9, 138.4, 133.7, 133.5, 132.9, 130.8, 130.5, 130.2, 129.6, 129.5, 128.3, 127.9, 127.8, 126.6, 126.5, 125.2, 83.8, 66.9, 58.5, 48.2, 47.4, 44.6, 41.3, 40.5, 38.7, 32.3, 31.9, 31.7, 31.6, 30.0, 24.0, 19.7, 16.0, 14.3; HRMS (ESI): m/z calcd. for C$_{53}$H$_{53}$N$_7$NaO$_7$S$_4$ (M+Na)$_+$ 1050.2781, found 1050.2801.

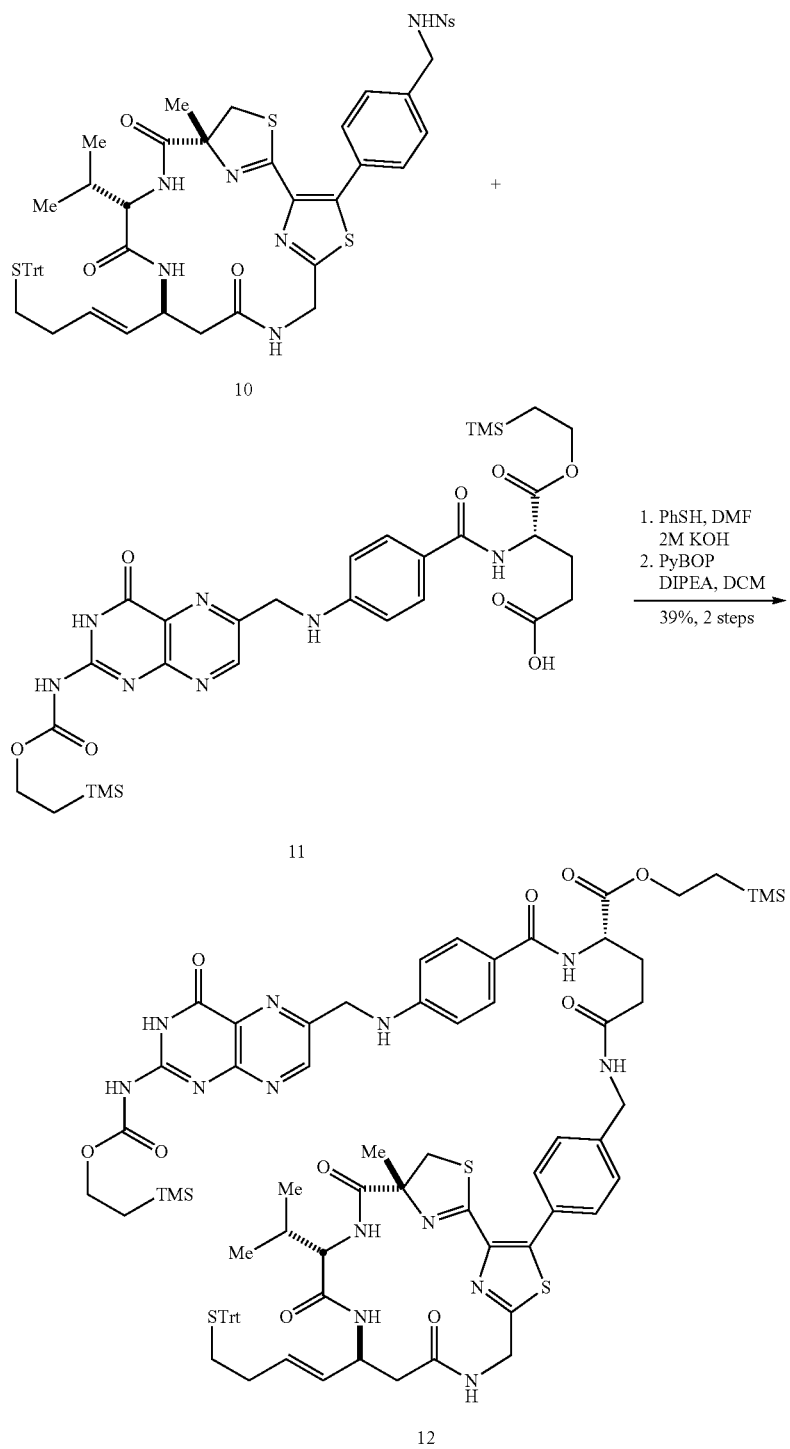

Thiophenol (72 μL, 0.7 mmol), KOH (25 mg, 0.45 mmol), water (220 μL) and DMF (9 mL) were combined to give a colorless solution. To 6.0 mg (5.8 μmol) of Ns amine 10 was added 0.5 mL of above solution at room temperature. The reaction was allowed to stir for 2 hours at 50° C. Then evaporated and submitted directly to column chromatography (33% AcOEt in DCM then 9% MeOH in DCM) to afford free amine as a yellow solid. Free amine obtained above, protected folic acid 11 (6.0 mg, 8.8 μmol) were combined. DMF (0.5 mL) was added, and the reaction was allowed to stir for 14 h, then concentrated under reduced pressure. The residue was purified by preparative TLC (4% MeOH in AcOEt for 3 times) to afford pure coupling product 12 (3.4 mg, 39% yield for 2 steps) as a yellow solid.

$^1$H NMR (400 MHz, CD$_3$OD) δ 8.83 (s, 1H), 7.66 (d, J=8.5 Hz, 2H), 7.37-7.18 (m, 19H), 6.80 (d, J=8.6 Hz, 1H), 6.70 (d, J=8.5 Hz, 2H), 5.50-5.27 (m, 3H), 5.13 (d, J=17.6 Hz, 1H), 4.63 (s, 2H), 4.56-4.35 (m, 5H), 4.23 (dd, J=7.0, 2.0

Hz, 2H), 3.63 (m, 1H), 3.40 (d, J=5.6 Hz, 1H), 2.69-206 (m, 10H), 1.80 (s, 3H), 1.13 (dd, J=9.0, 6.4 Hz, 1H), 1.00 (dd, J=10.2, 8.4 Hz, 1H), 0.69 (d, J=7.0 Hz, 3H), 0.35 (d, J=6.8 Hz, 3H); HRMS (ESI): m/z calcd. for $C_{77}H_{91}N_{13}NaO_{10}S_3Si_2{}^+$ (M+Na)$^+$ 1532.5610, found 1532.5621.

(10 μL, 52 μmol) and octanoyl chloride (4.2μ, 26 μmol). The reaction was allowed to warm to room temperature and stirred for 2 hours. The reaction was cooled to 0° C. and quenched with 0.1 mL of MeOH, evaporated and purified by preparative TLC (DCM:AcOEt:MeOH=5:10:2, v/v/v) to provide thioester. Protected folate obtained above (3.1 mg,

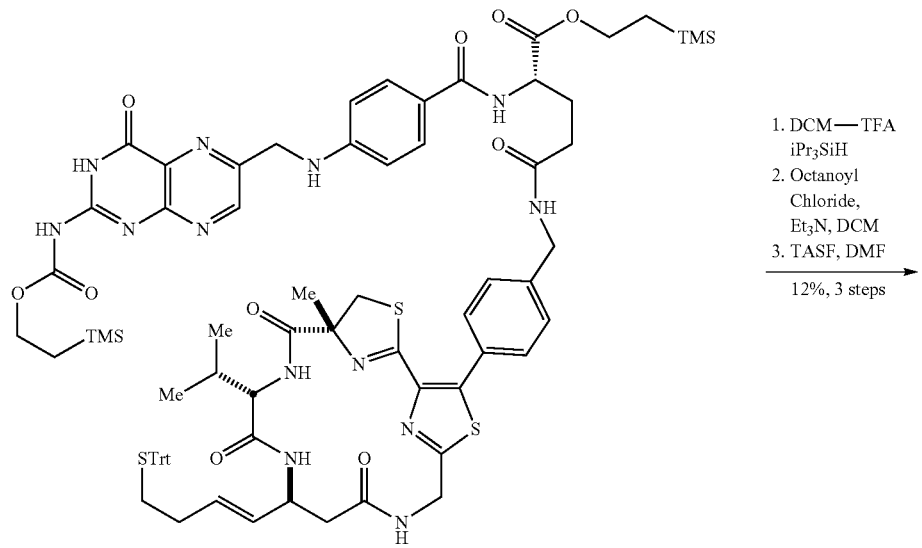

12

1. DCM—TFA
   iPr$_3$SiH
2. Octanoyl
   Chloride,
   Et$_3$N, DCM
3. TASF, DMF

12%, 3 steps

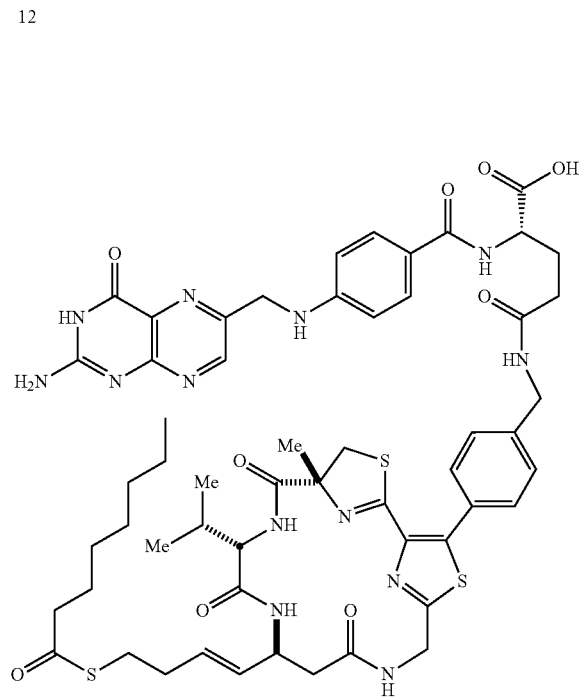

13

Trityl thiol 12 (7.8 mg, 5.2 μmol) was dissolved in 0.6 mL of DCM. 30 μL of TFA and iPr$_3$SiH (4 μL, 20 μmol) were added to the solution at 0° C. The reaction was allowed to warm to room temperature and stirred for 30 min. Solvents were evaporated, and the residue was azeotroped with toluene (2×2 mL) to remove residual TFA.

Crude thiol was dissolved in 0.5 mL of DCM and cooled to 0° C. The mixture was successively treated with DIPEA 2.4 μmol) was dissolved in 0.3 mL of DMF, and TASF (2.1 mg, 7.5 μmol) was added at room temperature. The reaction was allowed to warm to room temperature and stirred for 19 hours. Solvent was evaporated and the residue was purified by preparative TLC (25% MeOH in CHCl$_3$) to afford largazole peptide folate with an amide linker 13 (0.7 mg, 12% yield for 3 steps). HRMS (ESI): m/z calcd. for $C_{55}H_{67}N_{13}NaO_9S_3{}^+$ (M+Na)$^+$ 1072.4244, found 1172.4267.

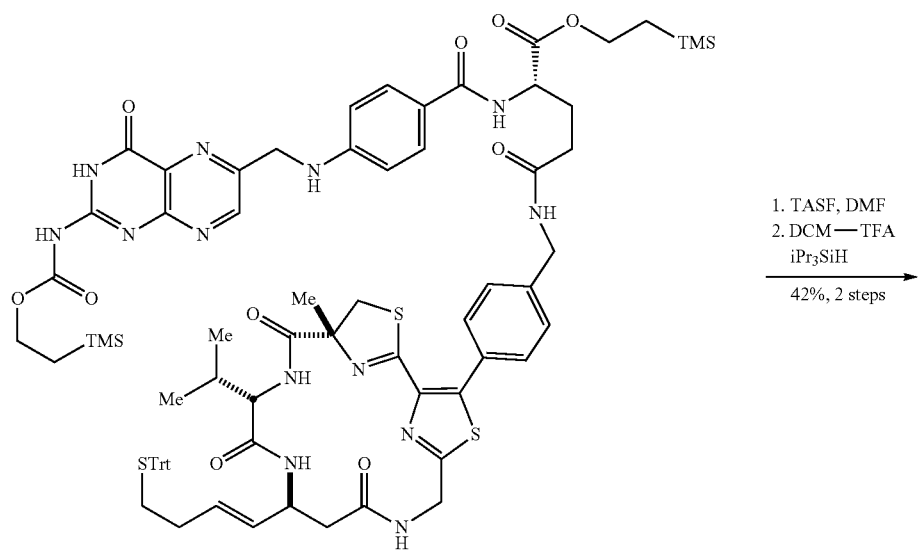

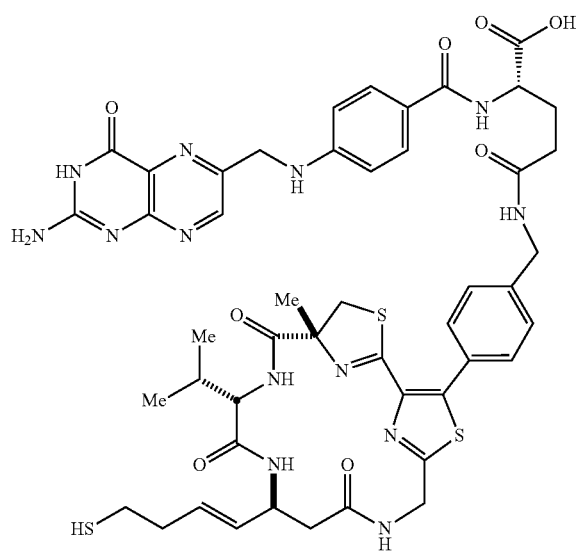

Protected folate 12 (3.4 mg, 2.3 μmol) was dissolved in 0.3 mL of DMF, and TASF (1.5 mg, 5.6 μmol) was added at room temperature. The reaction was allowed to warm to room temperature and stirred for 18 hours. Solvent was evaporated and the residue was purified by preparative TLC (9% MeOH in CHCl$_3$) to afford trityl largazole peptide folate.

Trityl thiol was dissolved in 0.6 mL of DCM and cooled to 0° C. TFA (30 μL) and iPr$_3$SiH (2.0 μL, 10 μmol) were added to the solution at 0° C. The bath was removed and the reaction was allowed to stir at room temperature for 1 h. Solvent was removed by argon flow and the residue 14 is taken crude for biological evaluation. (Solubility of the crude product in organic solvent is very poor. It is not soluble in DCM. AcOEt, MeOH, MeCN and mixture of them; it is slightly soluble in DMF, soluble in DMSO and mixture of DCM-TFA. It is also not soluble in water).

$^1$H NMR (crude, impure, 400 MHz, DMSO-D$_6$, all signals are broad) δ 8.58 (s, 1H), 8.43 (s, 1H), 8.30 (s, 1H), 7.56 (br, 2H), 7.38 (br, 2H), 7.26 (br, 2H), 6.85 (s, 1H), 6.78-6.71 (m, 11H), 6.59 (br, 2H), 5.54-5.36 (m, 3H), 4.43-4.15 (m, 4H), 2.22-1.86 (m, 3H), 1.66 (s, 3H), 0.60 (br, 3H), 0.36 (br, 3H).

Example 12. Killing of Leukemia Cell Lines that Over-Express the Folate Receptor To test the hypothesis that largazole folate-conjugated small molecules target T-ALL, dose-ranging ATP content assays were performed. T-ALL cell lines ALL/SIL and DND41 were treated with Octanoylated Largazole Peptide Folate (Amide Linker), Largazole Thiol Peptide Folate (Crude), Octanoylated Largazole Peptide Folate (Ester Linker) in 384 well plate format (500 cell/well) for 3, 6, and 9 days at concentrations ranging from 10 μM to 0.078 μM. Next, an ATP-based assay (CellTiter-Glo, Promega®) was used to calculate the half-maximal inhibitory concentration ($IC_{50}$) of cell viability. Graphs were plotted as a fraction of cells alive (y-axis) using Prism GraphPad 6 software and drug doses expressed as Log [μM] (x-axis).

As demonstrated in FIGS. 11-16, treatment with Octanoylated Largazole Peptide Folate (Ester Linker) was associated with loss of cellular viability in T-ALL.

The invention claimed is:

1. A compound of Formula (B)

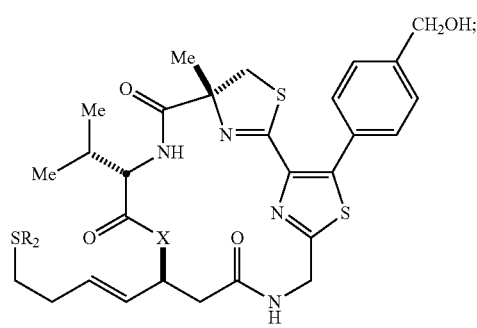

wherein X=NH, or NR, wherein R is H or lower alkyl; wherein $R_2$=H, acyl, or cleavable $SR_5$, wherein $R_5$=folate, methotrexate, cytokines, peptide, carbohydrate, or another molecule of the same (i.e., resulting in a homodimer); or a pharmaceutically acceptable salt, solvate, clathrate, or stereoisomer thereof.

2. A compound of Formula (C)

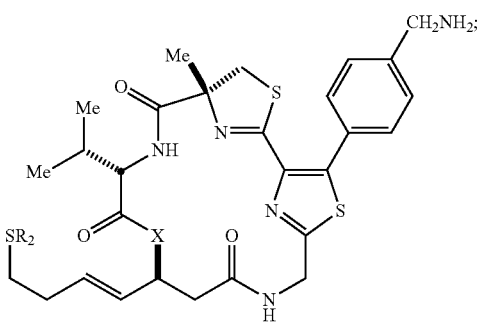

wherein X=NH, or NR, wherein R is H or lower alkyl; wherein $R_2$=H, acyl, or cleavable $SR_5$, wherein $R_5$=folate, methotrexate, cytokines, peptide, carbohydrate, or another molecule of the same (i.e., resulting in a homodimer); or a pharmaceutically acceptable salt, solvate, clathrate, or stereoisomer thereof.

3. A compound having a structure selected from the group consisting of:

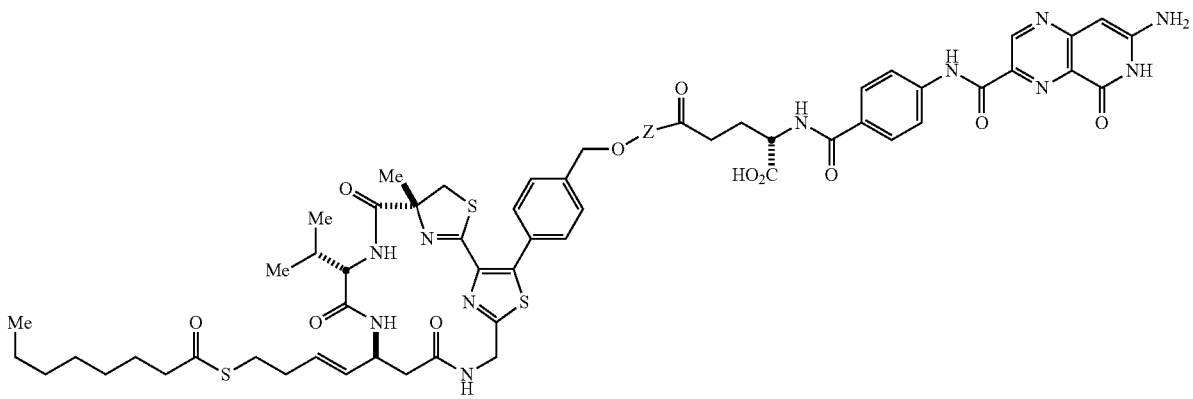

where Z = bond, or linker

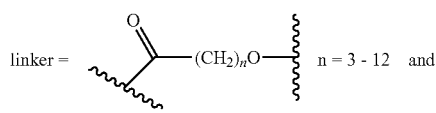

n = 3 - 12 and

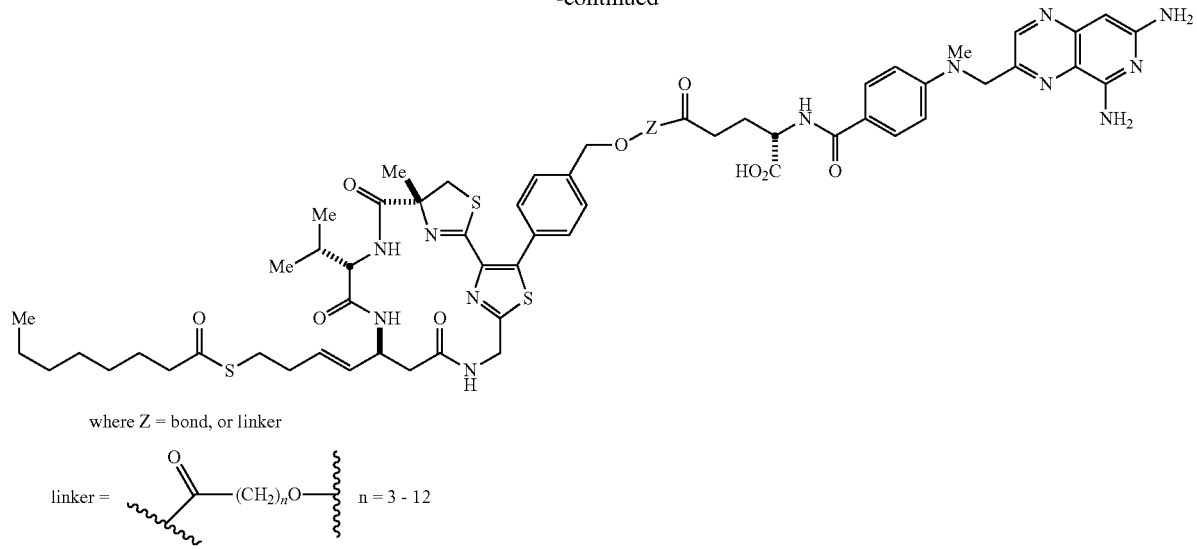

where Z = bond, or linker or a pharmaceutically acceptable salt, solvate, clathrate, or stereoisomer thereof.

4. A method for alleviating symptoms of leukemia, non-small cell lung cancer, colon cancer, central nervous system cancer, renal cancer, prostate cancer, or breast cancer in a subject, comprising administering to the subject a therapeutically effective amount of the compound of claim 1.

5. The method of claim 4, wherein the symptoms are of leukemia.

6. The method of claim 4, further comprising treating said subject with an additional form of therapy for cancer.

7. A pharmaceutical composition comprising a therapeutically effective amount of the compound of claim 1 and at least one pharmaceutically acceptable excipient.

8. A composition comprising a radiolabelled compound of claim 1.

9. A method for alleviating symptoms of leukemia, non-small cell lung cancer, colon cancer, central nervous system cancer, renal cancer, prostate cancer, or breast cancer in a subject, comprising administering to the subject a therapeutically effective amount of the compound of claim 2.

10. The method of claim 9, wherein the symptoms are of leukemia.

11. The method of claim 9, further comprising treating said subject with an additional form of therapy for cancer.

12. A pharmaceutical composition comprising a therapeutically effective amount of the compound of claim 2 and at least one pharmaceutically acceptable excipient.

13. A composition comprising a radiolabelled compound of claim 2.

14. A method for alleviating symptoms of leukemia, non-small cell lung cancer, colon cancer, central nervous system cancer, renal cancer, prostate cancer, or breast cancer in a subject, comprising administering to the subject a therapeutically effective amount of the compound of claim 3.

15. The method of claim 14, wherein the symptoms are of leukemia.

16. The method of claim 14, further comprising treating said subject with an additional form of therapy for cancer.

17. A pharmaceutical composition comprising a therapeutically effective amount of the compound of claim 3 and at least one pharmaceutically acceptable excipient.

18. A composition comprising a radiolabelled compound of claim 3.

* * * * *

UNITED STATES PATENT AND TRADEMARK OFFICE
CERTIFICATE OF CORRECTION

PATENT NO. : 10,538,534 B2
APPLICATION NO. : 15/555792
DATED : January 21, 2020
INVENTOR(S) : Williams et al.

It is certified that error appears in the above-identified patent and that said Letters Patent is hereby corrected as shown below:

In the Claims

In Claim 1, Column 74, Line 4, please delete "(i.e., resulting in a homodimer)".

In Claim 2, Column 74, Line 31, please delete "(i.e., resulting in a homodimer)".

In Claim 3, Column 74, Line 37, please delete the first structure " ", and replace with the following structure -- --.

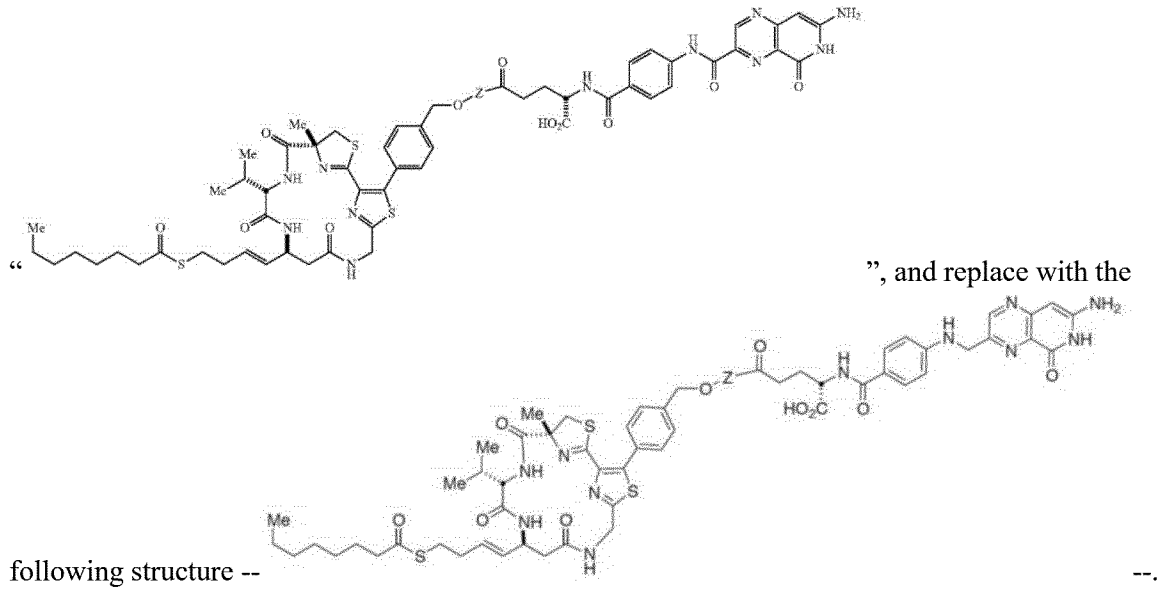

Signed and Sealed this
Seventh Day of April, 2020

Andrei Iancu
*Director of the United States Patent and Trademark Office*